(12) United States Patent
Schieber

(10) Patent No.: US 10,709,547 B2
(45) Date of Patent: Jul. 14, 2020

(54) OCULAR IMPLANT DELIVERY SYSTEM AND METHOD

(71) Applicant: IVANTIS, INC., Irvine, CA (US)

(72) Inventor: Andrew T. Schieber, Irvine, CA (US)

(73) Assignee: IVANTIS, INC., Irvine, CA (US)

( * ) Notice: Subject to any disclaimer, the term of this patent is extended or adjusted under 35 U.S.C. 154(b) by 493 days.

(21) Appl. No.: 15/325,628

(22) PCT Filed: Jul. 14, 2015

(86) PCT No.: PCT/US2015/040414
§ 371 (c)(1),
(2) Date: Jan. 11, 2017

(87) PCT Pub. No.: WO2016/011056
PCT Pub. Date: Jan. 21, 2016

(65) Prior Publication Data
US 2017/0156848 A1    Jun. 8, 2017

Related U.S. Application Data

(60) Provisional application No. 62/024,295, filed on Jul. 14, 2014.

(51) Int. Cl.
*A61F 2/14* (2006.01)
*A61F 9/007* (2006.01)
*A61F 9/00* (2006.01)

(52) U.S. Cl.
CPC .............. *A61F 2/148* (2013.01); *A61F 2/14* (2013.01); *A61F 9/00781* (2013.01); *A61F 9/0017* (2013.01)

(58) Field of Classification Search
CPC .......... A61F 2/148; A61F 2/14; A61F 2/1662; A61F 2/1664; A61F 2/1667; A61F 2/167;
(Continued)

(56) References Cited

U.S. PATENT DOCUMENTS

| 703,296 A | 6/1902 | Arnold |
| 1,601,709 A | 10/1926 | Windom |

(Continued)

FOREIGN PATENT DOCUMENTS

| AU | 1998/76197 B2 | 2/1999 |
| CN | 1950091 A | 4/2007 |

(Continued)

OTHER PUBLICATIONS

Kirkness et al.; The Use of Silicone Drainage Tubing to Control Post-Keratoplasty Glaucoma; Eye; 2 (pt 5); pp. 583-590; Apr. 1988.
(Continued)

*Primary Examiner* — Diane D Yabut
(74) *Attorney, Agent, or Firm* — Shay Glenn LLP

(57) ABSTRACT

A method and system for deploying an ocular implant into Schlemm's canal of an eye. The method includes the steps of inserting a distal end of a cannula through a cornea of the eye and into an anterior chamber of the eye, the cannula having a distal opening extending from the distal end and through a side wall, a curved distal portion and a curved intermediate portion; placing the distal opening of the cannula into fluid communication with Schlemm's canal; advancing the ocular implant distally through the cannula with a delivery tool engaged with the ocular implant, a proximal portion of the ocular implant engaging the delivery tool proximal to a distal portion of the delivery tool; and disengaging the ocular implant and the delivery tool when the proximal portion of the ocular implant reaches the cannula distal opening.

24 Claims, 33 Drawing Sheets

(58) Field of Classification Search
CPC .... A61F 2/1672; A61F 2/1675; A61F 2/1678; A61F 9/00781; A61F 9/0017
See application file for complete search history.

(56) References Cited

U.S. PATENT DOCUMENTS

| | | |
|---|---|---|
| 2,716,983 A | 9/1955 | George et al. |
| 3,071,135 A | 1/1963 | Baldwin et al. |
| 3,788,327 A | 1/1974 | Donowitz et al. |
| 3,811,442 A | 5/1974 | Maroth |
| 3,858,577 A | 1/1975 | Bass et al. |
| 3,884,236 A | 5/1975 | Krasnov |
| 3,948,271 A | 4/1976 | Akiyama |
| 3,982,541 A | 9/1976 | L'Esperance |
| 4,037,604 A | 7/1977 | Newkirk |
| 4,134,405 A | 1/1979 | Smit |
| 4,273,109 A | 6/1981 | Enderby |
| 4,391,275 A | 7/1983 | Fankhauser et al. |
| 4,428,746 A | 1/1984 | Mendez |
| 4,457,757 A | 7/1984 | Molteno |
| 4,461,294 A | 7/1984 | Baron |
| 4,470,407 A | 9/1984 | Hussein |
| 4,497,319 A | 2/1985 | Sekine et al. |
| 4,501,274 A | 2/1985 | Skjaerpe |
| 4,517,973 A | 5/1985 | Sunago et al. |
| 4,538,608 A | 9/1985 | L'Esperance |
| 4,548,205 A | 10/1985 | Armeniades et al. |
| 4,551,129 A | 11/1985 | Coleman et al. |
| 4,558,698 A | 12/1985 | O'Dell |
| 4,559,942 A | 12/1985 | Eisenberg |
| 4,566,438 A | 1/1986 | Liese et al. |
| 4,580,559 A | 4/1986 | L'Esperance |
| 4,583,539 A | 4/1986 | Karlin et al. |
| 4,601,713 A | 7/1986 | Fuquo |
| 4,604,087 A | 8/1986 | Joseph |
| 4,633,866 A | 1/1987 | Peyman et al. |
| 4,658,816 A | 4/1987 | Ector |
| 4,660,546 A | 4/1987 | Herrick et al. |
| 4,671,273 A | 6/1987 | Lindsey |
| 4,689,040 A | 8/1987 | Thompson |
| 4,699,140 A | 10/1987 | Holmes et al. |
| 4,706,669 A | 11/1987 | Schlegel |
| 4,722,350 A | 2/1988 | Armeniades et al. |
| 4,722,724 A | 2/1988 | Schocket |
| 4,729,373 A | 3/1988 | Peyman |
| 4,733,665 A | 3/1988 | Palmaz |
| 4,750,901 A | 6/1988 | Molteno |
| 4,770,654 A | 9/1988 | Rogers et al. |
| 4,791,927 A | 12/1988 | Menger |
| 4,826,478 A | 5/1989 | Schocket |
| 4,846,172 A | 7/1989 | Berlin |
| 4,861,341 A | 8/1989 | Woodburn |
| 4,876,250 A | 10/1989 | Clark |
| 4,880,000 A | 11/1989 | Holmes et al. |
| 4,886,488 A | 12/1989 | White |
| 4,919,130 A | 4/1990 | Stoy et al. |
| 4,925,299 A | 5/1990 | Meisberger et al. |
| 4,934,363 A | 6/1990 | Smith et al. |
| 4,934,809 A | 6/1990 | Volk |
| 4,936,825 A | 6/1990 | Ungerleider |
| 4,946,436 A | 8/1990 | Smith |
| 4,968,296 A | 11/1990 | Ritch et al. |
| 4,994,060 A | 2/1991 | Rink et al. |
| 5,034,010 A | 7/1991 | Kittrell et al. |
| 5,092,837 A | 3/1992 | Ritch et al. |
| 5,123,902 A | 6/1992 | Muller et al. |
| 5,127,901 A | 7/1992 | Odrich |
| 5,129,895 A | 7/1992 | Vassiliadis et al. |
| 5,178,604 A | 1/1993 | Baerveldt et al. |
| 5,180,362 A | 1/1993 | Worst |
| 5,190,552 A | 3/1993 | Kelman |
| 5,213,569 A | 5/1993 | Davis |
| 5,238,004 A | 8/1993 | Sahatjian et al. |
| 5,246,452 A | 9/1993 | Sinnott |
| 5,254,112 A | 10/1993 | Sinofsky et al. |
| 5,273,056 A | 12/1993 | McLaughlin et al. |
| 5,290,267 A | 3/1994 | Zimmermann |
| 5,300,020 A | 4/1994 | L'Esperance |
| 5,359,685 A | 10/1994 | Waynant et al. |
| 5,360,399 A | 11/1994 | Stegmann |
| 5,371,078 A | 12/1994 | Clark et al. |
| 5,372,577 A | 12/1994 | Ungerleider |
| 5,445,637 A | 8/1995 | Bretton |
| 5,454,796 A | 10/1995 | Krupin |
| 5,458,615 A | 10/1995 | Klemm et al. |
| 5,501,274 A | 3/1996 | Nguyen et al. |
| 5,536,259 A | 7/1996 | Utterberg |
| 5,575,780 A | 11/1996 | Saito |
| 5,591,223 A | 1/1997 | Lock et al. |
| 5,607,966 A | 3/1997 | Hellberg et al. |
| 5,613,972 A | 3/1997 | Lee et al. |
| 5,626,558 A | 5/1997 | Suson |
| 5,643,250 A | 7/1997 | O'Donnell |
| 5,653,753 A | 8/1997 | Brady et al. |
| 5,657,760 A | 8/1997 | Ying et al. |
| 5,676,669 A | 10/1997 | Colvard |
| 5,704,907 A | 1/1998 | Nordquist et al. |
| 5,713,844 A | 2/1998 | Peyman |
| 5,722,970 A | 3/1998 | Colvard et al. |
| 5,736,491 A | 4/1998 | Patel et al. |
| 5,738,676 A | 4/1998 | Hammer et al. |
| 5,738,677 A | 4/1998 | Colvard et al. |
| 5,785,658 A | 7/1998 | Benaron et al. |
| 5,792,099 A | 8/1998 | DeCamp et al. |
| 5,792,103 A | 8/1998 | Schwartz et al. |
| 5,807,302 A | 9/1998 | Wandel |
| 5,811,453 A | 9/1998 | Yanni et al. |
| 5,865,831 A | 2/1999 | Cozean et al. |
| 5,868,697 A | 2/1999 | Richter et al. |
| 5,879,319 A | 3/1999 | Pynson et al. |
| 5,885,279 A | 3/1999 | Bretton |
| 5,893,837 A | 4/1999 | Eagles et al. |
| 5,895,831 A | 4/1999 | Brasier et al. |
| 5,919,171 A | 7/1999 | Kira et al. |
| 5,948,427 A | 9/1999 | Yamamoto et al. |
| 5,968,058 A | 10/1999 | Richter et al. |
| 5,990,099 A | 11/1999 | Clark |
| 5,993,438 A | 11/1999 | Juhasz et al. |
| 5,997,531 A | 12/1999 | Loeb et al. |
| 6,002,480 A | 12/1999 | Izatt et al. |
| 6,007,511 A | 12/1999 | Prywes |
| 6,050,970 A | 4/2000 | Baerveldt |
| 6,083,193 A | 7/2000 | Kadziauskas et al. |
| 6,099,521 A | 8/2000 | Shadduck |
| 6,102,045 A | 8/2000 | Nordquist et al. |
| 6,146,375 A | 11/2000 | Juhasz et al. |
| 6,177,544 B1 | 1/2001 | Kanai et al. |
| 6,186,974 B1 | 2/2001 | Allan et al. |
| 6,217,584 B1 | 4/2001 | Nun |
| 6,221,078 B1 | 4/2001 | Bylsma |
| 6,238,409 B1 | 5/2001 | Hojeibane |
| 6,241,721 B1 | 6/2001 | Cozean et al. |
| D444,874 S | 7/2001 | Haffner et al. |
| 6,297,228 B1 | 10/2001 | Clark |
| 6,319,274 B1 | 11/2001 | Shadduck |
| 6,328,747 B1 | 12/2001 | Nun |
| 6,375,642 B1 | 4/2002 | Grieshaber et al. |
| 6,398,809 B1 | 6/2002 | Hoffmann et al. |
| 6,409,752 B1 | 6/2002 | Boatman et al. |
| 6,450,984 B1 | 9/2002 | Lynch et al. |
| 6,464,724 B1 | 10/2002 | Lynch et al. |
| 6,471,666 B1 | 10/2002 | Odrich |
| 6,494,857 B1 | 12/2002 | Neuhann |
| 6,508,779 B1 | 1/2003 | Suson |
| 6,508,803 B1 | 1/2003 | Horikawa et al. |
| 6,517,523 B1 | 2/2003 | Kaneko et al. |
| 6,524,275 B1 | 2/2003 | Lynch et al. |
| 6,533,764 B1 | 3/2003 | Haffner et al. |
| 6,533,768 B1 | 3/2003 | Hill |
| 6,544,208 B2 | 4/2003 | Ethier et al. |
| 6,544,249 B1 | 4/2003 | Yu et al. |
| 6,551,289 B1 | 4/2003 | Higuchi et al. |
| 6,626,858 B2 | 9/2003 | Lynch et al. |
| 6,638,239 B1 | 10/2003 | Bergheim et al. |

(56) References Cited

U.S. PATENT DOCUMENTS

| | | |
|---|---|---|
| 6,666,841 B2 | 12/2003 | Gharib et al. |
| 6,699,210 B2 | 3/2004 | Williams et al. |
| 6,699,211 B2 | 3/2004 | Savage |
| 6,702,790 B1 | 3/2004 | Ross |
| 6,726,676 B2 | 4/2004 | Stegmann et al. |
| D490,152 S | 5/2004 | Myall et al. |
| 6,730,056 B1 | 5/2004 | Ghaem et al. |
| 6,736,791 B1 | 5/2004 | Tu et al. |
| 6,780,164 B2 | 8/2004 | Bergheim et al. |
| 6,783,544 B2 | 8/2004 | Lynch et al. |
| 6,827,699 B2 | 12/2004 | Lynch et al. |
| 6,827,700 B2 | 12/2004 | Lynch et al. |
| 6,881,198 B2 | 4/2005 | Brown |
| 6,899,717 B2 | 5/2005 | Weber et al. |
| 6,939,298 B2 | 9/2005 | Brown et al. |
| 6,955,656 B2 | 10/2005 | Bergheim et al. |
| 6,962,573 B1 | 11/2005 | Wilcox |
| 6,981,958 B1 | 1/2006 | Gharib et al. |
| 6,989,007 B2 | 1/2006 | Shadduck |
| 7,018,376 B2 | 3/2006 | Webb et al. |
| 7,094,225 B2 | 8/2006 | Tu et al. |
| 7,125,119 B2 | 10/2006 | Farberov |
| 7,133,137 B2 | 11/2006 | Shimmick |
| 7,135,009 B2 | 11/2006 | Tu et al. |
| 7,147,650 B2 | 12/2006 | Lee |
| 7,163,543 B2 | 1/2007 | Smedley et al. |
| 7,186,232 B1 | 3/2007 | Smedley et al. |
| 7,192,412 B1 | 3/2007 | Zhou et al. |
| 7,207,965 B2 | 4/2007 | Simon |
| 7,207,980 B2 | 4/2007 | Christian et al. |
| 7,220,238 B2 | 5/2007 | Lynch et al. |
| 7,273,475 B2 | 9/2007 | Tu et al. |
| 7,297,130 B2 | 11/2007 | Bergheim et al. |
| 7,331,984 B2 | 2/2008 | Tu et al. |
| 7,488,303 B1 | 2/2009 | Haffner et al. |
| 7,699,882 B2 | 4/2010 | Stamper et al. |
| 7,740,604 B2 | 6/2010 | Schieber et al. |
| 7,931,596 B2 | 4/2011 | Rachlin et al. |
| 7,967,772 B2 | 6/2011 | McKenzie et al. |
| 8,012,115 B2 | 9/2011 | Karageozian |
| 8,123,729 B2 | 2/2012 | Yamamoto et al. |
| 8,172,899 B2 | 5/2012 | Silvestrini et al. |
| 8,267,882 B2 | 9/2012 | Euteneuer et al. |
| 8,282,592 B2 | 10/2012 | Schieber et al. |
| 8,308,701 B2 | 11/2012 | Horvath et al. |
| 8,337,509 B2 | 12/2012 | Schieber et al. |
| 8,372,026 B2 | 2/2013 | Schieber et al. |
| 8,414,518 B2 | 4/2013 | Schieber et al. |
| 8,425,449 B2 | 4/2013 | Wardle et al. |
| 8,475,374 B2 | 7/2013 | Irazoqui et al. |
| 8,512,404 B2 | 8/2013 | Frion et al. |
| 8,529,494 B2 | 9/2013 | Euteneuer et al. |
| 8,540,659 B2 | 9/2013 | Berlin |
| 8,551,166 B2 | 10/2013 | Schieber et al. |
| 8,629,161 B2 | 1/2014 | Mizuno et al. |
| 8,636,647 B2 | 1/2014 | Silvestrini et al. |
| 8,647,659 B2 | 2/2014 | Robinson et al. |
| 8,657,776 B2 | 2/2014 | Wardle et al. |
| 8,663,150 B2 | 3/2014 | Wardle et al. |
| 8,663,303 B2 | 3/2014 | Horvath et al. |
| 8,734,377 B2 | 5/2014 | Schieber et al. |
| 8,808,222 B2 | 8/2014 | Schieber et al. |
| 8,939,906 B2 | 1/2015 | Huang et al. |
| 8,939,948 B2 | 1/2015 | De Juan, Jr. et al. |
| 8,945,038 B2 | 2/2015 | Yablonski |
| 8,951,221 B2 | 2/2015 | Stegmann et al. |
| 8,961,447 B2 | 2/2015 | Schieber et al. |
| 8,974,511 B2 | 3/2015 | Horvath et al. |
| 9,039,650 B2 | 5/2015 | Schieber et al. |
| 9,050,169 B2 | 6/2015 | Schieber et al. |
| 9,066,750 B2 | 6/2015 | Wardle et al. |
| 9,066,783 B2 | 6/2015 | Euteneuer et al. |
| 9,155,655 B2 | 10/2015 | Wardle et al. |
| 9,211,213 B2 | 12/2015 | Wardle et al. |
| 9,226,852 B2 | 1/2016 | Schieber et al. |
| 9,351,874 B2 | 5/2016 | Schieber et al. |
| 9,358,156 B2 | 6/2016 | Wardle et al. |
| 9,402,767 B2 | 8/2016 | Schieber et al. |
| 9,510,973 B2 | 12/2016 | Wardle |
| 9,579,234 B2 | 2/2017 | Wardle et al. |
| 9,636,254 B2 | 5/2017 | Yu et al. |
| 9,642,746 B2 | 5/2017 | Berlin |
| 9,693,901 B2 | 7/2017 | Horvath et al. |
| 9,730,638 B2 | 8/2017 | Haffner et al. |
| 9,757,276 B2 | 9/2017 | Penhasi |
| 9,775,729 B2 | 10/2017 | McClain et al. |
| 9,782,293 B2 | 10/2017 | Doci |
| 9,788,999 B2 | 10/2017 | Schaller |
| 9,795,503 B2 | 10/2017 | Perez Grossmann |
| 9,808,373 B2 | 11/2017 | Horvath et al. |
| 9,820,883 B2 | 11/2017 | Berlin |
| 9,833,357 B2 | 12/2017 | Berlin |
| 10,159,601 B2 | 12/2018 | Berlin |
| 10,335,314 B2 | 7/2019 | Berlin |
| 2001/0002438 A1 | 5/2001 | Sepetka et al. |
| 2002/0003546 A1 | 1/2002 | Mochimaru et al. |
| 2002/0013546 A1 | 1/2002 | Grieshaber et al. |
| 2002/0013572 A1 | 1/2002 | Berlin |
| 2002/0052653 A1 | 5/2002 | Durgin |
| 2002/0072673 A1 | 6/2002 | Yamamoto et al. |
| 2002/0082591 A1 | 6/2002 | Haefliger |
| 2002/0133168 A1 | 9/2002 | Smedley et al. |
| 2002/0143284 A1 | 10/2002 | Tu et al. |
| 2002/0165504 A1 | 11/2002 | Sharp et al. |
| 2002/0165522 A1 | 11/2002 | Holmen |
| 2002/0193805 A1 | 12/2002 | Ott et al. |
| 2003/0004457 A1 | 1/2003 | Andersson |
| 2003/0014092 A1 | 1/2003 | Neuhann |
| 2003/0040754 A1 | 2/2003 | Mitchell et al. |
| 2003/0055372 A1 | 3/2003 | Lynch et al. |
| 2003/0060748 A1 | 3/2003 | Baikoff |
| 2003/0060752 A1 | 3/2003 | Bergheim et al. |
| 2003/0060784 A1 | 3/2003 | Hilgers et al. |
| 2003/0093084 A1 | 5/2003 | Nissan et al. |
| 2003/0097151 A1 | 5/2003 | Smedley et al. |
| 2003/0105456 A1 | 6/2003 | Lin |
| 2003/0125351 A1 | 7/2003 | Azuma et al. |
| 2003/0175324 A1 | 9/2003 | Robinson et al. |
| 2003/0181848 A1 | 9/2003 | Bergheim et al. |
| 2003/0187384 A1 | 10/2003 | Bergheim et al. |
| 2003/0212387 A1 | 11/2003 | Kurtz et al. |
| 2003/0229303 A1 | 12/2003 | Haffner et al. |
| 2003/0236483 A1 | 12/2003 | Ren |
| 2003/0236484 A1 | 12/2003 | Lynch et al. |
| 2004/0024345 A1 | 2/2004 | Gharib et al. |
| 2004/0024453 A1 | 2/2004 | Castillejos |
| 2004/0030302 A1 | 2/2004 | Kamata et al. |
| 2004/0070761 A1 | 4/2004 | Horvath et al. |
| 2004/0082939 A1 | 4/2004 | Berlin |
| 2004/0088048 A1 | 5/2004 | Richter et al. |
| 2004/0092856 A1 | 5/2004 | Dahan |
| 2004/0098124 A1 | 5/2004 | Freeman et al. |
| 2004/0102729 A1 | 5/2004 | Haffner et al. |
| 2004/0106975 A1 | 6/2004 | Solovay et al. |
| 2004/0111050 A1 | 6/2004 | Smedley et al. |
| 2004/0116909 A1 | 6/2004 | Neuberger et al. |
| 2004/0122380 A1 | 6/2004 | Utterberg |
| 2004/0127843 A1 | 7/2004 | Tu et al. |
| 2004/0147870 A1 | 7/2004 | Burns et al. |
| 2004/0193095 A1 | 9/2004 | Shadduck |
| 2004/0193262 A1 | 9/2004 | Shadduck |
| 2004/0199149 A1 | 10/2004 | Myers et al. |
| 2004/0199171 A1 | 10/2004 | Akahoshi |
| 2004/0210181 A1 | 10/2004 | Vass et al. |
| 2004/0210185 A1 | 10/2004 | Tu et al. |
| 2004/0216749 A1 | 11/2004 | Tu |
| 2004/0225357 A1 | 11/2004 | Worst et al. |
| 2004/0228013 A1 | 11/2004 | Goldstein et al. |
| 2004/0249333 A1 | 12/2004 | Bergheim et al. |
| 2004/0254517 A1 | 12/2004 | Quiroz-Mercado et al. |
| 2004/0254519 A1 | 12/2004 | Tu et al. |
| 2004/0254520 A1 | 12/2004 | Porteous et al. |
| 2004/0260228 A1 | 12/2004 | Lynch et al. |
| 2005/0041200 A1 | 2/2005 | Rich |

(56) References Cited

U.S. PATENT DOCUMENTS

| | | |
|---|---|---|
| 2005/0043722 A1 | 2/2005 | Lin |
| 2005/0049578 A1 | 3/2005 | Tu et al. |
| 2005/0090806 A1 | 4/2005 | Lynch et al. |
| 2005/0090807 A1 | 4/2005 | Lynch et al. |
| 2005/0101967 A1 | 5/2005 | Weber et al. |
| 2005/0107734 A1 | 5/2005 | Coroneo |
| 2005/0119601 A9 | 6/2005 | Lynch et al. |
| 2005/0119636 A1 | 6/2005 | Haffner et al. |
| 2005/0125003 A1 | 6/2005 | Pinchuk et al. |
| 2005/0131514 A1 | 6/2005 | Hijlkema et al. |
| 2005/0149114 A1 | 7/2005 | Cartledge et al. |
| 2005/0154443 A1 | 7/2005 | Linder et al. |
| 2005/0165385 A1 | 7/2005 | Simon |
| 2005/0192527 A1 | 9/2005 | Gharib et al. |
| 2005/0197667 A1 | 9/2005 | Chan et al. |
| 2005/0203542 A1 | 9/2005 | Weber et al. |
| 2005/0209549 A1 | 9/2005 | Bergheim et al. |
| 2005/0209550 A1 | 9/2005 | Bergheim et al. |
| 2005/0240168 A1 | 10/2005 | Neuberger et al. |
| 2005/0244464 A1 | 11/2005 | Hughes |
| 2005/0245916 A1 | 11/2005 | Connor |
| 2005/0250788 A1 | 11/2005 | Tu et al. |
| 2005/0260186 A1 | 11/2005 | Bookbinder et al. |
| 2005/0266047 A1 | 12/2005 | Tu et al. |
| 2005/0271704 A1 | 12/2005 | Tu et al. |
| 2005/0273033 A1 | 12/2005 | Grahn et al. |
| 2005/0277864 A1 | 12/2005 | Haffner et al. |
| 2005/0279369 A1 | 12/2005 | Lin |
| 2005/0288619 A1 | 12/2005 | Gharib et al. |
| 2005/0288745 A1 | 12/2005 | Andersen et al. |
| 2006/0020247 A1 | 1/2006 | Kagan et al. |
| 2006/0021623 A1 | 2/2006 | Miller et al. |
| 2006/0032507 A1 | 2/2006 | Tu |
| 2006/0052879 A1 | 3/2006 | Kolb |
| 2006/0069340 A1 | 3/2006 | Simon |
| 2006/0074375 A1 | 4/2006 | Bergheim et al. |
| 2006/0079828 A1 | 4/2006 | Brown |
| 2006/0084907 A1 | 4/2006 | Bergheim et al. |
| 2006/0084954 A1 | 4/2006 | Zadoyan et al. |
| 2006/0106370 A1 | 5/2006 | Baerveldt et al. |
| 2006/0110428 A1 | 5/2006 | deJuan et al. |
| 2006/0116626 A1 | 6/2006 | Smedley et al. |
| 2006/0129141 A1 | 6/2006 | Lin |
| 2006/0149194 A1 | 7/2006 | Conston et al. |
| 2006/0154981 A1 | 7/2006 | Klimko et al. |
| 2006/0155238 A1 | 7/2006 | Shields |
| 2006/0155265 A1 | 7/2006 | Juhasz et al. |
| 2006/0155300 A1 | 7/2006 | Stamper et al. |
| 2006/0167421 A1 | 7/2006 | Quinn |
| 2006/0167466 A1 | 7/2006 | Dusek |
| 2006/0173397 A1 | 8/2006 | Tu et al. |
| 2006/0178674 A1 | 8/2006 | McIntyre |
| 2006/0189915 A1 | 8/2006 | Camras et al. |
| 2006/0189916 A1 | 8/2006 | Bas et al. |
| 2006/0189917 A1 | 8/2006 | Mayr et al. |
| 2006/0195055 A1 | 8/2006 | Bergheim et al. |
| 2006/0195056 A1 | 8/2006 | Bergheim et al. |
| 2006/0195187 A1 | 8/2006 | Stegmann et al. |
| 2006/0200113 A1 | 9/2006 | Haffner et al. |
| 2006/0224146 A1 | 10/2006 | Lin |
| 2006/0241749 A1 | 10/2006 | Tu et al. |
| 2006/0259021 A1 | 11/2006 | Lin |
| 2006/0264971 A1 | 11/2006 | Akahoshi |
| 2006/0276759 A1 | 12/2006 | Kinast et al. |
| 2007/0010827 A1 | 1/2007 | Tu et al. |
| 2007/0021725 A1 | 1/2007 | Villette |
| 2007/0027452 A1 | 2/2007 | Varner et al. |
| 2007/0073275 A1 | 3/2007 | Conston et al. |
| 2007/0088432 A1 | 4/2007 | Solovay et al. |
| 2007/0093794 A1 | 4/2007 | Wang et al. |
| 2007/0093796 A1 | 4/2007 | Raksi et al. |
| 2007/0106200 A1 | 5/2007 | Levy |
| 2007/0106236 A1 | 5/2007 | Coroneo |
| 2007/0112292 A1 | 5/2007 | Tu et al. |
| 2007/0118147 A1 | 5/2007 | Smedley et al. |
| 2007/0121120 A1 | 5/2007 | Schachar |
| 2007/0135681 A1 | 6/2007 | Chin et al. |
| 2007/0173791 A1 | 7/2007 | Raksi |
| 2007/0179520 A1 | 8/2007 | West |
| 2007/0191863 A1 | 8/2007 | De Juan, Jr. et al. |
| 2007/0202186 A1 | 8/2007 | Yamamoto et al. |
| 2007/0208325 A1 | 9/2007 | Kurtz |
| 2007/0219509 A1 | 9/2007 | Tashiro et al. |
| 2007/0219541 A1 | 9/2007 | Kurtz |
| 2007/0235543 A1 | 10/2007 | Zadoyan et al. |
| 2007/0236771 A1 | 10/2007 | Zadoyan et al. |
| 2007/0265582 A1 | 11/2007 | Kaplan et al. |
| 2007/0270945 A1 | 11/2007 | Kobayashi et al. |
| 2007/0276315 A1 | 11/2007 | Haffner et al. |
| 2007/0276316 A1 | 11/2007 | Haffner et al. |
| 2007/0282244 A1 | 12/2007 | Tu et al. |
| 2007/0282245 A1 | 12/2007 | Tu et al. |
| 2007/0293807 A1 | 12/2007 | Lynch et al. |
| 2007/0293872 A1 | 12/2007 | Peyman |
| 2007/0298068 A1 | 12/2007 | Badawi et al. |
| 2008/0015488 A1 | 1/2008 | Tu et al. |
| 2008/0027519 A1 | 1/2008 | Guerrero |
| 2008/0045878 A1 | 2/2008 | Bergheim et al. |
| 2008/0058704 A1 | 3/2008 | Hee et al. |
| 2008/0058777 A1 | 3/2008 | Kurtz et al. |
| 2008/0082088 A1 | 4/2008 | Kurtz et al. |
| 2008/0091224 A1 | 4/2008 | Griffis et al. |
| 2008/0119827 A1 | 5/2008 | Kurtz et al. |
| 2008/0228127 A1 | 9/2008 | Burns et al. |
| 2008/0278687 A1 | 11/2008 | Somani |
| 2008/0288082 A1 | 11/2008 | Deal |
| 2008/0312661 A1 | 12/2008 | Downer et al. |
| 2009/0005852 A1 | 1/2009 | Gittings et al. |
| 2009/0028953 A1 | 1/2009 | Yamamoto et al. |
| 2009/0030363 A1 | 1/2009 | Gellman |
| 2009/0030381 A1 | 1/2009 | Lind et al. |
| 2009/0036843 A1 | 2/2009 | Erskine |
| 2009/0043321 A1 | 2/2009 | Conston et al. |
| 2009/0054723 A1 | 2/2009 | Khairkhahan et al. |
| 2009/0069786 A1 | 3/2009 | Vesely et al. |
| 2009/0082862 A1 | 3/2009 | Schieber et al. |
| 2009/0104248 A1 | 4/2009 | Rapacki et al. |
| 2009/0118716 A1 | 5/2009 | Brownell |
| 2009/0118717 A1 | 5/2009 | Brownell et al. |
| 2009/0118718 A1 | 5/2009 | Raksi et al. |
| 2009/0131921 A1 | 5/2009 | Kurtz et al. |
| 2009/0137988 A1 | 5/2009 | Kurtz |
| 2009/0138081 A1 | 5/2009 | Bergheim et al. |
| 2009/0157062 A1 | 6/2009 | Hauger et al. |
| 2009/0171327 A1 | 7/2009 | Kurtz et al. |
| 2009/0182421 A1 | 7/2009 | Silvestrini et al. |
| 2009/0198248 A1 | 8/2009 | Yeung et al. |
| 2009/0204053 A1 | 8/2009 | Nissan et al. |
| 2009/0247955 A1 | 10/2009 | Yamamoto et al. |
| 2009/0259126 A1 | 10/2009 | Saal et al. |
| 2009/0281520 A1 | 11/2009 | Highley et al. |
| 2009/0281530 A1 | 11/2009 | Korn |
| 2010/0004580 A1 | 1/2010 | Lynch et al. |
| 2010/0036488 A1 | 2/2010 | de Juan et al. |
| 2010/0057072 A1 | 3/2010 | Roman et al. |
| 2010/0114309 A1 | 5/2010 | de Juan et al. |
| 2010/0121342 A1* | 5/2010 | Schieber ............ A61F 9/00781 606/108 |
| 2010/0137981 A1 | 6/2010 | Silvestrini et al. |
| 2010/0173866 A1 | 7/2010 | Hee et al. |
| 2010/0191176 A1 | 7/2010 | Ho et al. |
| 2010/0191177 A1 | 7/2010 | Chang et al. |
| 2010/0234726 A1 | 9/2010 | Sirimanne et al. |
| 2010/0234790 A1 | 9/2010 | Tu et al. |
| 2010/0262174 A1 | 10/2010 | Sretavan et al. |
| 2010/0324543 A1 | 12/2010 | Kurtz et al. |
| 2010/0331858 A1 | 12/2010 | Simaan et al. |
| 2011/0009874 A1 | 1/2011 | Wardle et al. |
| 2011/0028948 A1 | 2/2011 | Raksi et al. |
| 2011/0028949 A1 | 2/2011 | Raksi et al. |
| 2011/0028950 A1 | 2/2011 | Raksi et al. |
| 2011/0028951 A1 | 2/2011 | Raksi et al. |
| 2011/0028952 A1 | 2/2011 | Raksi et al. |
| 2011/0028953 A1 | 2/2011 | Raksi et al. |

(56) References Cited

U.S. PATENT DOCUMENTS

| | | |
|---|---|---|
| 2011/0028954 A1 | 2/2011 | Raksi et al. |
| 2011/0028955 A1 | 2/2011 | Raksi |
| 2011/0028957 A1 | 2/2011 | Raksi et al. |
| 2011/0028958 A1 | 2/2011 | Raksi et al. |
| 2011/0098809 A1 | 4/2011 | Wardle et al. |
| 2011/0196487 A1 | 8/2011 | Badawi et al. |
| 2011/0218523 A1 | 9/2011 | Robl |
| 2011/0224597 A1 | 9/2011 | Stegmann et al. |
| 2012/0010702 A1 | 1/2012 | Stegmann et al. |
| 2012/0022424 A1 | 1/2012 | Yamamoto et al. |
| 2012/0035524 A1 | 2/2012 | Silvestrini |
| 2012/0191064 A1 | 7/2012 | Conston et al. |
| 2012/0271272 A1 | 10/2012 | Hammack et al. |
| 2012/0283557 A1 | 11/2012 | Berlin |
| 2013/0023837 A1 | 1/2013 | Becker |
| 2013/0182223 A1 | 7/2013 | Wardle et al. |
| 2013/0184631 A1 | 7/2013 | Pinchuk |
| 2013/0253402 A1 | 9/2013 | Badawi et al. |
| 2013/0253403 A1 | 9/2013 | Badawi et al. |
| 2013/0253437 A1 | 9/2013 | Badawi et al. |
| 2013/0253438 A1 | 9/2013 | Badawi et al. |
| 2013/0253528 A1 | 9/2013 | Haffner et al. |
| 2013/0267887 A1 | 10/2013 | Kahook et al. |
| 2013/0281908 A1 | 10/2013 | Schaller et al. |
| 2014/0018720 A1 | 1/2014 | Horvath et al. |
| 2014/0066821 A1 | 3/2014 | Freidland et al. |
| 2014/0066831 A1* | 3/2014 | Silvestrini ........... A61F 9/00781 604/8 |
| 2014/0081195 A1 | 3/2014 | Clauson et al. |
| 2015/0018746 A1 | 1/2015 | Hattenbach |
| 2015/0022780 A1 | 1/2015 | John et al. |
| 2015/0038893 A1 | 2/2015 | Haffner et al. |
| 2015/0045714 A1 | 2/2015 | Horvath et al. |
| 2015/0057583 A1 | 2/2015 | Gunn et al. |
| 2015/0057591 A1 | 2/2015 | Horvath et al. |
| 2015/0065940 A1 | 3/2015 | Rangel-Friedman et al. |
| 2015/0080783 A1 | 3/2015 | Berlin |
| 2015/0119787 A1 | 4/2015 | Wardle et al. |
| 2015/0148836 A1 | 5/2015 | Heeren |
| 2015/0223983 A1 | 8/2015 | Schieber et al. |
| 2015/0250649 A1 | 9/2015 | Euteneuer et al. |
| 2015/0282982 A1 | 10/2015 | Schieber et al. |
| 2015/0290033 A1 | 10/2015 | Wardle et al. |
| 2015/0305939 A1 | 10/2015 | Vera et al. |
| 2015/0305940 A1 | 10/2015 | Vera et al. |
| 2015/0313759 A1 | 11/2015 | Vera et al. |
| 2015/0366710 A1 | 12/2015 | Schieber et al. |
| 2016/0051406 A1 | 2/2016 | Wardle et al. |
| 2016/0220417 A1 | 8/2016 | Schieber et al. |
| 2016/0250072 A1 | 9/2016 | Wardle et al. |
| 2017/0127941 A1 | 5/2017 | Ostermeier et al. |
| 2017/0143541 A1 | 5/2017 | Badawi et al. |
| 2017/0172794 A1 | 6/2017 | Varner et al. |
| 2017/0172795 A1 | 6/2017 | Lerner |
| 2017/0172797 A1 | 6/2017 | Horvath et al. |
| 2017/0172798 A1 | 6/2017 | Horvath et al. |
| 2017/0172799 A1 | 6/2017 | Horvath |
| 2017/0172800 A1 | 6/2017 | Romoda et al. |
| 2017/0202708 A1 | 7/2017 | Berlin |
| 2017/0239272 A1 | 8/2017 | Ambati et al. |
| 2017/0251921 A1 | 9/2017 | Phan et al. |
| 2017/0281409 A1 | 10/2017 | Haffner et al. |
| 2017/0290705 A1 | 10/2017 | Wardle et al. |
| 2018/0369017 A1 | 12/2018 | Schieber et al. |

FOREIGN PATENT DOCUMENTS

| | | |
|---|---|---|
| DE | 4226476 C1 | 8/1993 |
| DE | 102012221350 A1 | 5/2014 |
| EP | 0168201 B1 | 6/1988 |
| EP | 0957949 A1 | 11/1996 |
| EP | 0766544 B1 | 5/1998 |
| EP | 1615604 B1 | 8/2009 |
| EP | 2193821 A1 | 6/2010 |
| EP | 1715827 B1 | 12/2010 |
| EP | 2380622 A1 | 10/2011 |
| EP | 2468327 A1 | 6/2012 |
| EP | 2471563 A1 | 7/2012 |
| EP | 1833440 B1 | 8/2012 |
| EP | 3164061 A1 | 5/2017 |
| EP | 2996648 B1 | 6/2017 |
| EP | 1732484 B1 | 8/2017 |
| EP | 1740153 B2 | 8/2017 |
| EP | 3076948 A4 | 8/2017 |
| EP | 3205333 A1 | 8/2017 |
| EP | 3060180 A4 | 9/2017 |
| EP | 3082570 A4 | 9/2017 |
| JP | H10504978 A | 5/1998 |
| JP | 11123205 A | 5/1999 |
| JP | 2002542872 A | 12/2002 |
| JP | 2006517848 A | 8/2006 |
| JP | 2006289075 A | 10/2006 |
| JP | 2010509003 A | 3/2010 |
| JP | 2011502649 A | 1/2011 |
| WO | WO96/20742 A1 | 7/1996 |
| WO | WO99/01063 A1 | 1/1999 |
| WO | WO99/45868 A1 | 9/1999 |
| WO | WO00/07525 A1 | 2/2000 |
| WO | WO00/13627 A1 | 3/2000 |
| WO | WO00/64389 A1 | 11/2000 |
| WO | WO00/64393 A1 | 11/2000 |
| WO | WO00/67687 A1 | 11/2000 |
| WO | WO01/89437 A2 | 11/2001 |
| WO | WO01/97727 A1 | 12/2001 |
| WO | WO02/36052 A1 | 5/2002 |
| WO | WO02/074052 A2 | 9/2002 |
| WO | WO02/080811 A2 | 10/2002 |
| WO | WO03/015659 A2 | 2/2003 |
| WO | WO03/045290 A1 | 6/2003 |
| WO | WO2004/054643 A1 | 7/2004 |
| WO | WO2004/093761 A1 | 11/2004 |
| WO | WO2005/105197 A2 | 11/2005 |
| WO | WO2006/066103 A2 | 6/2006 |
| WO | WO2007/035356 A2 | 3/2007 |
| WO | WO2007/047744 A2 | 4/2007 |
| WO | WO2007/087061 A2 | 8/2007 |
| WO | WO2008/002377 A1 | 1/2008 |
| WO | WO2008/005873 A2 | 1/2008 |
| WO | WO2009/120960 A2 | 10/2009 |
| WO | WO2011/053512 A1 | 5/2011 |
| WO | WO2011/057283 A1 | 5/2011 |
| WO | WO2011/106781 A1 | 9/2011 |
| WO | WO2011/150045 A1 | 12/2011 |
| WO | WO2012/051575 A2 | 4/2012 |
| WO | WO2012/083143 A1 | 6/2012 |
| WO | WO2013/147978 A2 | 10/2013 |
| WO | WO2016/154066 A2 | 9/2016 |

OTHER PUBLICATIONS

Molteno et al.; Long Tube Implants in the Management of Glaucoma; SA Medical Journal; 26; pp. 1062-1066; Jun. 1976.

Molteno; New implant for drainage in glaucoma; Brit. J. Ophthal; 53; pp. 606-615; Sep. 1969.

Schocket et al.; Anterior Chamber Tube Shunt to an Encircling Band in the Treatment of Neovascular Glaucoma and other Refractory Glaucomas; Ophthalmology; 92; pp. 553-562; Apr. 1985.

Wilcox et al.; Hypothesis for Improving Accessory Filtration by Using Geometry; Journal of Glaucoma; 3; pp. 244-247; Fall 1994.

Berlin et al.; U.S. Appl. No. 15/868,904 entitled Methods and systems for OCT guided glaucoma surgery, filed Jan. 11, 2018.

Cambridge Dictionary; Sensor (definition); 2 pages; retrived from the internet (http://dictionary.cambridge.org/define.asp?dict=CALD &key=71811 >) on Aug. 14, 2018.

Dietlein et al.; Morphological variability of the trabecular meshwork in glaucoma patients: implications for non-perforating glaucoma surgery; British Journal of Ophthalmology; 84(12); pp. 1354-1359; Dec. 2000.

Huang et al.; Optical coherence tomography; Science; 254(5035); pp. 1178-1181; 12 pages (Author Manuscript); Nov. 1991.

(56) References Cited

OTHER PUBLICATIONS

Johnstone; Aqueous humor outflow system overview; Becker-Shaffer's Diagnosis and Therapy of the Glaucomas; Part 2 Aqueous Humor Dynamics; Chapter 3; pp. 25-46; Mosby Elseveir; (year of pub. sufficiently earlier than effective US filing date and any foreign priority date) 2009.
Lee et al.; Short-pulsed neodymium-YAG laser trabeculotomy. An in vivo morphological study in the human eye; Investigative Ophthalmology and Visual Science; 29(11); pp. 1698-1707; Nov. 1988.
Macmilla Online Dictionary; Detector (definition); Macmilla On Line Dictionary; 2 pages; retrived from the internet (https://www.macmillandictionary.com/dictionary/british/detector) on Aug. 14, 2018.
Nakamura et al.; Femtosecond laser photodisruption of primate trabecular meshwork: an ex vivo study; Investigative Ophthalmology and Visual Science; 50(3); pp. 1198-1204; Mar. 2009.
Owen; A moving-mirror gonioscope for retinal surgery; British Journal of Ophthalmology; 61(3); pp. 246-247; Mar. 1977.
Oxford Dictionaries; Detector (definition); 1 page; retrieved from the internet (https://en.oxforddictionaries.com/definition/detector) on Aug. 14, 2018.
Oxford Dictionaries; Sensor (definition); 1 page; retrieved from te internet (http://www.askoxford.com/concise_oed/sensor?view=uk>) on Aug. 14, 2018.
Radhakrishnan et al.; Real-time optical coherence tomography of the anterior segment at 1310 nm; Archives of Opthhalmology; 119(8); pp. 1179-1185; Aug. 2001.
Toyran et al.; Femtosecond laser photodisruption of human trabecular meshwork: an in vitro study; Experimental Eye Research; 81(3); pp. 298-305; Sep. 2005.
Van Meter et al.; U.S. Appl. No. 15/751,886 entitled "Ocular implant with pressure sensor and delivery system," filed Feb. 12, 2018.
Bahler, et al.; Trabecular bypass stents decrease intraocular pressure in cultured human anterior segments; Amer. Journal of Ophthalmology; vol. 138, No. 6; pp. 988-994.e2; Dec. 2004.
Camras et al.; A novel schlemm's canal scaffold increases outflow facility in a human anterior segment perfusion model; Invest. Opthalmol. Vis. Sci. ; 53(10); pp. 6115-6121; Sep. 1, 2012.
D'Ermo, et al.; Our results with the operation of ab externo trabeculotomy; Ophthalmologica; vol. 163; pp. 347-355; Feb. 1971.
Ellingsen et al.; Trabeculotomy and sinusotomy in enucleated human eyes; Investigative Ophthalmology; vol. 11; pp. 21-28; Jan. 1972.
Grant; Experimental aqueous perfusion in enucleated human eyes; Archives of Ophthalmology; vol. 69; pp. 783-801; Jun. 1963.
Gulati et al; A novel 8-mm schlemm's canal scaffold reduces outflow resistance in a human anterior segment perfusion model; Invest. Ophthalmol. Vis. Sci.; 54(3); pp. 1698-1704; Mar. 5, 2013.
Hays et al.; Improvement in outflow facility by two novel microinvasive glaucoma surgery implants; Invest. Ophthalmol. Vis. Sci.; 55(3); pp. 1893-1900; Mar. 1, 2014.
Johnstone et al.; Effects of a schlemm canal scaffold on collector channel ostia in human anterior segments; Exp. Eye. Res.; 119; pp. 70-76; Feb. 2014.
Johnstone et al.; "Microsurgery of Schlemm's Canal and the Human Aqueous Outflow System;" American Journal of Ophthalmology, vol. 76 (6): 906-917; Dec. 1973.
Lee et al.; Aqueous-venous shunt and intraocular pressure. Preliminary report of animal studies; Investigative Ophthalmology; vol. 5; No. 1; pp. 59-64; Feb. 1966.
Lynch, Mary G.; U.S. Appl. No. 60/131,030 entitled "Devices and methods for treating glaucoma by enhancing aqueous outflow through schlemm's canal and anterior chamber angle," filed Apr. 26, 1999.
Moses, Robert; The effect of intraocular pressure on resistance to outflow; Survey of Ophthalmology; vol. 22; No. 2; pp. 88-100; Sep.-Oct. 1977.
Mäepea et al.; The pressures in the episcleral veins, schlemm's canal and the trabecular meshwork in monkeys: effects of changes in intraocular pressure; Exp. Eye Res.; vol. 49; pp. 645-663; Oct. 1989.
Rosenquist et al.; Outflow resistance of enucleated human eyes at two different perfusion pressures and different extents of trabeculotomy; Current Eye Res.; vol. 8; No. 12; pp. 1233-1240; Dec. 1989.
Savage, James; Gonioscopy in the management of glaucoma; Am. Academy of Ophthalmology; Focal Points; vol. XXIV; No. 3; pp. 1-14; Mar. 2006.
Schultz, Jared; Canaloplasty procedure shows promise for open-angle glaucoma in European study; Ocular Surgery News; vol. 34; Mar. 1, 2007.
Smit et al.; Effects of viscoelastic injection into schlemm's canal in primate and human eyes; J. Am. Academy of Ophthalmology; vol. 109; No. 4; pp. 786-792; Apr. 2002.
Spiegel et al.; Schlemm's canal implant: a new method to lower intraocular pressure in patients with POAG?; Ophthalmic Surgery and Lasers; vol. 30; No. 6; pp. 492-494; Jun. 1999.
Yuan et al.; Mathematical modeling of outflow facility increase with trabecular meshwork bypass and schlemm canal dilation; J. Glaucoma; 10 pgs.; Mar. 24, 2015 (Epub ahead of print).
Euteneuer et al.; U.S. Appl. No. 15/601,756 entitled "Methods and apparatus for treating glaucoma," filed May 22, 2017.
Berlin; U.S. Appl. No. 16/404,530 entitled "Delivery system and method of use for the eye," filed May 6, 2019.

\* cited by examiner

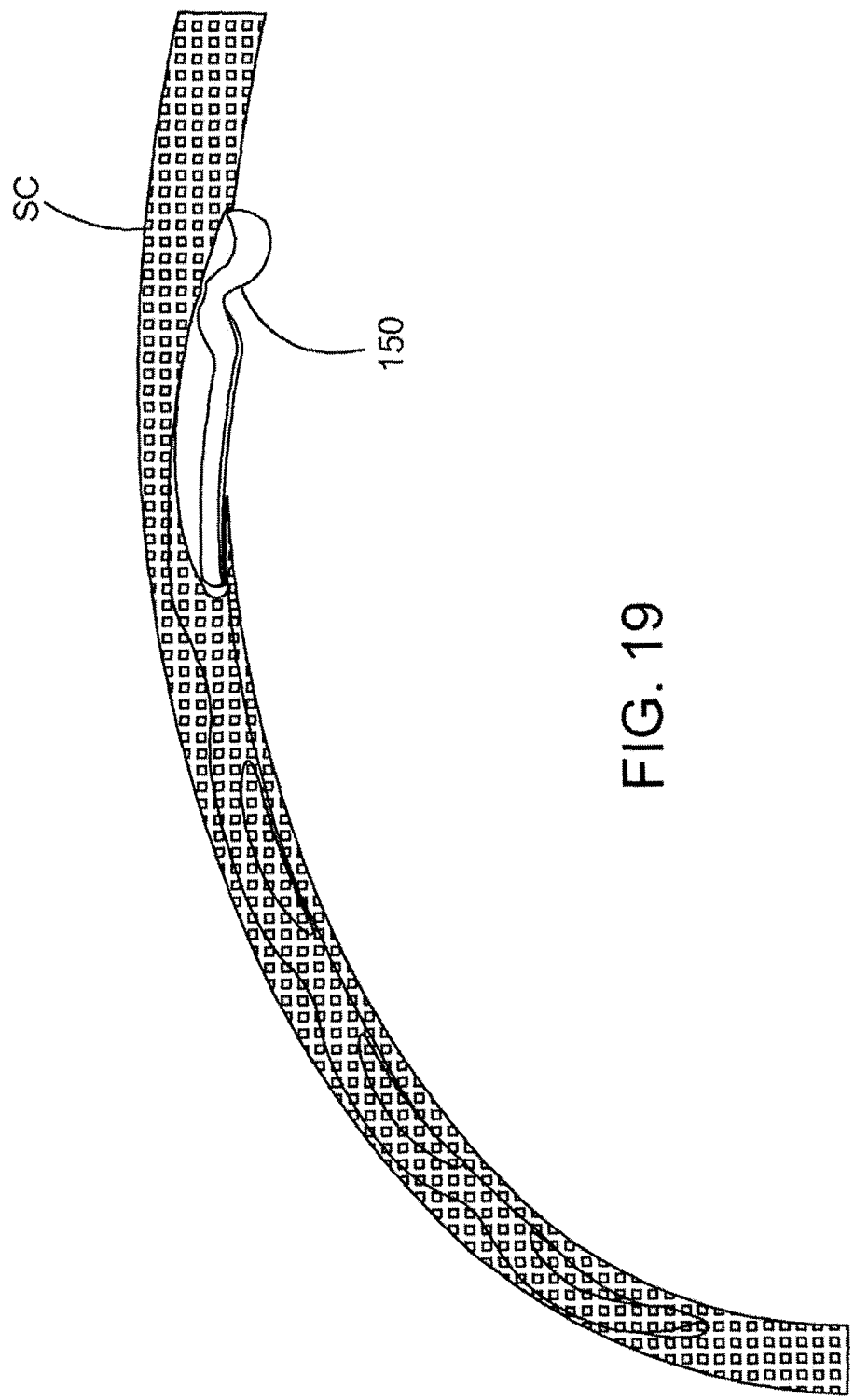

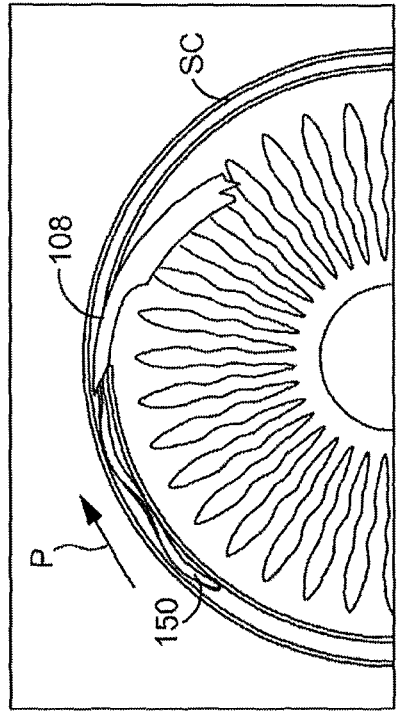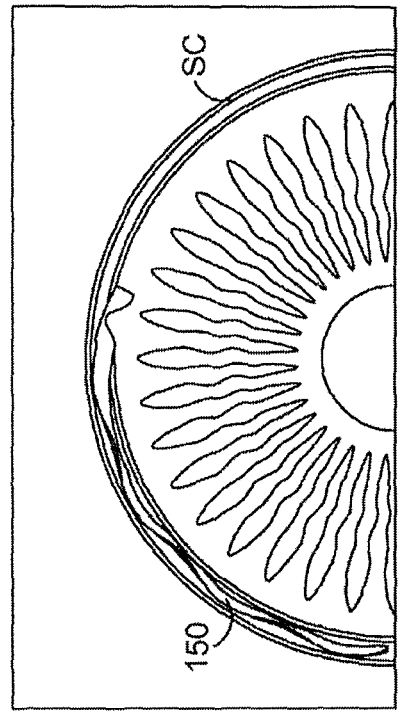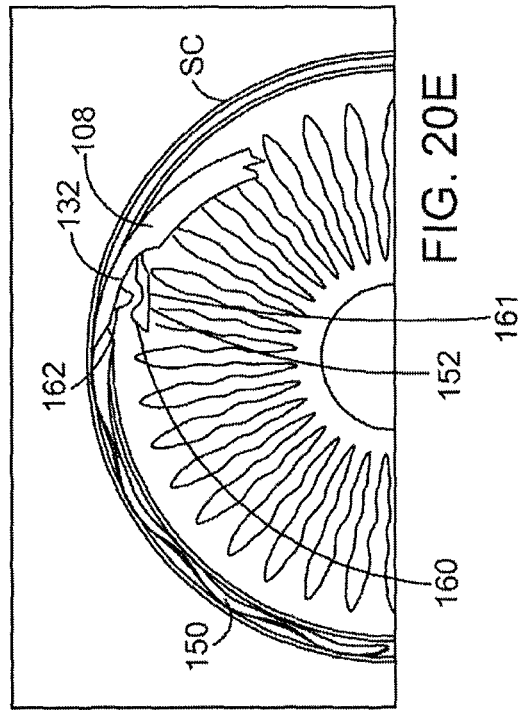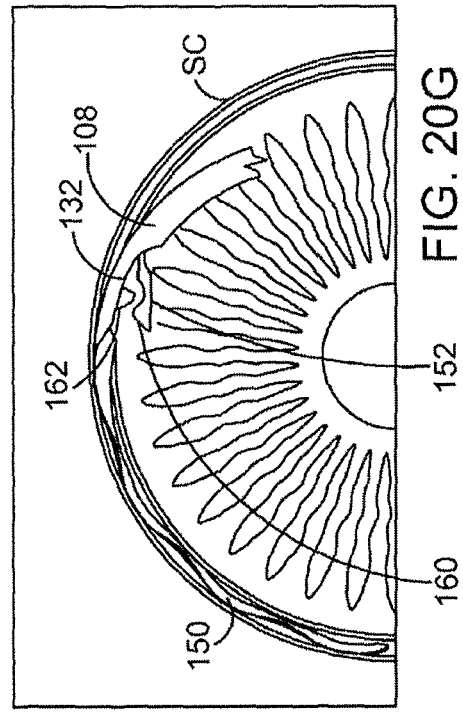

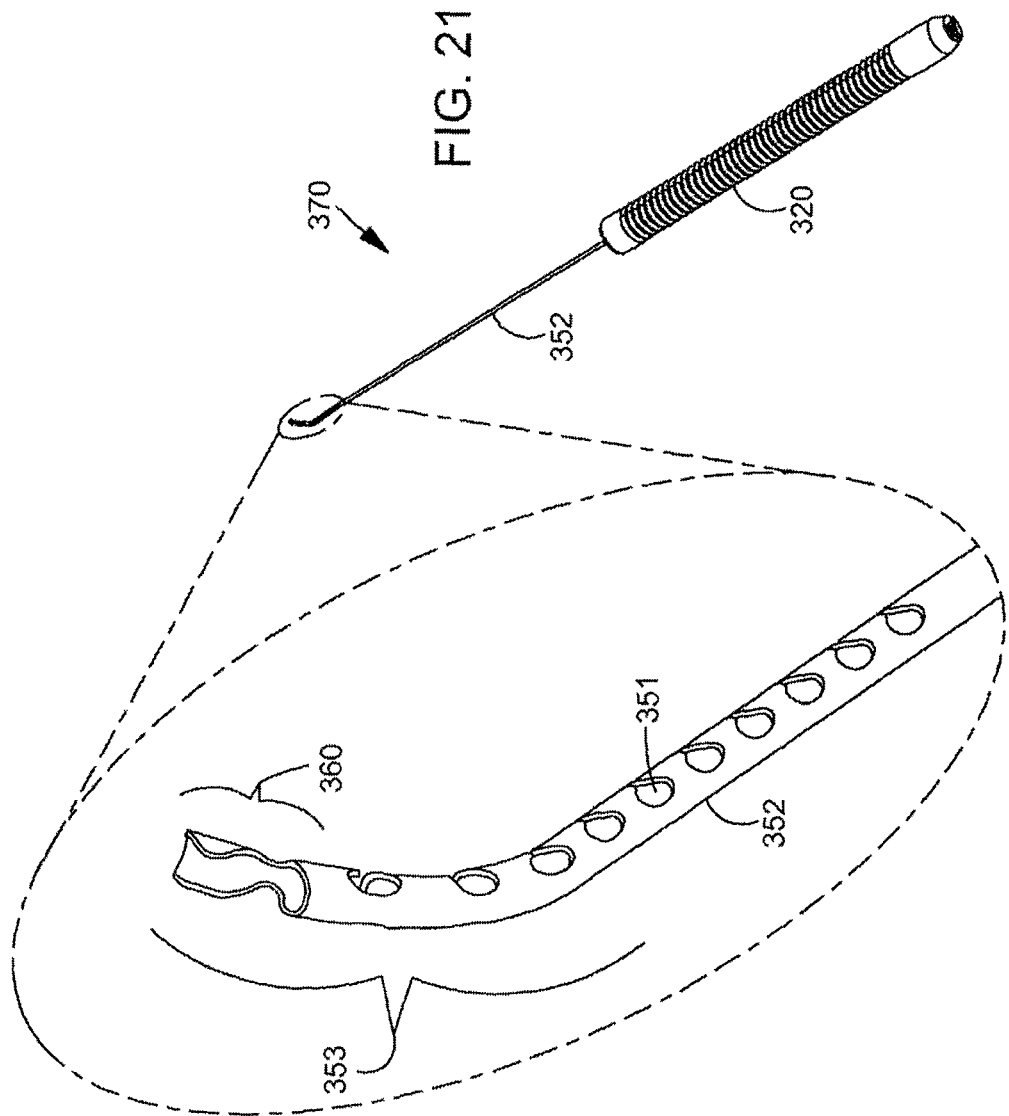

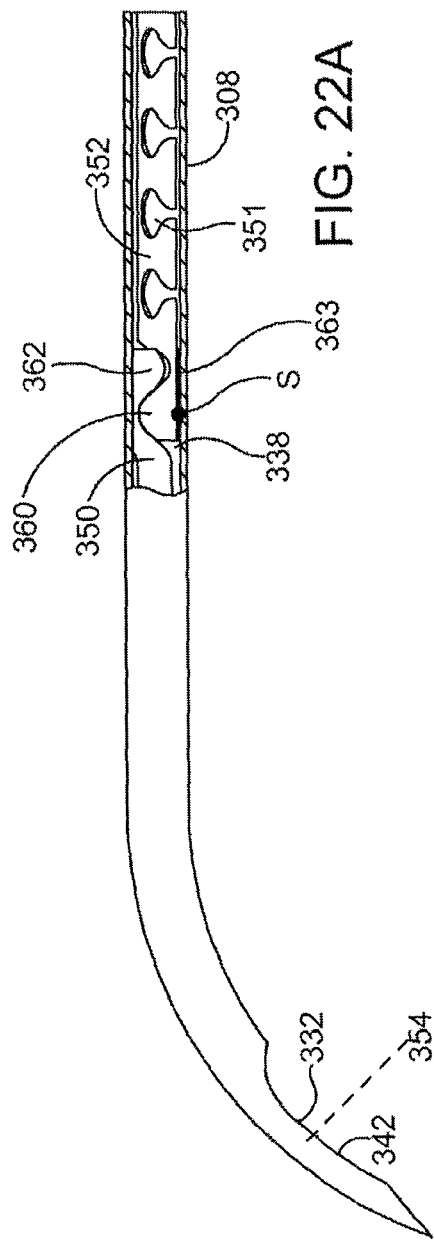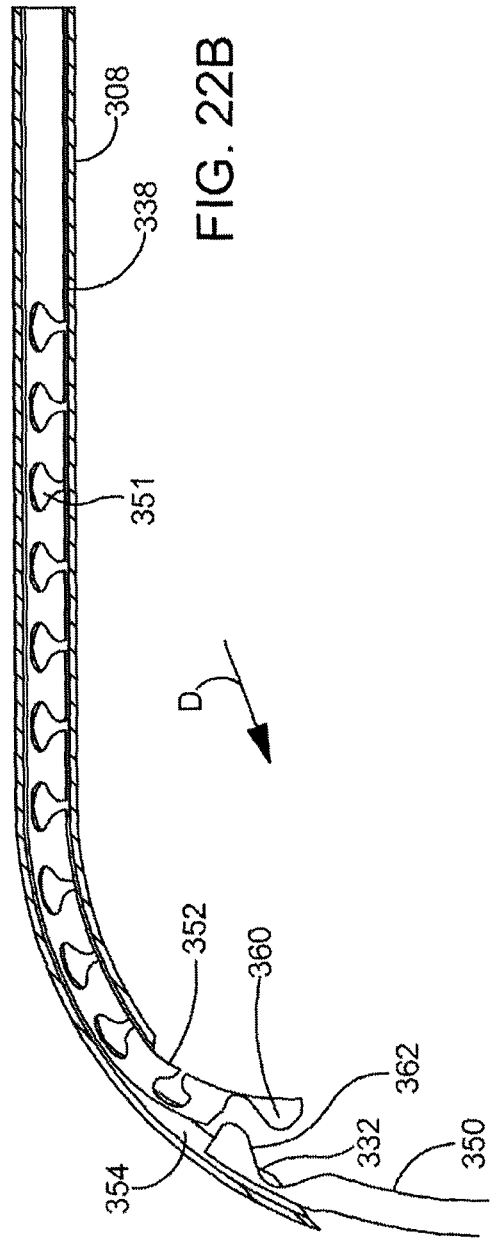

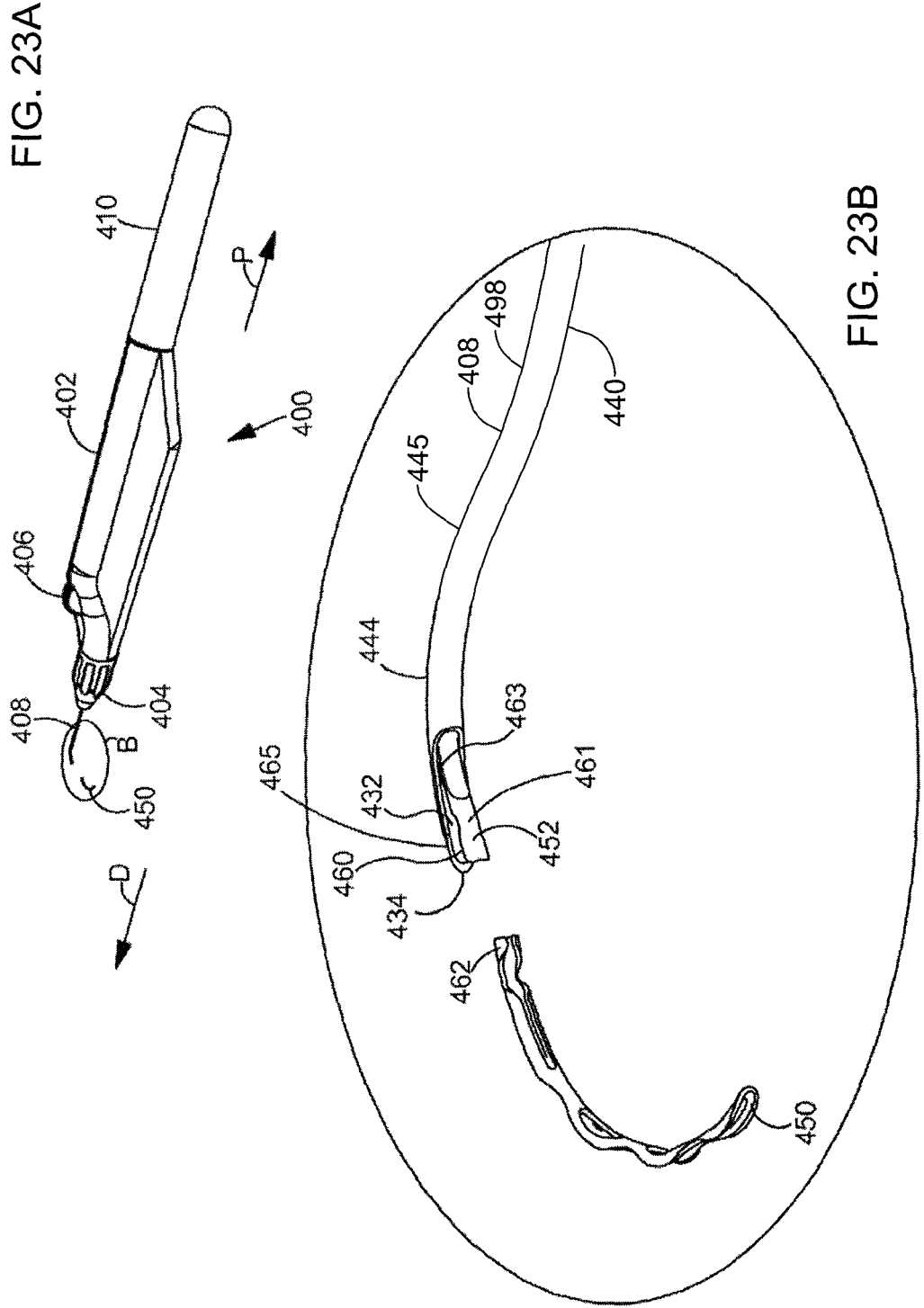

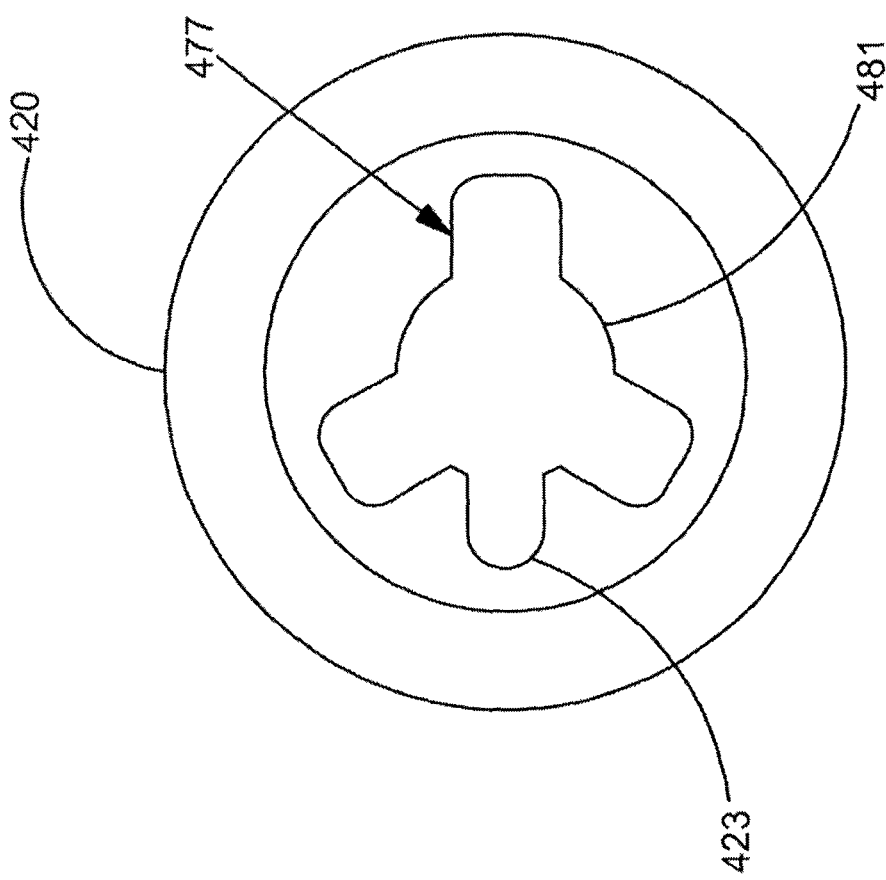

OCULAR IMPLANT DELIVERY SYSTEM AND METHOD

INCORPORATION BY REFERENCE

All publications and patent applications mentioned in this specification are herein incorporated by reference in their entirety to the same extent as if each individual publication or patent application was specifically and individually indicated to be incorporated by reference.

TECHNICAL FIELD

The present disclosure pertains generally, but not by way of limitation, to medical devices, and methods for manufacturing medical devices. More particularly, the present disclosure pertains to devices that are implanted within the eye. Additionally, the present disclosure relates to systems, devices and methods for delivering ocular implants into the eye.

BACKGROUND

According to a draft report by The National Eye Institute (NEI) at The United States National Institutes of Health (NIH), glaucoma is now the leading cause of irreversible blindness worldwide and the second leading cause of blindness, behind cataract, in the world. Thus, the NEI draft report concludes, "it is critical that significant emphasis and resources continue to be devoted to determining the pathophysiology and management of this disease." Glaucoma researchers have found a strong correlation between high intraocular pressure and glaucoma. For this reason, eye care professionals routinely screen patients for glaucoma by measuring intraocular pressure using a device known as a tonometer. Many modern tonometers make this measurement by blowing a sudden puff of air against the outer surface of the eye.

The eye can be conceptualized as a ball filled with fluid. There are two types of fluid inside the eye. The cavity behind the lens is filled with a viscous fluid known as vitreous humor. The cavities in front of the lens are filled with a fluid know as aqueous humor. Whenever a person views an object, he or she is viewing that object through both the vitreous humor and the aqueous humor.

Whenever a person views an object, he or she is also viewing that object through the cornea and the lens of the eye. In order to be transparent, the cornea and the lens can include no blood vessels. Accordingly, no blood flows through the cornea and the lens to provide nutrition to these tissues and to remove wastes from these tissues. Instead, these functions are performed by the aqueous humor. A continuous flow of aqueous humor through the eye provides nutrition to portions of the eye (e.g., the cornea and the lens) that have no blood vessels. This flow of aqueous humor also removes waste from these tissues.

Aqueous humor is produced by an organ known as the ciliary body. The ciliary body includes epithelial cells that continuously secrete aqueous humor. In a healthy eye, a stream of aqueous humor flows out of the anterior chamber of the eye through the trabecular meshwork and into Schlemm's canal as new aqueous humor is secreted by the epithelial cells of the ciliary body. This excess aqueous humor enters the venous blood stream from Schlemm's canal and is carried along with the venous blood leaving the eye.

When the natural drainage mechanisms of the eye stop functioning properly, the pressure inside the eye begins to rise. Researchers have theorized prolonged exposure to high intraocular pressure causes damage to the optic nerve that transmits sensory information from the eye to the brain. This damage to the optic nerve results in loss of peripheral vision. As glaucoma progresses, more and more of the visual field is lost until the patient is completely blind.

In addition to drug treatments, a variety of surgical treatments for glaucoma have been performed. For example, shunts were implanted to direct aqueous humor from the anterior chamber to the extraocular vein (Lee and Scheppens, "Aqueous-venous shunt and intraocular pressure," Investigative Opthalmology (February 1966)). Other early glaucoma treatment implants led from the anterior chamber to a sub-conjunctival bleb (e.g., U.S. Pat. Nos. 4,968,296 and 5,180,362). Still others were shunts leading from the anterior chamber to a point just inside Schlemm's canal (Spiegel et al., "Schlemm's canal implant: a new method to lower intraocular pressure in patients with POAG?" Ophthalmic Surgery and Lasers (June 1999); U.S. Pat. Nos. 6,450,984; 6,450,984).

SUMMARY

The invention provides design, material, and manufacturing method alternatives for medical devices. In a first example, an ocular implant delivery system may comprise a cannula defining a passageway extending from a proximal end to a distal end, the cannula having a distal opening extending through a side wall and the distal end of the cannula to form a trough, a curved distal portion, a curved intermediate portion, and a proximal portion, an ocular implant disposed within the passageway of the cannula, and a delivery tool having a distal interlocking portion engaging a complementary interlocking portion of the ocular implant, and wherein the intermediate portion of the cannula has a first radius of curvature and the distal portion has a second radius of curvature.

Alternatively or additionally to the above example, in another example, the intermediate portion of the cannula extends distally from a first point distal to the proximal end to a second point proximal to the distal end and the distal portion extends distally from the second point to the distal end.

Alternatively or additionally to any of the examples above, in another example the first radius of curvature is greater than the second radius of curvature.

Alternatively or additionally to any of the examples above, in another example, the distal interlocking portion of the delivery tool and the complementary interlocking portion of the ocular implant form a mechanically interlocking connection when the interlocking portion of the delivery tool is proximal to the trough portion of the cannula.

Alternatively or additionally to any of the examples above, in another example, the distal interlocking portion of the delivery tool has an at-rest shape different from the shape of the cannula, the cannula side wall preventing the delivery tool from assuming its at-rest shape when the interlocking portion of the delivery tool is proximal to the trough of the cannula.

Alternatively or additionally to any of the examples above, in another example, the delivery tool at-rest shape is a curve having a smaller radius of curvature than the second radius of curvature of the cannula.

Alternatively or additionally to any of the examples above, in another example, an angle between a line tangential to the distal end of the cannula and a central axis of the proximal portion of the cannula is in the range of 90° to 165°.

In another example, a cannula for deploying an ocular implant into an eye may comprise a tubular member having a side wall and extending from a proximal end to a distal end, the tubular member comprising a passageway extending from the proximal end to the distal end of the tubular member, a generally straight proximal portion extending distally from the proximal end to a first point, a curved intermediate portion extending distally from the first point to a second point proximal to the distal end, a curved distal portion extending distally from the second point to the distal end, and a distal opening extending through the side wall and the distal end of the cannula to form a trough, and wherein the intermediate portion of the cannula has a first radius of curvature and the distal portion has a second radius of curvature and the first radius of curvature is greater than the second radius of curvature.

Alternatively or additionally to any of the examples above, in another example, the passageway is configured to receive an ocular implant.

In another example, a method of deploying an ocular implant into Schlemm's canal of an eye may comprise inserting a distal end of a cannula through a cornea of the eye and into an anterior chamber of the eye, the cannula comprising a passageway extending from a proximal end to a distal end, the cannula further comprising a distal opening extending through a side wall and the distal end of the cannula to form a trough, a curved distal portion, a curved intermediate portion, and a proximal portion, wherein the curved intermediate portion of the cannula has a first radius of curvature and the distal curved portion has a second radius of curvature, placing the distal opening of the cannula into fluid communication with Schlemm's canal, advancing an ocular implant distally through the cannula with a delivery tool engaged with the ocular implant, a proximal portion of the ocular implant engaging the delivery tool proximal to a distal portion of the delivery tool, and disengaging the ocular implant and the delivery tool when the proximal portion of the ocular implant reaches distal opening of the cannula.

Alternatively or additionally to the above example, in another example, the intermediate portion of the cannula extends distally from a first point distal to the proximal end to a second point proximal to the distal end and the distal portion extends distally from the second point to the distal end.

Alternatively or additionally to any of the examples above, in another example, the first radius of curvature is greater than the second radius of curvature.

Alternatively or additionally to any of the examples above, in another example, the disengaging step comprises separating the distal portion of the delivery tool and the ocular implant from each other when the distal portion of the delivery tool passes through the distal opening of the cannula.

Alternatively or additionally to any of the examples above, in another example, the separating step is performed before the distal portion of the delivery tool reaches the distal end of the cannula.

Alternatively or additionally to any of the examples above, in another example, the separating step comprises maintaining contact between the ocular implant and the cannula and moving the distal portion of the delivery tool away from the cannula.

Alternatively or additionally to any of the examples above, in another example, the distal portion of the delivery tool has an at-rest shape, the separating step further comprising permitting the distal portion of the delivery tool to assume its at-rest shape.

Alternatively or additionally to any of the examples above, in another example, the at-rest shape is a curve having a smaller radius of curvature than the second radius of curvature of the cannula.

In another example, a method of deploying an ocular implant into Schlemm's canal of an eye may comprise inserting a distal end of a cannula through an incision in the eye and into an anterior chamber of the eye, wherein a location of the incision is optimized for a cataract surgery, the cannula comprising a passageway extending from a proximal end to a distal end, the cannula further comprising a distal opening extending through a side wall and the distal end of the cannula to form a trough, a curved distal portion, a curved intermediate portion, and a proximal portion, wherein the curved intermediate portion of the cannula has a first radius of curvature and the distal curved portion has a second radius of curvature, placing the distal opening of the cannula into fluid communication with Schlemm's canal such that the cannula enters Schlemm's canal in a substantially tangential orientation, advancing an ocular implant distally through the cannula with a delivery tool engaged with the ocular implant, a proximal portion of the ocular implant engaging the delivery tool proximal to a distal portion of the delivery tool, and disengaging the ocular implant and the delivery tool when the proximal portion of the ocular implant reaches distal opening of the cannula.

Alternatively or additionally to the above example, in another example, the intermediate portion of the cannula extends distally from a first point distal to the proximal end to a second point proximal to the distal end and the distal portion extends distally from the second point to the distal end.

Alternatively or additionally to any of the examples above, in another example, the first radius of curvature is greater than the second radius of curvature.

Alternatively or additionally to any of the examples above, in another example, the disengaging step comprises separating the distal portion of the delivery tool and the ocular implant from each other when the distal portion of the delivery tool passes through the distal opening of the cannula.

Alternatively or additionally to any of the examples above, in another example, the separating step is performed before the distal portion of the delivery tool reaches the distal end of the cannula.

Alternatively or additionally to any of the examples above, in another example, the separating step comprises maintaining contact between the ocular implant and the cannula and moving the distal portion of the delivery tool away from the cannula.

Alternatively or additionally to any of the examples above, in another example, the distal portion of the delivery tool has an at-rest shape, the separating step further comprising permitting the distal portion of the delivery tool to assume its at-rest shape.

Alternatively or additionally to any of the examples above, in another example, the at-rest shape is a curve having a smaller radius of curvature than the second radius of curvature of the cannula.

The above summary of some examples and embodiments is not intended to describe each disclosed embodiment or every implementation of the present disclosure. The Brief Description of the Drawings, and Detailed Description, which follow, more particularly exemplify these embodiments, but are also intended as exemplary and not limiting.

BRIEF DESCRIPTION OF THE DRAWINGS

The disclosure may be more completely understood in consideration of the following detailed description of various embodiments in connection with the accompanying drawings, in which:

FIG. 19 is a perspective view of Schlemm's canal after the cannula shown in FIG. 18 has been withdrawn leaving an inlet portion of the ocular implant in the anterior chamber of the eye and the remainder of ocular implant in Schlemm's canal.

FIG. 20A-FIG. 20H are a series of stylized plan views illustrating example methods in accordance with the detailed description and associated apparatus used while performing those methods.

FIG. 21 is a perspective view showing a delivery tool subassembly 370 that may be part of a delivery system (e.g., the delivery system shown in FIG. 8).

FIG. 22A is a stylized plan view further illustrating the delivery tool shown in FIG. 21. FIG. 22B is an additional stylized plan view illustrating the cannula, ocular implant, and delivery tool shown in FIG. 22A.

FIG. 23A is a perspective view showing another illustrative delivery system including an ocular implant and a cannula defining a passageway that is dimensioned to slidingly receive the ocular implant.

FIG. 23B is an enlarged detail view further illustrating the ocular implant and the cannula shown in FIG. 23A.

FIG. 26A is an end view of the rotating rack gear shown in FIG. 26.

Figure 1:
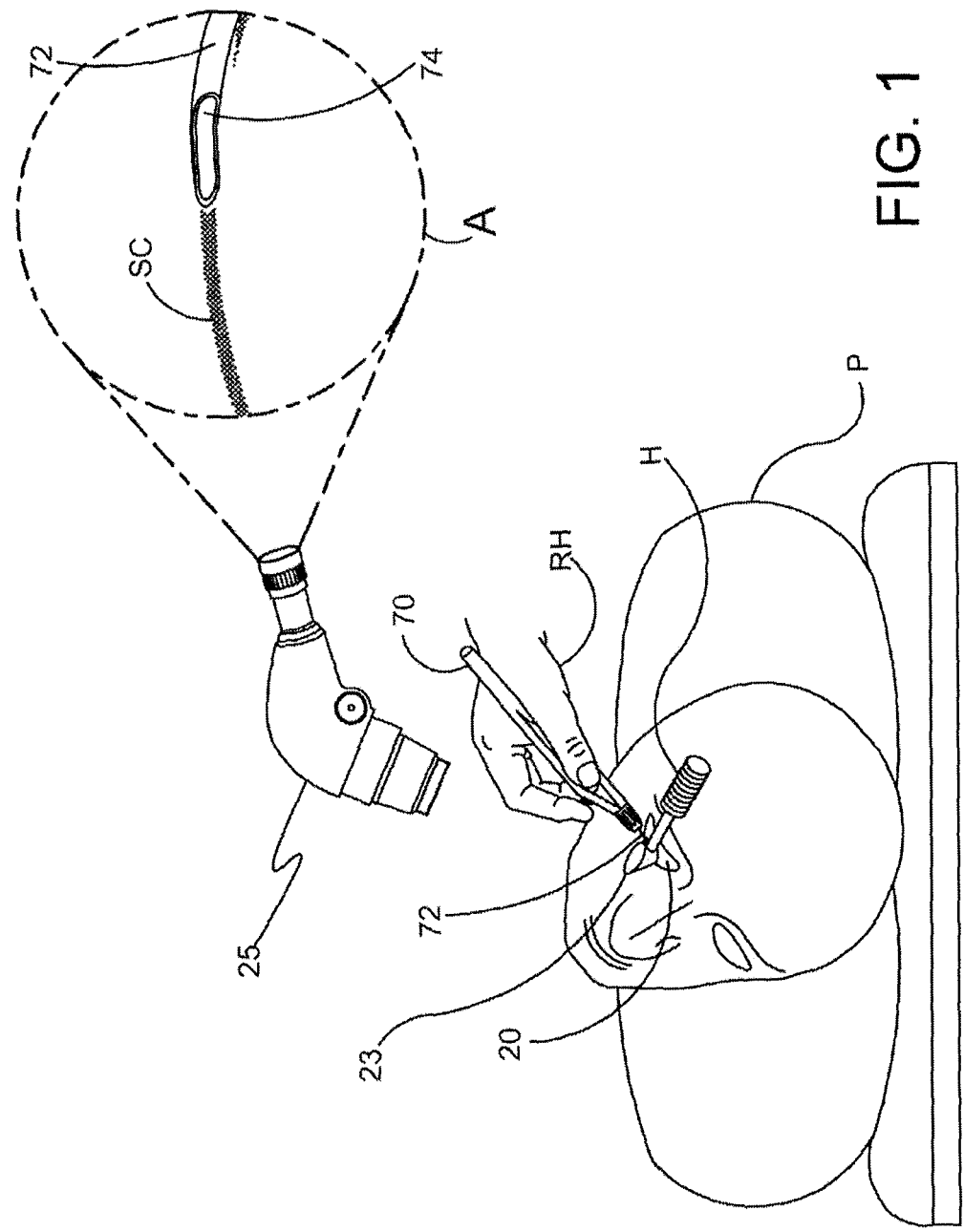
FIG. 1 is a stylized representation of a medical procedure in accordance with this DETAILED DESCRIPTION.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the claimed invention. Those skilled in the art will recognize that the various elements described and/or shown may be arranged in various combinations and configurations without departing from the scope of the disclosure. The detailed description and drawings illustrate example embodiments of the claimed invention.

Definitions of certain terms are provided below and shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same or substantially the same function or result). In many instances, the terms "about" may include numbers that are rounded to the nearest significant figure. Other uses of the term "about" (i.e., in a context other than numeric values) may be assumed to have their ordinary and customary definition(s), as understood from and consistent with the context of the specification, unless otherwise specified.

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a," "an," and "the" include or otherwise refer to singular as well as plural referents, unless the content clearly dictates otherwise. As used in this specification and the appended claims, the term "or" is generally employed to include "and/or," unless the content clearly dictates otherwise.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to affect such feature, structure, or characteristic in connection with other embodiments, whether or not explicitly described, unless clearly stated to the contrary. That is, the various individual elements described below, even if not explicitly shown in a particular combination, are nevertheless contemplated as being combinable or able to be arranged with each other to form other additional embodiments or to complement and/or enrich the described embodiment(s), as would be understood by one of ordinary skill in the art.

The following detailed description should be read with reference to the drawings, in which similar elements in different drawings are identified with the same reference numbers. The drawings, which are not necessarily to scale, depict illustrative embodiments and are not intended to limit the scope of the disclosure.

FIG. 1 is a stylized representation of a medical procedure in accordance with this detailed description. In the procedure of FIG. 1, a physician is treating an eye 20 of a patient P. In the procedure of FIG. 1, the physician is holding a hand piece of a delivery system 70 in his or her right hand RH. The physician's left hand (not shown) may be used to hold the handle H of a gonio lens 23. Alternatively, some physicians may prefer holding the delivery system hand piece in the left hand and the gonio lens handle H in the right hand RH.

During the procedure illustrated in FIG. 1, the physician may view the interior of the anterior chamber using gonio lens 23 and a microscope 25. Detail A of FIG. 1 is a stylized simulation of the image viewed by the physician. A distal portion of a cannula 72 is visible in Detail A. A shadow-like line indicates the location of Schlemm's canal SC which is lying under various tissues (e.g., the trabecular meshwork) that surround the anterior chamber. A distal opening 74 of cannula 72 is positioned near Schlemm's canal SC of eye 20.

Methods in accordance with this detailed description may include the step of advancing the distal end of cannula 72 through the cornea of eye 20 so that a distal portion of cannula 72 is disposed in the anterior chamber of the eye. Cannula 72 may then be used to access Schlemm's canal of the eye, for example, by piercing the wall of Schlemm's canal with the distal end of cannula 72. Distal opening 74 of cannula 72 may be placed in fluid communication with a lumen defined by Schlemm's canal. The ocular implant may be advanced out of distal opening 74 and into Schlemm's canal. Insertion of the ocular implant into Schlemm's canal may facilitate the flow of aqueous humor out of the anterior chamber of the eye.

Figure 2:
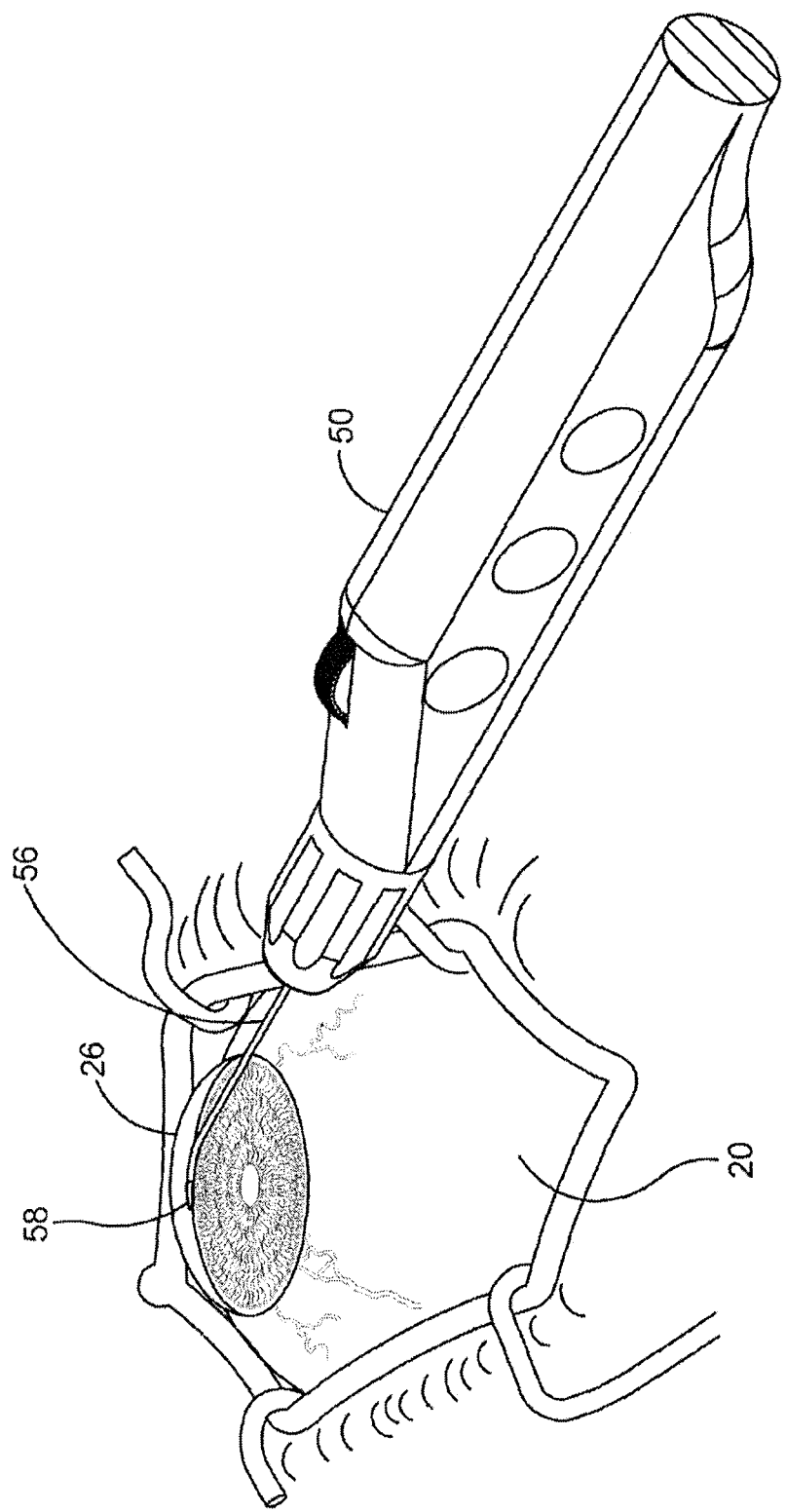
FIG. 2 is an enlarged perspective view further illustrating the delivery system and the eye shown in FIG. 1.

FIG. 2 is an enlarged perspective view further illustrating delivery system 50 and eye 20 shown in the previous figure. In FIG. 2, cannula 56 of delivery system 50 is shown extending through a cornea 26 of eye 20. A distal portion of cannula 56 is disposed inside the anterior chamber defined by cornea 26 of eye 20. In the embodiment of FIG. 2, cannula 56 is configured so that a distal opening 58 of cannula 56 can be placed in fluid communication with Schlemm's canal.

In the embodiment of FIG. 2, an ocular implant is disposed in a passageway defined by cannula 56. Delivery system 50 includes a mechanism that is capable of advancing and retracting the ocular implant along the length of cannula 56. The ocular implant may be placed in Schlemm's canal of eye 20 by advancing the ocular implant through the distal opening of cannula 56 while the distal opening is in fluid communication with Schlemm's canal.

Figure 3:
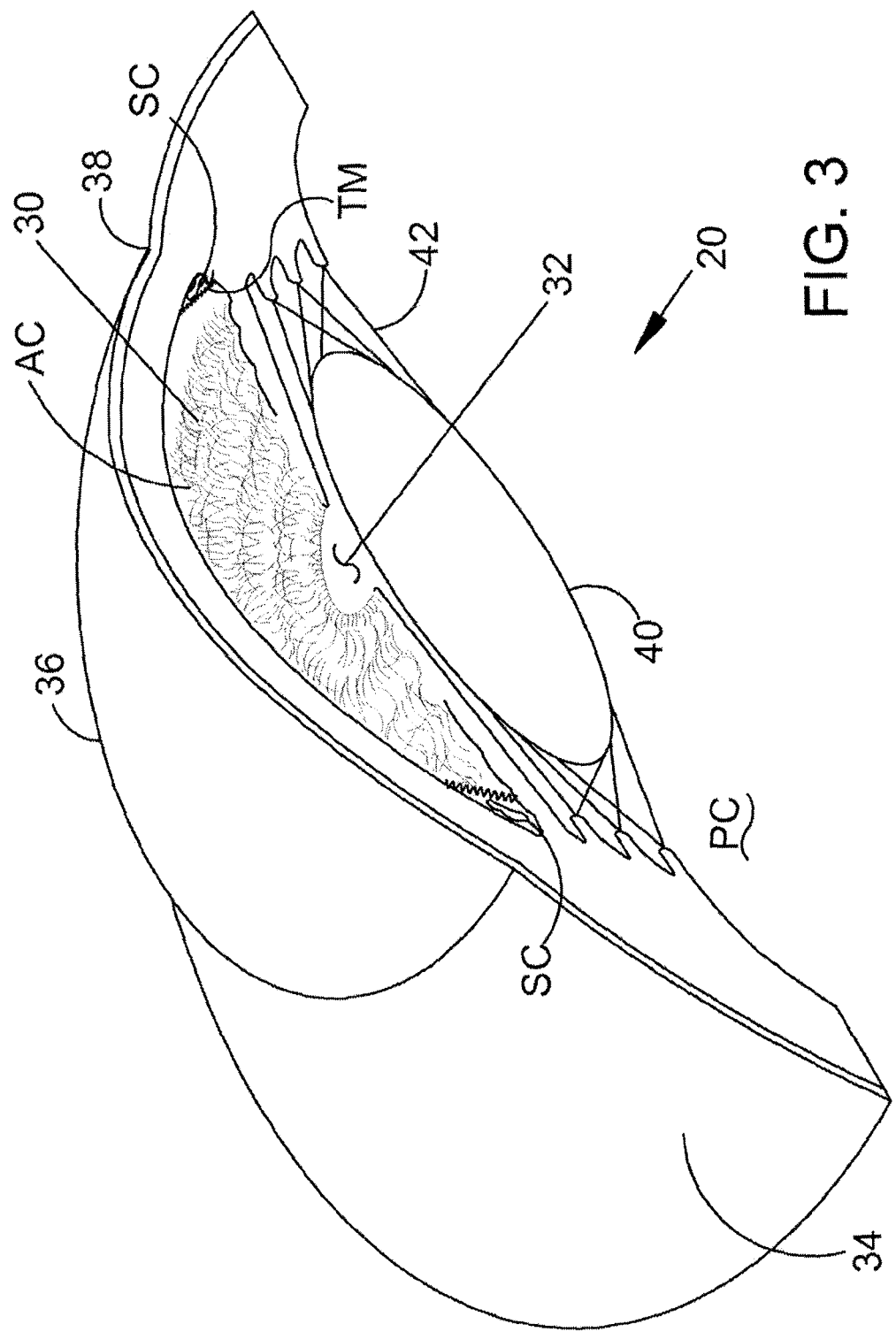
FIG. 3 is a stylized perspective view illustrating the anatomy of an eye.

FIG. 3 is a stylized perspective view illustrating a portion of eye 20 discussed above. Eye 20 includes an iris 30 defining a pupil 32. In FIG. 3, eye 20 is illustrated in a cross-sectional view created by a cutting plane passing through the center of pupil 32. Eye 20 can be conceptualized as a fluid filled ball having two chambers. Sclera 34 of eye 20 surrounds a posterior chamber PC filled with a viscous fluid known as vitreous humor. Cornea 36 of eye 20 encloses an anterior chamber AC that is filled with a fluid known as aqueous humor. The cornea 36 meets the sclera 34 at a limbus 38 of eye 20. A lens 40 of eye 20 is located between anterior chamber AC and posterior chamber PC. Lens 40 is held in place by a number of ciliary zonules 42.

Whenever a person views an object, he or she is viewing that object through the cornea, the aqueous humor, and the lens of the eye. In order to be transparent, the cornea and the lens can include no blood vessels. Accordingly, no blood flows through the cornea and the lens to provide nutrition to these tissues and to remove wastes from these tissues. Instead, these functions are performed by the aqueous humor. A continuous flow of aqueous humor through the eye provides nutrition to portions of the eye (e.g., the cornea and the lens) that have no blood vessels. This flow of aqueous humor also removes waste from these tissues.

Aqueous humor is produced by an organ known as the ciliary body. The ciliary body includes epithelial cells that continuously secrete aqueous humor. In a healthy eye, a stream of aqueous humor flows out of the eye as new aqueous humor is secreted by the epithelial cells of the ciliary body. This excess aqueous humor enters the blood stream and is carried away by venous blood leaving the eye.

Schlemm's canal SC is a tube-like structure that encircles iris 30. Two laterally cut ends of Schlemm's canal SC are visible in the cross-sectional view of FIG. 3. In a healthy eye, aqueous humor flows out of anterior chamber AC and into Schlemm's canal SC. Aqueous humor exits Schlemm's canal SC and flows into a number of collector channels. After leaving Schlemm's canal SC, aqueous humor is absorbed into the venous blood stream and carried out of the eye.

Figure 4:
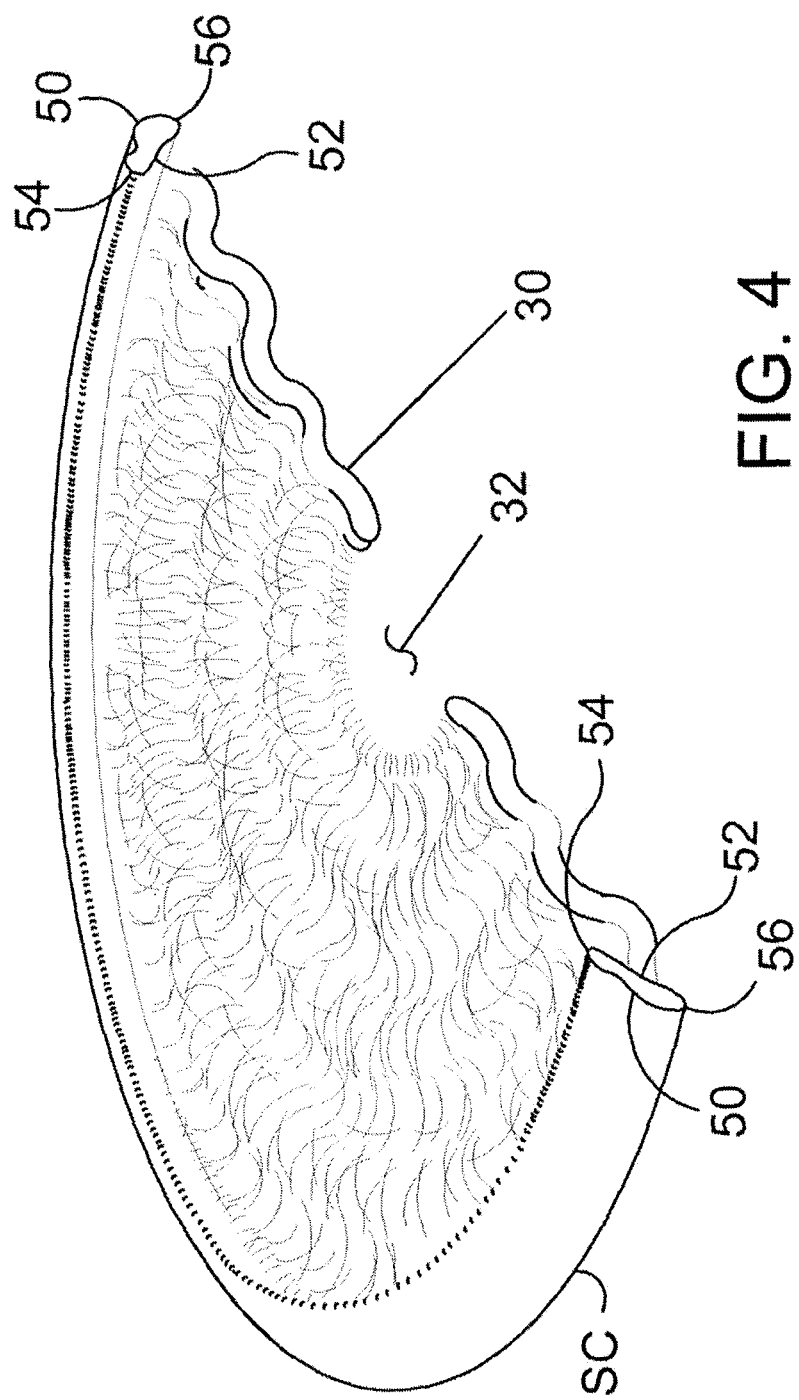
FIG. 4 is a stylized perspective view showing Schlemm's canal and an iris of the eye shown in the previous figure.

FIG. 4 is a stylized perspective view showing Schlemm's canal SC and iris 30 of eye 20 shown in the previous figure. In FIG. 4, Schlemm's canal SC is shown encircling iris 30. With reference to FIG. 4, it will be appreciated that Schlemm's canal SC may overhang iris 30 slightly. Iris 30 defines a pupil 32. In the embodiment of FIG. 4, Schlemm's canal SC and iris 30 are shown in cross-section, with a cutting plane passing through the center of pupil 32.

The shape of Schlemm's canal SC is somewhat irregular, and can vary from patient to patient. The shape of Schlemm's canal SC may be conceptualized as a cylindrical-tube that has been partially flattened. With reference to FIG. 4, it will be appreciated that Schlemm's canal SC has a first major side 50, a second major side 52, a first minor side 54, and a second minor side 56.

Schlemm's canal SC forms a ring around iris 30 with pupil 32 disposed in the center of that ring. With reference to FIG. 4, it will be appreciated that first major side 50 is on the outside of the ring formed by Schlemm's canal SC and second major side 52 is on the inside of the ring formed by Schlemm's canal SC. Accordingly, first major side 50 may be referred to as an outer major side of Schlemm's canal SC and second major side 52 may be referred to as an inner major side of Schlemm's canal SC. With reference to FIG. 4, it will be appreciated that first major side 50 is further from pupil 32 than second major side 52. The outer major wall of Schlemm's canal is supported by scleral tissue of the eye. Elevated pressure inside the eye of a patient suffering from glaucoma may cause the inside major wall of Schlemm's canal to be pressed against the outer major wall of the canal.

Figure 5:
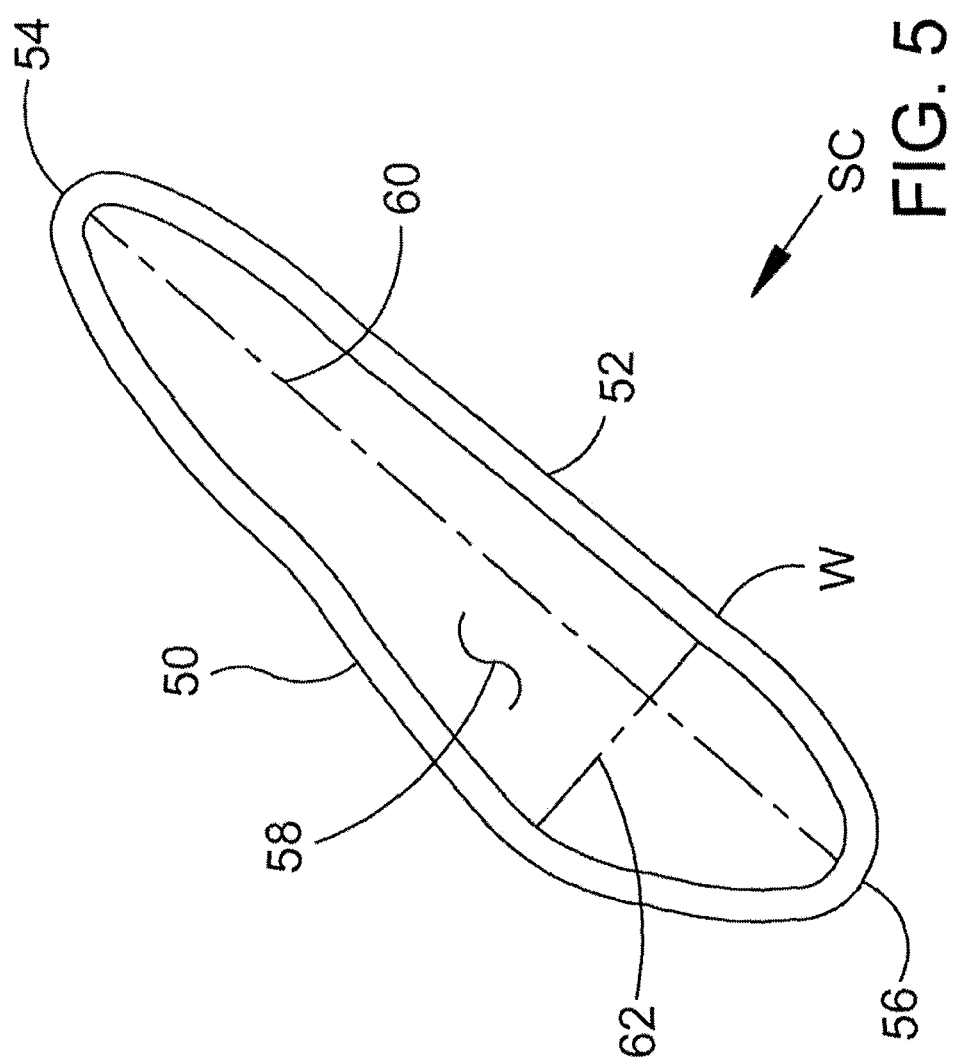
FIG. 5 is an enlarged cross-sectional view further illustrating Schlemm's canal SC shown in the previous figure.

FIG. 5 is an enlarged cross-sectional view further illustrating Schlemm's canal SC shown in the previous figure. With reference to FIG. 5, Schlemm's canal SC comprises a wall W defining a lumen 58. The shape of Schlemm's canal SC is somewhat irregular and can vary from patient to patient. The shape of Schlemm's canal SC may be conceptualized as a cylindrical-tube that has been partially flattened. The cross-sectional shape of lumen 58 may be compared to the shape of an ellipse. A major axis 60 and a minor axis 62 of lumen 58 are illustrated with dashed lines in FIG. 5.

The length of major axis 60 and minor axis 62 can vary from patient to patient. The length of minor axis 62 is between one and thirty micrometers in most patients. The length of major axis 60 is between one hundred and fifty micrometers and three hundred and fifty micrometers in most patients.

With reference to FIG. 5, Schlemm's canal SC comprises a first major side 50, a second major side 52, a first minor side 54, and a second minor side 56. In the embodiment of FIG. 5, first major side 50 is longer than both first minor side 54 and second minor side 56. Also in the embodiment of FIG. 5, second major side 52 is longer than both first minor side 54 and second minor side 56.

FIG. 6A is a perspective view showing a delivery system 100 including an ocular implant 150 and a cannula 108 defining a passageway that is dimensioned to slidingly receive ocular implant 150. Delivery system 100 may be used to advance ocular implant 150 into a target location in the eye of a patient. Examples of target locations that may be suitable in some applications include areas in and around Schlemm's canal, the trabecular meshwork, the suprachoroidal space, and the anterior chamber of the eye. FIG. 6B is an enlarged detail view further illustrating ocular implant 150 and cannula 108 of delivery system 100.

Delivery system 100 of FIG. 6A is capable of controlling the advancement and retraction of ocular implant 150 within cannula 108. Ocular implant 150 may be placed in a target location (e.g., Schlemm's canal) by advancing the ocular implant through a distal opening 132 of cannula 108 while the distal opening is in fluid communication with Schlemm's canal. In the embodiment of FIG. 6A, ocular implant 150 has been advanced through distal opening 132 of cannula 108 for purposes of illustration.

Delivery system 100 of FIG. 6A includes a housing 102, a sleeve 104, and an end cap 110. A tracking wheel 106 extends through a wall of housing 102 in FIG. 6A. Tracking wheel 106 is part of a mechanism that is capable of advancing and retracting a delivery tool 152 of delivery system 100. The delivery tool 152 extends through a distal opening of cannula 108 of FIG. 6B. Rotating the tracking wheel will cause delivery tool 152 to move in an axial direction along a passageway defined by cannula 108. The axial direction may be in a distal direction D or a proximal direction P.

In the embodiment of FIG. 6A, housing 102 is configured to be gripped with one hand while providing control over the axial advancement and retraction of ocular implant via tracking wheel 106. The housing of delivery system 100 results in an advantageous ergonomic relationship of the fingers relative to the hand. This design provides a configuration that will allow a user, such as a physician, to stabilize the device using part of the hand, while leaving the middle or index finger free move independently from the remainder of the hand. The middle or index finger is free to move independently to rotate the wheel for advancing and/or retract the ocular implant.

Figure 6:
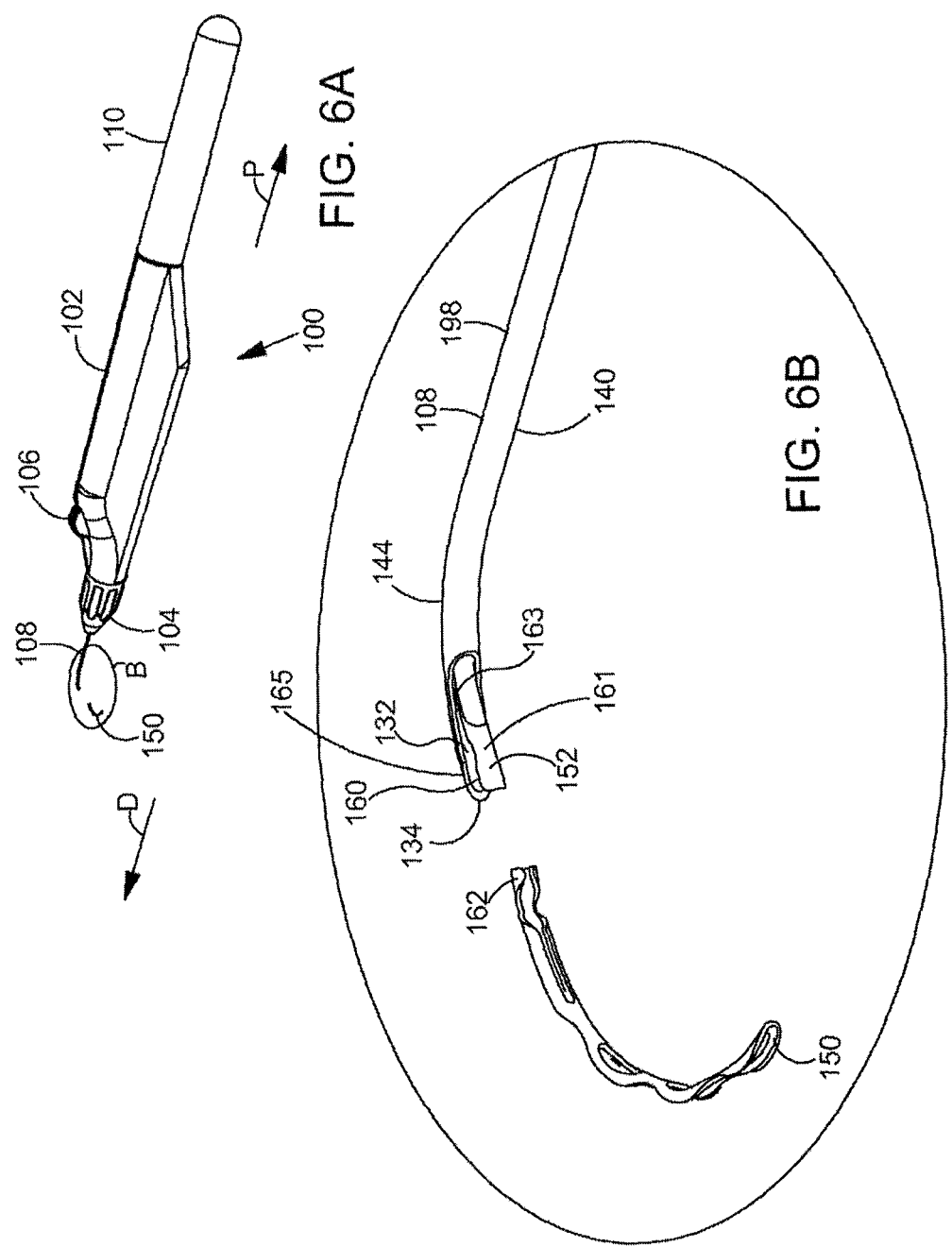
FIG. 6A is a perspective view showing a delivery system including an ocular implant and a cannula defining a passageway that is dimensioned to slidingly receive the ocular implant.
FIG. 6B is an enlarged detail view further illustrating the ocular implant and the cannula 108 shown in FIG. 6A.

FIG. 6B is an enlarged detail view further illustrating ocular implant 150 and a cannula 108 of delivery system 100. Cannula 108 comprises a generally tubular member 198 having proximal portion 140, a distal end 134, and a distal portion 144 extending between distal end 134 and proximal portion 140. In the embodiment of FIG. 6, distal portion 144 is curved. In some useful embodiments, distal portion 144 is dimensioned and configured to be received in the anterior chamber of the eye.

FIG. 6B shows delivery tool 152 of delivery system 100 extending through distal opening 132 of cannula 108. Delivery tool 152 includes an interlocking portion 160 that is configured to form a connection with a complementary interlocking portion 162 of ocular implant 150, as explained in more detail below. In the embodiment of FIG. 6, rotating the tracking wheel will cause delivery tool 152 and ocular implant 150 to move along a path defined by cannula 108. Cannula 108 is sized and configured so that the distal end of cannula 108 can be advanced through the trabecular meshwork of the eye and into Schlemm's canal. Positioning cannula 108 in this way places distal opening 132 in fluid communication with Schlemm's canal. Ocular implant 150 may be placed in Schlemm's canal by advancing the ocular implant through distal opening 132 of cannula 108 while the distal opening is in fluid communication with Schlemm's canal. The distal portion of the cannula may include a cutting portion configured to cut through the trabecular meshwork and the wall of Schlemm's canal, such as by providing distal end 134 with a sharp edge adapted to cut through such tissue.

Figure 7:
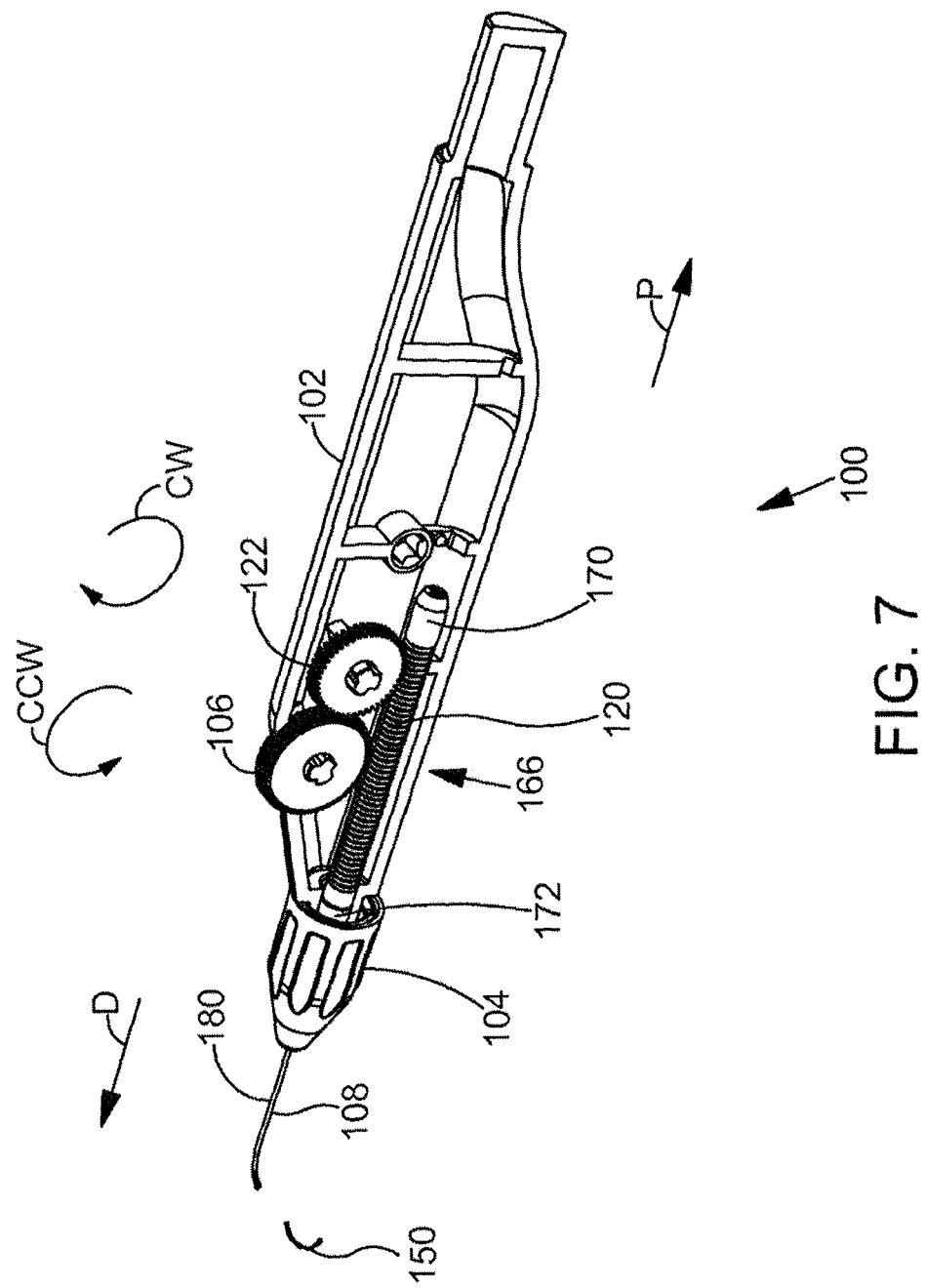
FIG. 7 is a perspective view further illustrating delivery system 100 shown in FIG. 6.

FIG. 7 is a perspective view further illustrating delivery system 100 shown in the previous figure. In FIG. 7, a portion of housing 102 has been removed for purposes of illustration. Delivery system 100 includes a delivery tool subassembly 170 and a cannula subassembly 180. Delivery tool subassembly 170 includes rotating rack gear 120 and a delivery tool (not shown). In the embodiment of FIG. 7, the delivery tool extends into a passageway defined by a cannula 108. Cannula 108 can be seen extending beyond sleeve 104 in FIG. 7. Cannula subassembly 180 includes cannula 108, a hub 172, and an extension tube (not shown). In the embodiment of FIG. 7, the extension tube of cannula subassembly 180 is disposed inside a lumen defined by rotating rack gear 120.

Delivery system 100 includes a mechanism 166 that controls the movement of delivery tool subassembly 170. Mechanism 166 includes a number of components that are located inside housing 102, including tracking wheel 106, an idler gear 122, and the rotating rack gear 120. In the embodiment of FIG. 7, tracking wheel 106 and idler gear 122 are both rotatably supported by housing 102. Gear teeth on tracking wheel 106 engage gear teeth on idler gear 122, which in turn engage gear teeth on the rotating rack gear 120. Rotating tracking wheel 106 in a counter clockwise direction CCW causes idler gear 122 to rotate in a clockwise direction CW, which in turn causes the rotating rack gear 120 to move in a distal direction D. Rotating tracking wheel 106 in a clockwise direction CW causes idler gear 122 to rotate in a counter clockwise direction CCW, which in turn causes the rotating rack gear 120 to move in a proximal direction P. In other embodiments, the idler gear may be eliminated from the device, which would cause counter-clockwise movement of the tracking wheel to move the rack gear proximally.

In the embodiment of FIG. 7, a sleeve 104 is fixed to cannula subassembly 180. Sleeve 104 may be rotated by the user to change the orientation of cannula 108 with respect to housing 102. The sleeve 104 may include gripping features, such as grooves (as shown), a rubber coating, or other frictional surfaces to facilitate this use. In some applications, correct alignment between the cannula and iris is advantageous to ensure that the core tube and/or ocular implant is advanced at the correct trajectory relative to Schlemm's canal or other anatomy in the eye into which the ocular implant is to be implanted. The device is configured in a manner that keeps the ocular implant aligned within the device during rotation. Selected groups of components are keyed together to ensure that they rotate as a single body while simultaneously allowing axial movement of the ocular implant. In the embodiment of FIG. 7, cannula subassembly 180 and delivery tool subassembly 170 rotate in unison with sleeve 104 relative to housing 102.

In the embodiment of FIG. 7, rotating rack gear 120 is configured to rotate with sleeve 104 while maintaining the ability to move axially in the distal and proximal directions before, during, and after rotation. As the rotating rack gear 120 moves distally and/or proximally, it causes corresponding movement of the delivery tool relative to cannula 108. This movement is transferred to ocular implant 150 when delivery tool 152 is coupled to ocular implant 150. Delivery tool subassembly 170 and cannula subassembly 180 engage one another in a keyed arrangement, as described in more detail below. This keyed arrangement causes delivery tool subassembly 170 and cannula subassembly 180 to maintain a constant rotational orientation relative to each other while, at the same time, allowing delivery tool subassembly 170 to translate in a distal direction D and a proximal direction P relative to cannula subassembly 180.

Figure 8:
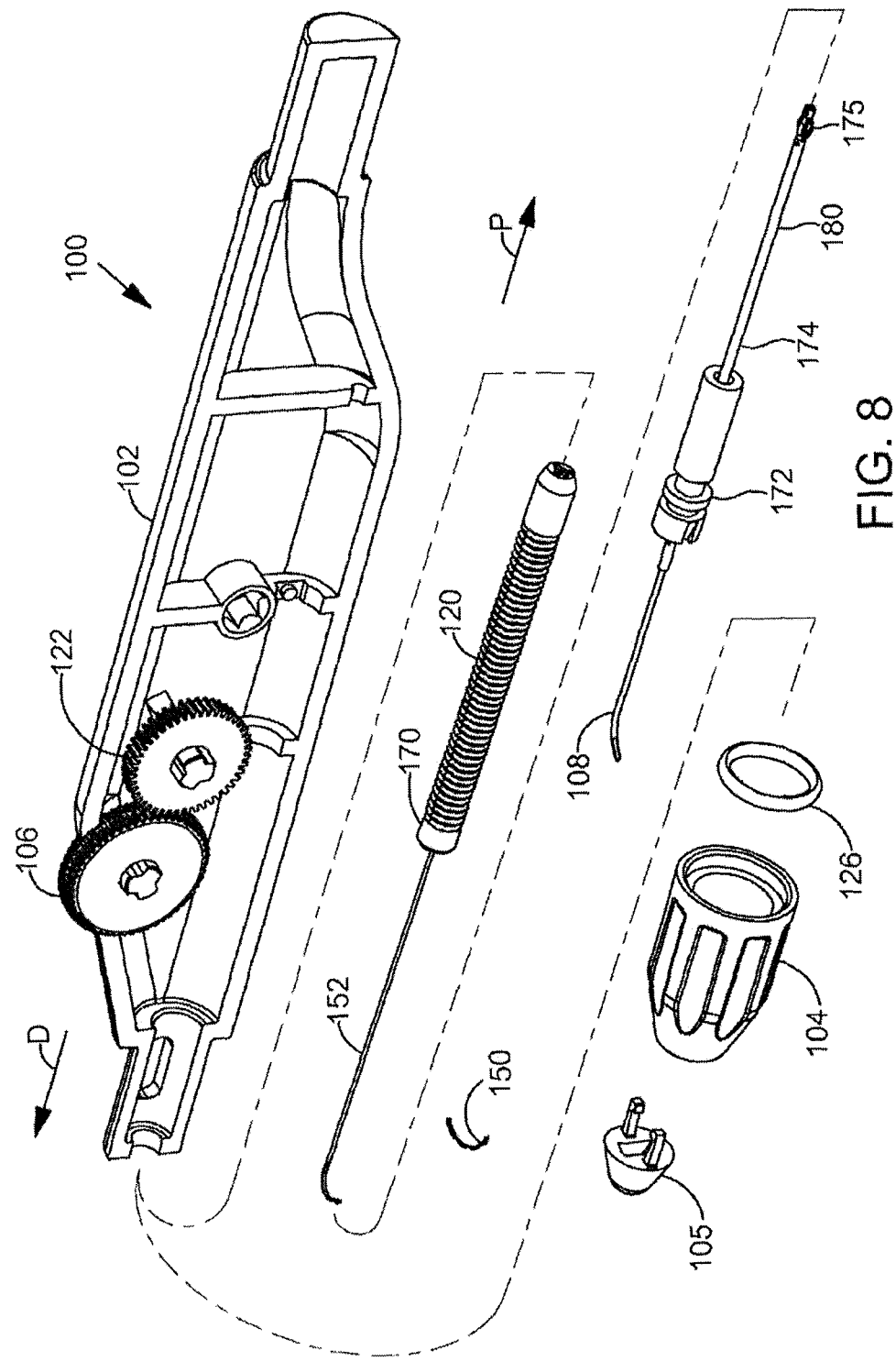
FIG. 8 is an exploded view illustrating various elements of a delivery system in accordance with the detailed description.

FIG. 8 is an exploded view illustrating various elements of delivery system 100. Cannula subassembly 180 includes a hub 172 and an extension tube 174 that are both fixed to cannula 108. Extension tube 174 includes a shaped portion 175 that is dimensioned and shaped to fit within a shaped through hole 177 (shown in FIGS. 8A and 11) by rotating rack gear 120. This keyed arrangement causes delivery tool subassembly 170 and cannula subassembly 180 to maintain a constant rotational orientation relative to each other while, at the same time, allowing delivery tool subassembly 170 to translate in a distal direction D and a proximal direction P relative to cannula subassembly 180.

In some embodiments, delivery tool 152 is formed from shape memory material (such as, e.g., nitinol), and at least a portion of delivery tool 152 assumes a curved at-rest shape when no external forces are acting on it. Delivery tool 152 can be urged to assume a straightened shape, for example, by inserting delivery tool 152 through a straight portion of the passageway defined by cannula 108. When the delivery tool is confined, such as within cannula 108, the interlocking portion can engage the complementary interlocking portion to join the delivery tool and ocular implant together, and allow the delivery tool and ocular implant to move together through the cannula 108, as described in more detail below.

Delivery system 100 also includes an O-ring 126 disposed between sleeve 104 and housing 102. O-ring 126 can provide friction and/or resistance between sleeve 104 and housing 102. This friction and/or resistance may be useful, for example, to hold the sleeve 104 in a desired orientation. A noseplug 105 snaps into the distal end of the delivery system.

Figure 9:
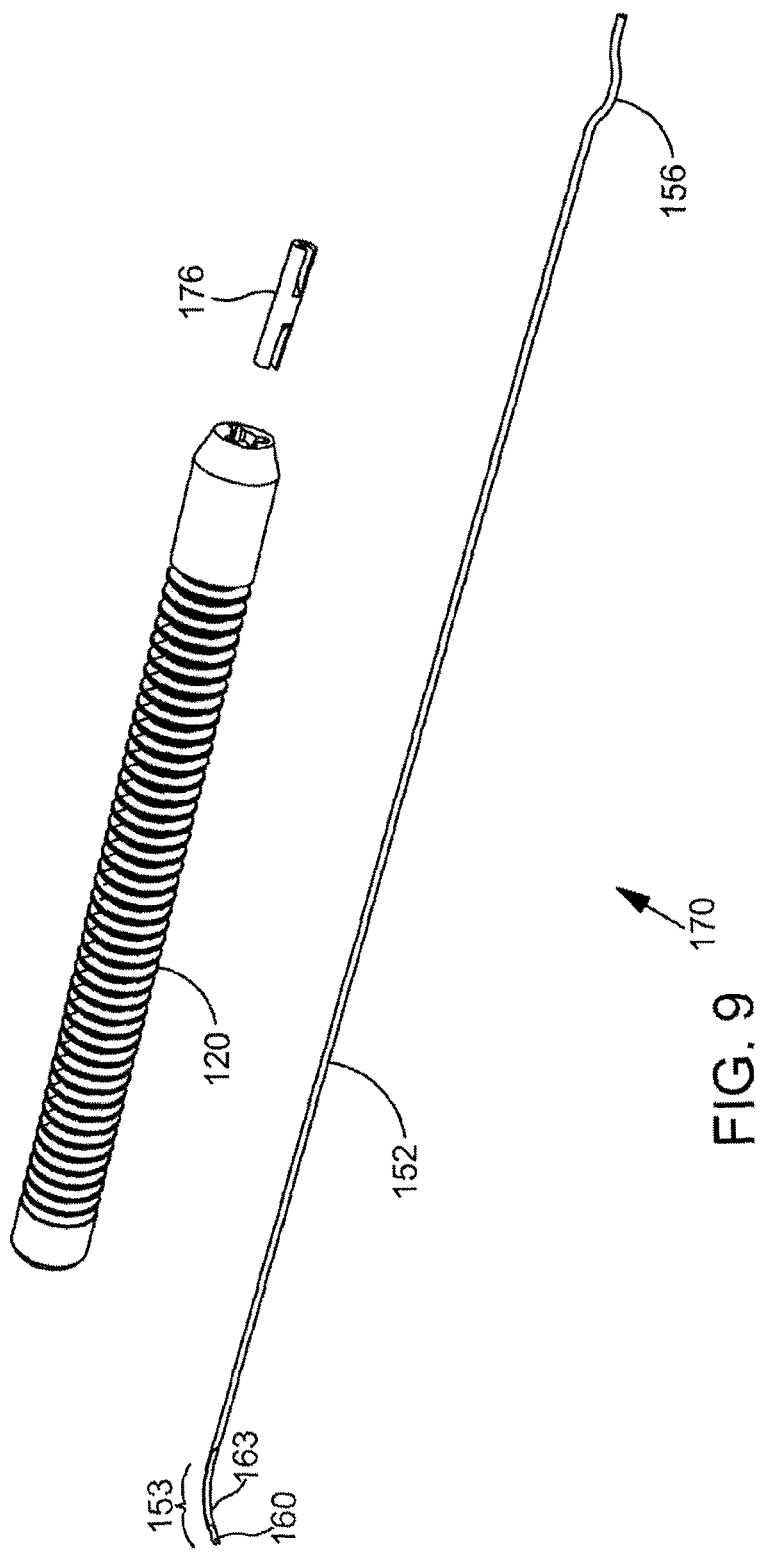
FIG. 9 is an exploded perspective view further illustrating the delivery tool subassembly shown in the exploded perspective view of FIG. 8.
Figure 11:
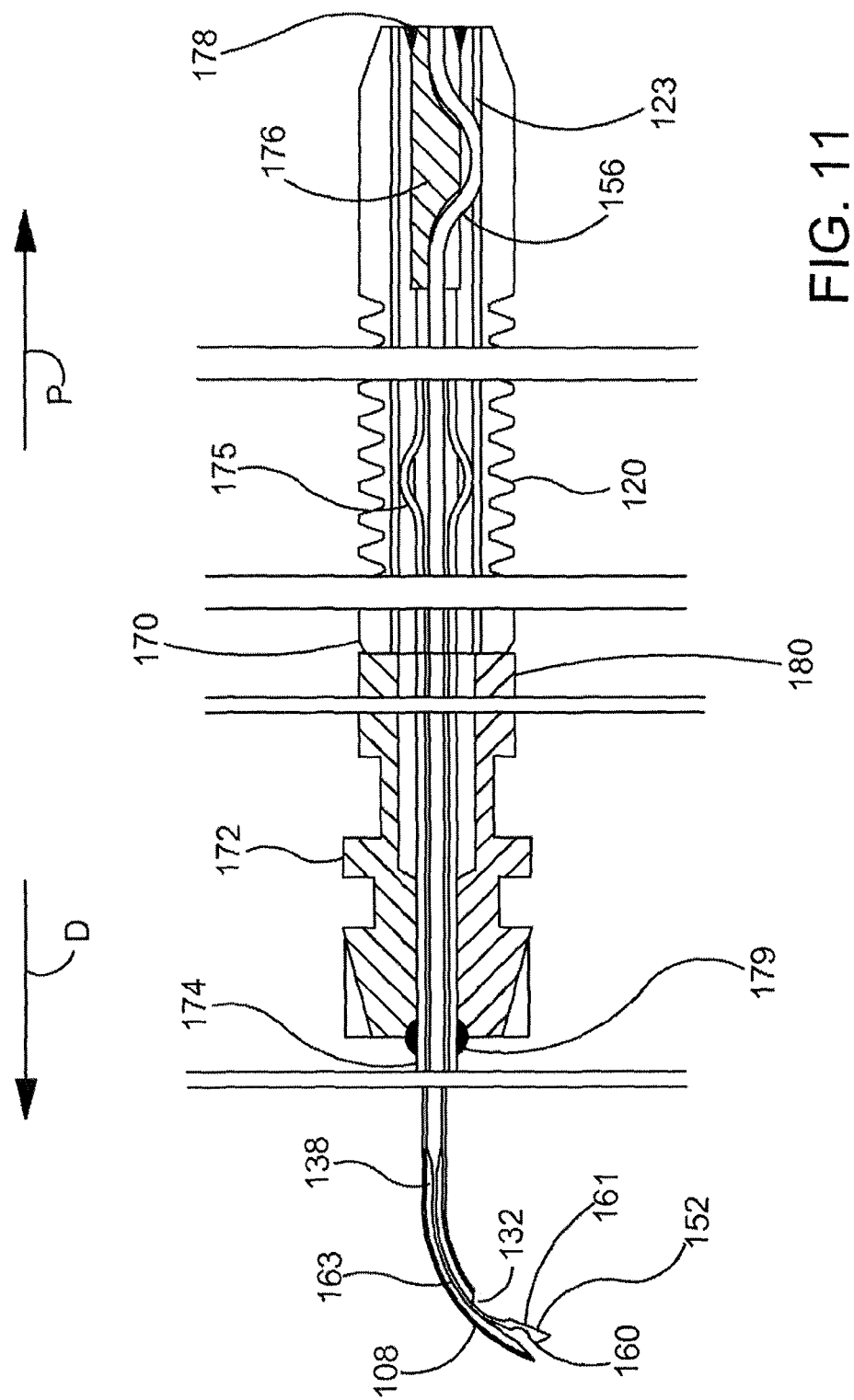
FIG. 11 is a cross-sectional view showing an assembly including both the delivery tool subassembly and the cannula subassembly shown in the exploded perspective view of FIG. 8.

FIG. 9 is an exploded perspective view of delivery tool subassembly 170 shown in the previous figure. Delivery tool subassembly 170 comprises a delivery tool 152, a rotating rack gear 120, and a spacer 176. Delivery tool 152 includes a shaped proximal portion 156, a curved distal portion 153, a distal cannula engagement surface 161 and a reduced diameter portion 163 proximal to the distal cannula engagement surface 161. Spacer 176 is interposed between rotating rack gear 120 and shaped proximal portion 156 of delivery tool 152 to hold delivery tool 152 and rotating rack gear 120 in a generally co-axial arrangement when delivery tool subassembly 170 is in an assembled state, as shown in FIG. 11. Distal cannula engagement surface 161 is adapted to slide along an inside surface of the cannula wall while the delivery tool 152 is engaged to ocular implant 150. Curved distal portion 153 of delivery tool 152 has an at rest curve that is greater (i.e., has a smaller radius of curvature) than the curved portion 144 of cannula 108.

Figure 10:
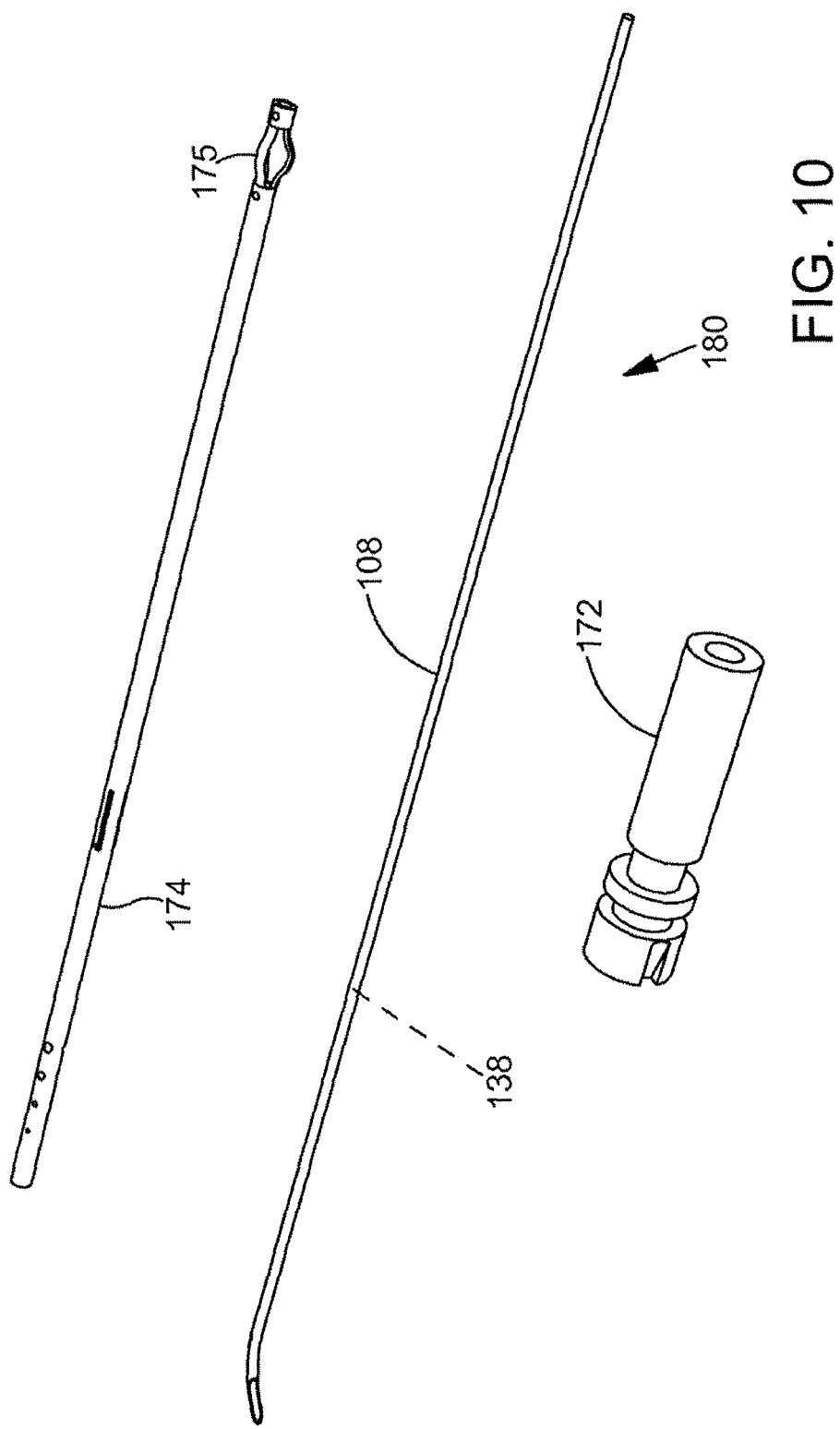
FIG. 10 is an exploded perspective view further illustrating the cannula subassembly shown in the exploded perspective view of FIG. 8.

FIG. 10 is an exploded perspective view of cannula subassembly 180. Cannula subassembly 180 comprises cannula 108, extension tube 174 and hub 172. In the embodiment of FIG. 10, cannula 108 defines a passageway 138 that is dimensioned to slidingly receive an ocular implant and the delivery tool shown in the previous figure. At the same time, extension tube 174 of cannula subassembly 180 may be received inside a lumen defined by the rotating rack gear shown in the previous figure.

Extension tube 174 includes a shaped portion 175 that is dimensioned and shaped to fit within a shaped through hole defined by rotating rack gear 120, as shown below in FIG. 11. This keyed arrangement causes delivery tool subassembly 170 and cannula subassembly 180 to maintain a constant rotational orientation relative to each other while, at the same time, allowing delivery tool subassembly 170 to translate in a distal direction D and a proximal direction P relative to cannula subassembly 180.

Figure 8A:
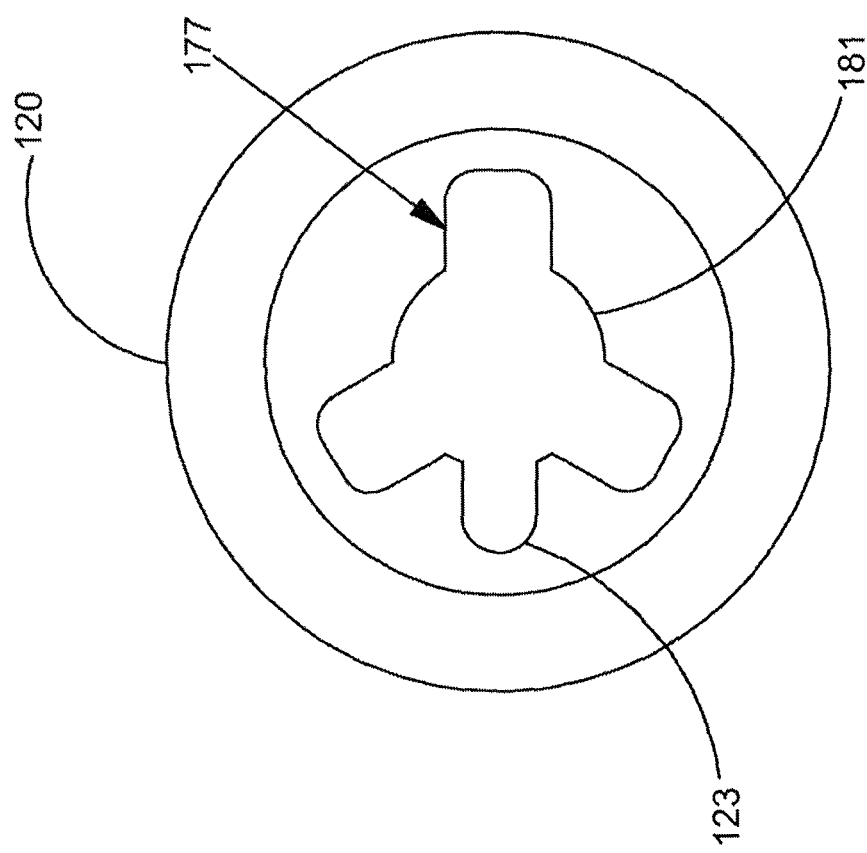
FIG. 8A is an end view of the rotating rack gear shown in FIG. 8.

FIG. 11 is a cross-sectional view showing an assembly including delivery tool subassembly 170 and cannula subassembly 180 discussed above. Delivery tool subassembly 170 includes a delivery tool 152, a rotating rack gear 120 and a spacer 176. In the cross-sectional view of FIG. 11, a shaped portion 156 of delivery tool 152 can be seen extending into a slot 123 extending from a central portion 181 through hole 177 formed in rotating rack gear 120. (FIG. 8A shows an end view of rotating rack gear 120 and through hole 177.) In the embodiment of FIG. 11, an interlocking portion 160 of delivery tool 152 is disposed in angular alignment with shaped portion 156. Spacer 176 is interposed between rotating rack gear 120 and delivery tool 152. In the exemplary embodiment of FIG. 11, spacer 176 is shaped and dimensioned to hold delivery tool 152 and rotating rack gear in a generally co-axial arrangement. This arrangement creates an advantageous oriented relationship of interlocking portion 160 with respect to the distal opening 132 of cannula 108 and ensures that interlocking portion 160 is unimpeded and readily disengages itself from the implant when it exits and flexes through distal opening 132. In the exemplary embodiment of FIG. 11, spacer 176 and rotating rack gear 120 are fixed to each other at a weld joint 178. Weld joint 178 may be formed, for example, using a laser welding process.

Cannula subassembly 180 includes cannula 108, a hub 172, and an extension tube 174. Extension tube 174 is disposed about cannula 108. Extension tube 174 and cannula 108 may be fixed to one another, for example, using a laser spot welding process. Hub 172 is fixed to an outer surface portion of extension tube 174 in the embodiment of FIG. 11 at a weld joint 179. Weld joint 179 may be formed, for example, using a laser welding process. In FIG. 11, extension tube 174 of cannula subassembly 180 can be seen extending into a shaped through-hole defined by rotating rack gear 120 of delivery tool assembly 170.

In FIG. 11, delivery tool 152 can be seen extending into a passageway 138 defined by a cannula 108 of cannula subassembly 180. Passageway 138 defined by cannula 108 is sized to slidably enclose delivery tool 152 and an ocular implant that is coupled to delivery tool 152. Delivery tool 152 is configured to form a connection with the ocular implant, so that distal movement of the delivery tool can cause distal movement of the ocular implant within cannula 108. Delivery tool 152 may be used to advance the ocular implant through a distal opening 132 of cannula 108 in order to deliver the ocular implant into the eye. The assembly of FIG. 11 may be rotated by the user to change the orientation of the curved portion of cannula 108 with respect to the housing of the delivery system. The keyed relationship between delivery tool subassembly 170 and cannula subassembly 180 assures that the rotational orientation between cannula 108 and the ocular implant/delivery tool stays constant while at the same time, allowing ocular implant/delivery tool to translate in a distal direction D and a proximal direction P relative to cannula 108.

Figure 12:
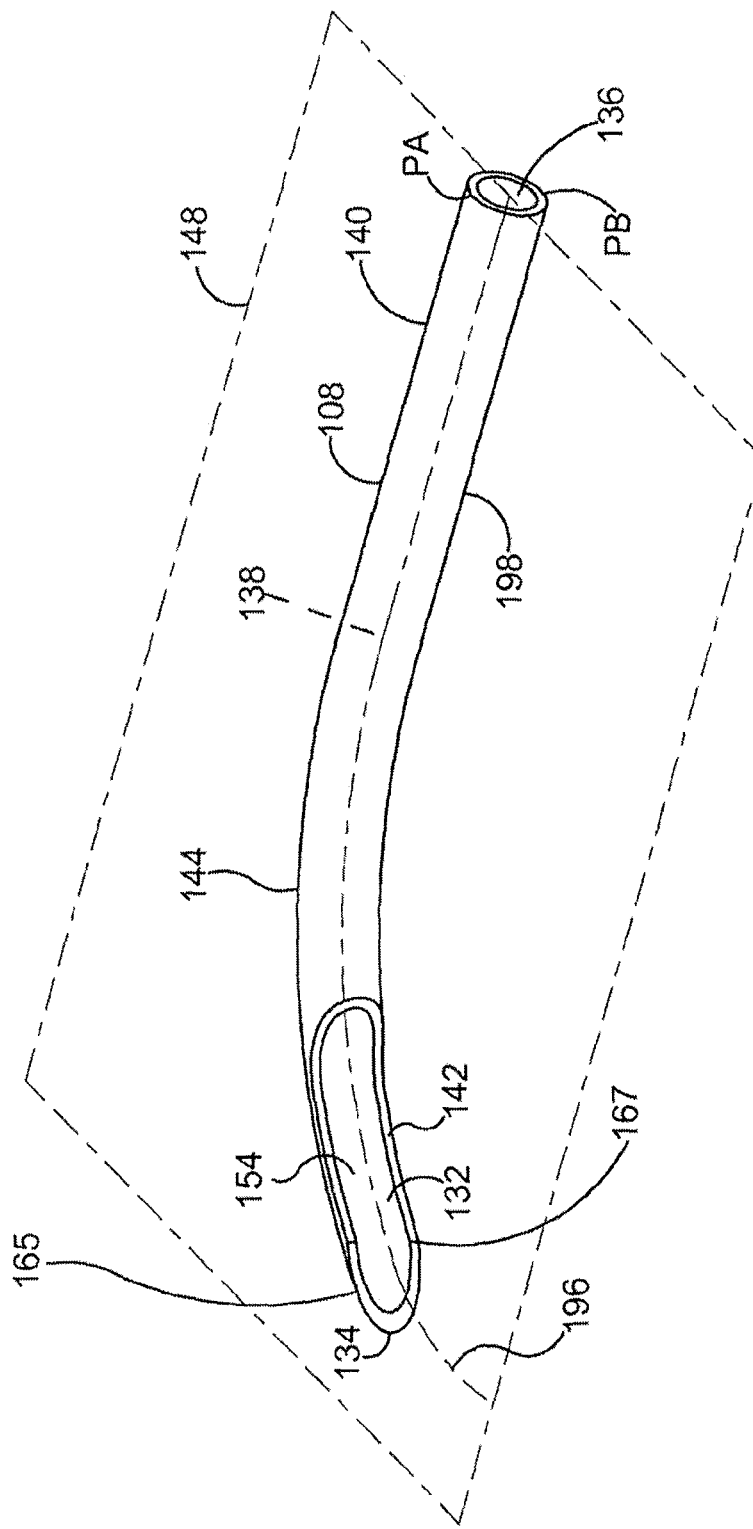
FIG. 12 is a perspective view of a cannula in accordance with the detailed description.

FIG. 12 is a perspective view of a cannula 108 in accordance with the present detailed description. Cannula 108 of FIG. 12 comprises a generally tubular member 198 having a central axis 196. Generally tubular member 198 of FIG. 12 comprises a proximal portion 140, a distal end 134, and a distal portion 144 extending between distal end 134 and proximal portion 140. A distal opening surface 142 surrounds a distal opening 132 extending through the distal end 134 and through a side wall of cannula 108. A beveled edge 165 is disposed at the distal end of distal opening surface 142, extending from the distal end 134 to a proximal extent 167 of beveled edge 165. Tubular member 198 defines distal opening 132, a proximal opening 136, and a passageway 138 extending between proximal opening 136 and distal opening 132.

In the embodiment of FIG. 12, proximal portion 140 of cannula 108 is substantially straight, distal portion 144 of cannula 108 is curved, and central axis 196 defines a curvature plane 148. Curvature plane 148 may be referred to as a plane of curvature. Curvature plane 148 divides cannula 108 into a first portion PA and a second portion PB. In the embodiment of FIG. 12, second portion PB is substantially a mirror image of first portion PA. In FIG. 12, distal portion 144 is shown extending between distal end 134 and proximal portion 140 with no intervening elements. In the embodiment of FIG. 12, distal portion 144 is curved along its entire length.

A method in accordance with this detailed description may include the step of advancing the distal end 134 of cannula 108 through the cornea of a human eye so that distal end 134 is disposed in the anterior chamber of the eye. Cannula 108 may then be used to access Schlemm's canal of the eye, for example, by piercing the wall of Schlemm's canal with the distal end 134 of cannula 108. The beveled edge 165 may be inserted into Schlemm's canal to place at least part of distal opening 132 of cannula 108 in communication with Schlemm's canal, as discussed in more detail below. The ocular implant may be advanced out of a distal port of the cannula and into Schlemm's canal.

In the embodiment of FIG. 12, distal portion 144 of cannula 108 defines a trough 154. In some useful embodiments, trough 154 is configured to receive the entire external cross section of an ocular implant as the ocular implant is being advanced into Schlemm's canal. When this is the case, trough 154 may have a depth dimension that is deeper than a width of the ocular implant. This cannula configuration advantageously prevents the ocular implant from intersecting the layers of the trabecular meshwork as the ocular implant is advanced into Schlemm's canal. Trough 154 may also be configured to allow the proximal portion of the ocular implant to be released from the delivery tool, as discussed below.

Figure 13:
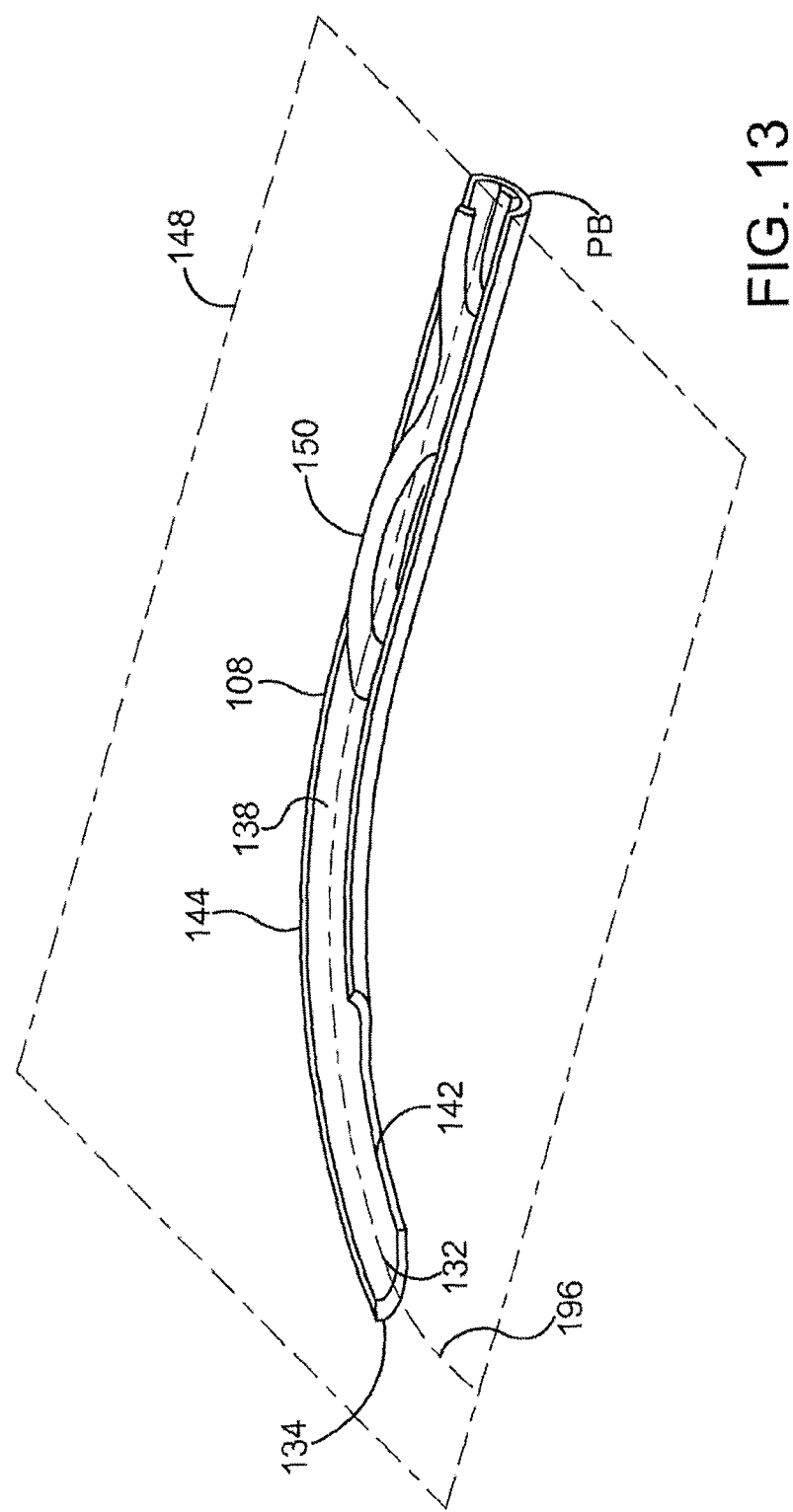
FIG. 13 is a perspective view of an assembly including the cannula shown in FIG. 12 and an ocular implant that is resting in a passageway defined by the cannula.

FIG. 13 is a perspective view of an assembly including cannula 108 shown in the previous figure. For purposes of illustration, cannula 108 is cross-sectionally illustrated in FIG. 13. In FIG. 13, an ocular implant 150 can be seen resting in a passageway 138 defined by cannula 108. With reference to FIG. 13, it will be appreciated that distal portion 144 of cannula 108 is curved so that central axis 196 of cannula 108 defines a curvature plane 148. With reference to FIG. 13, it will be appreciated that curvature plane 148 divides cannula 108 into a first portion and a second portion PB. Only second portion PB of cannula 108 is shown in the illustrative embodiment of FIG. 13.

Figure 14:
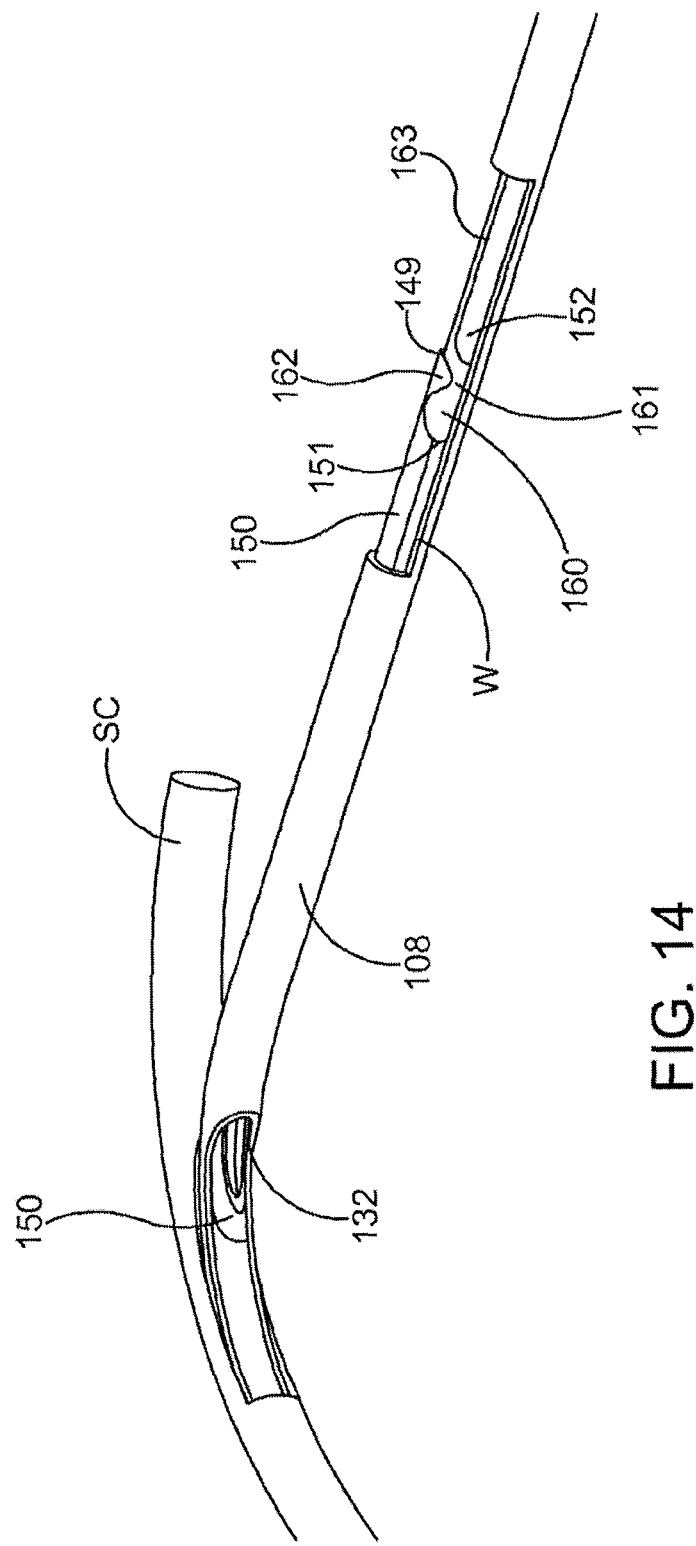
FIG. 14 is a stylized perspective view including the assembly shown in FIG. 13.

FIG. 14 is a stylized perspective view including the assembly shown in the previous figure. In the embodiment of FIG. 14, a distal portion of cannula 108 is shown extending through the wall of Schlemm's canal SC. The distal tip of cannula 108 may include a sharp portion configured for cutting and/or piercing the trabecular meshwork and the wall of Schlemm's canal so that the passageway defined by the cannula can be placed in fluid communication with the lumen defined by Schlemm's canal. With the passageway of the cannula placed in fluid communication with the lumen of Schlemm's canal, ocular implant 150 can be advanced out of the distal opening of the cannula and into Schlemm's canal. In FIG. 14, a distal portion of ocular implant 150 can be seen through distal opening 132 of cannula 108.

For purposes of illustration, a hypothetical window W is cut through the wall of cannula 108 in FIG. 14. An interlocking portion 160 of a delivery tool 152 and a complementary interlocking portion 162 of ocular implant 150 are visible through window W. In the embodiment of FIG. 14, interlocking portion 160 of delivery tool 152 and complementary interlocking portion 162 of ocular implant 150 are engaging each other so that a proximal end 149 of ocular implant 150 is proximal to the distal end 151 of delivery tool 152. Surface 161 of delivery tool 152 rests against the wall of cannula 108 to prevent interlocking portion 160 of delivery tool 152 and complementary interlocking portion 162 of ocular implant 150 from disengaging one another. When they are connected in this fashion, delivery tool 152 and ocular implant 150 move together as the delivery tool is advanced and retracted relative to cannula 108 by the delivery system mechanism.

Figure 15:
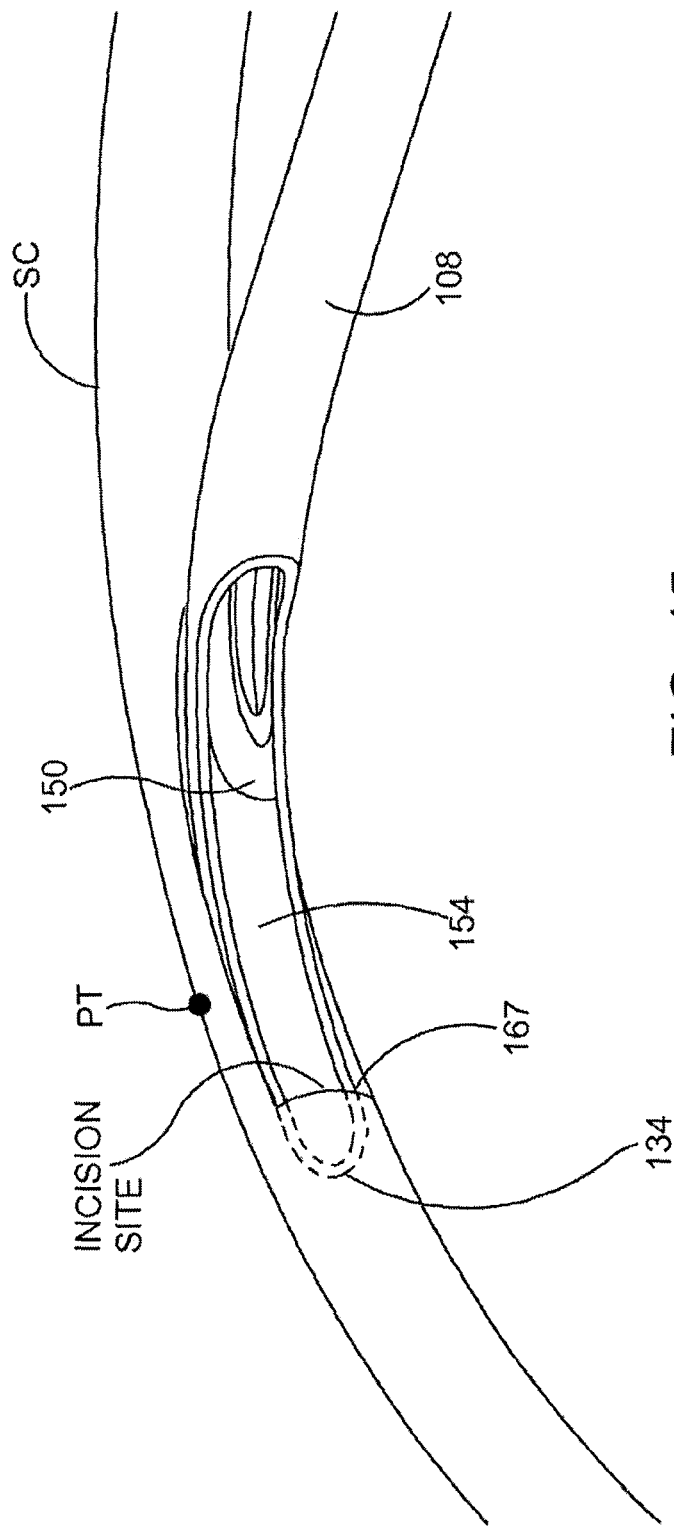
FIG. 15 is an enlarged perspective view showing a portion of the cannula shown in the assembly of FIG. 14.

FIG. 15 is an enlarged perspective view showing a portion of cannula 108 shown in the previous figure. In some useful embodiments, cannula 108 is curved to achieve substantially tangential entry into Schlemm's canal SC. In the embodiment of FIG. 15, cannula 108 is contacting an outer major wall of Schlemm's canal SC at a point of tangency PT. Also in the embodiment of FIG. 15, a curved distal portion of cannula 108 is dimensioned to be disposed within the anterior chamber of the eye.

As shown in FIG. 15, the distal tip 134 and beveled edge of the cannula 108 have been inserted into Schlemm's canal up to the proximal extent 167 of beveled edge 165. In this position, ocular implant 150 can be seen extending into trough 154. In some useful embodiments, the ocular implant has a radius of curvature that is larger than the radius of curvature of the cannula. This arrangement ensures that the ocular implant will track along trough 154 as the ocular implant is urged in a distal direction by delivery system 100.

Figure 16:
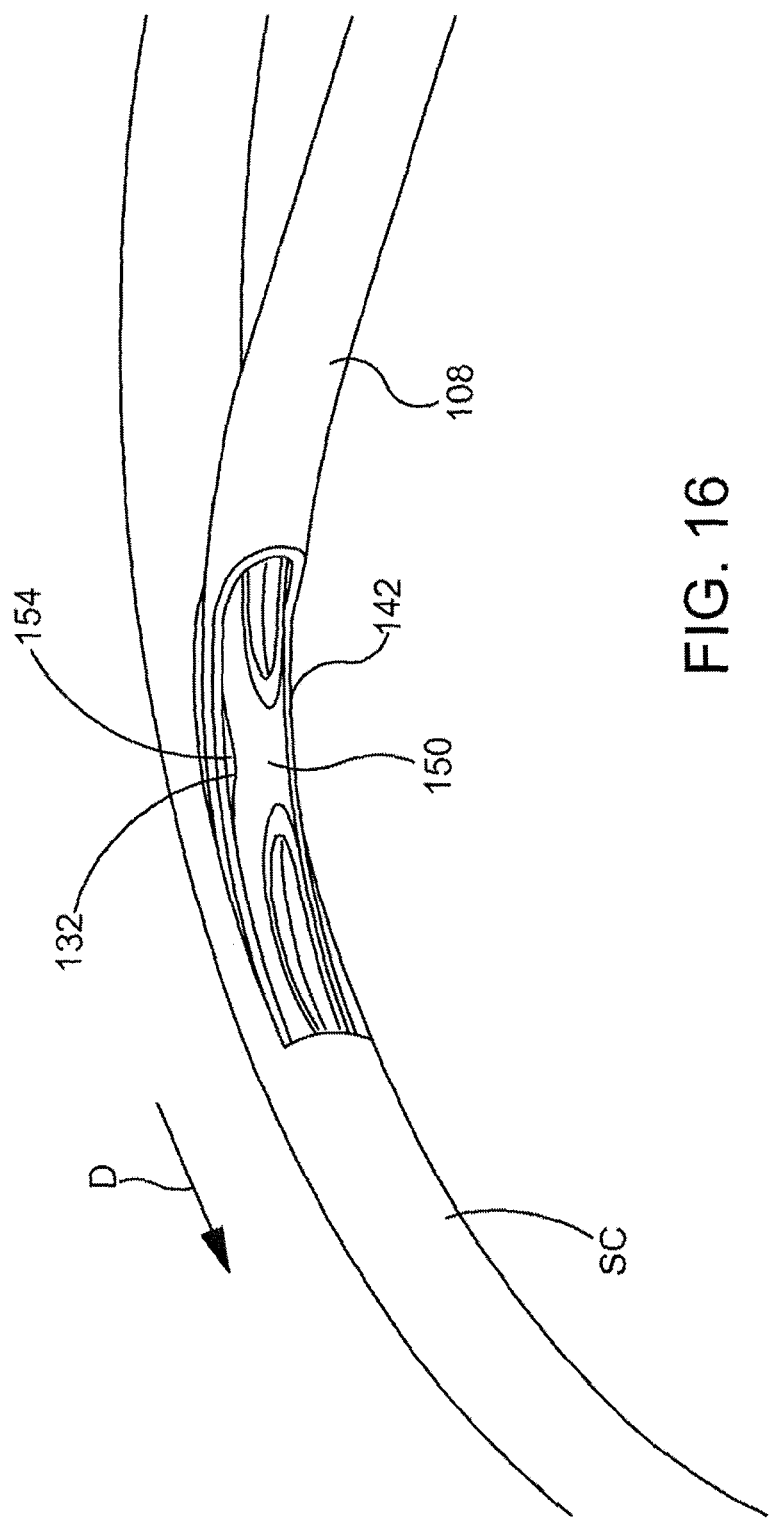
FIG. 16 is an additional perspective view showing the ocular implant and the cannula shown in the previous FIG. 15.

FIG. 16 is an additional perspective view showing ocular implant 150 and cannula 108 shown in the previous figure. By comparing FIG. 16 with the previous figure, it will be appreciated that ocular implant 150 has been advanced in a distal direction D while cannula 108 has remained stationary so that a distal portion of ocular implant 150 is disposed inside Schlemm's canal SC. Trough 154 opens into an elongate opening 132 defined by edge 142 at the distal portion of cannula 108. In the embodiment of FIG. 16, the elongate opening defined by the cannula provides direct visualization of the ocular implant as it is advanced into Schlemm's canal. A configuration allowing direct visualization of the ocular implant has a number of clinical advantages. During a medical procedure, it is often difficult to monitor the progress of the implant by viewing the implant through the trabecular meshwork. For example, blood reflux may push blood into Schlemm's canal obstructing a physician's view the portion of the implant that has entered Schlemm's canal. With reference to FIG. 16, ocular implant 150 tracks along trough 154 as it is advanced distally along cannula 108. The trough opening allows the physician to monitor the progress of the implant by viewing the implant structures as they advance through the trough prior to entering Schlemm's canal. The trough opening also allows the physician to identify the position of the proximal end of the ocular implant with respect to the incision made by the cannula to access Schlemm's canal.

Figure 17:
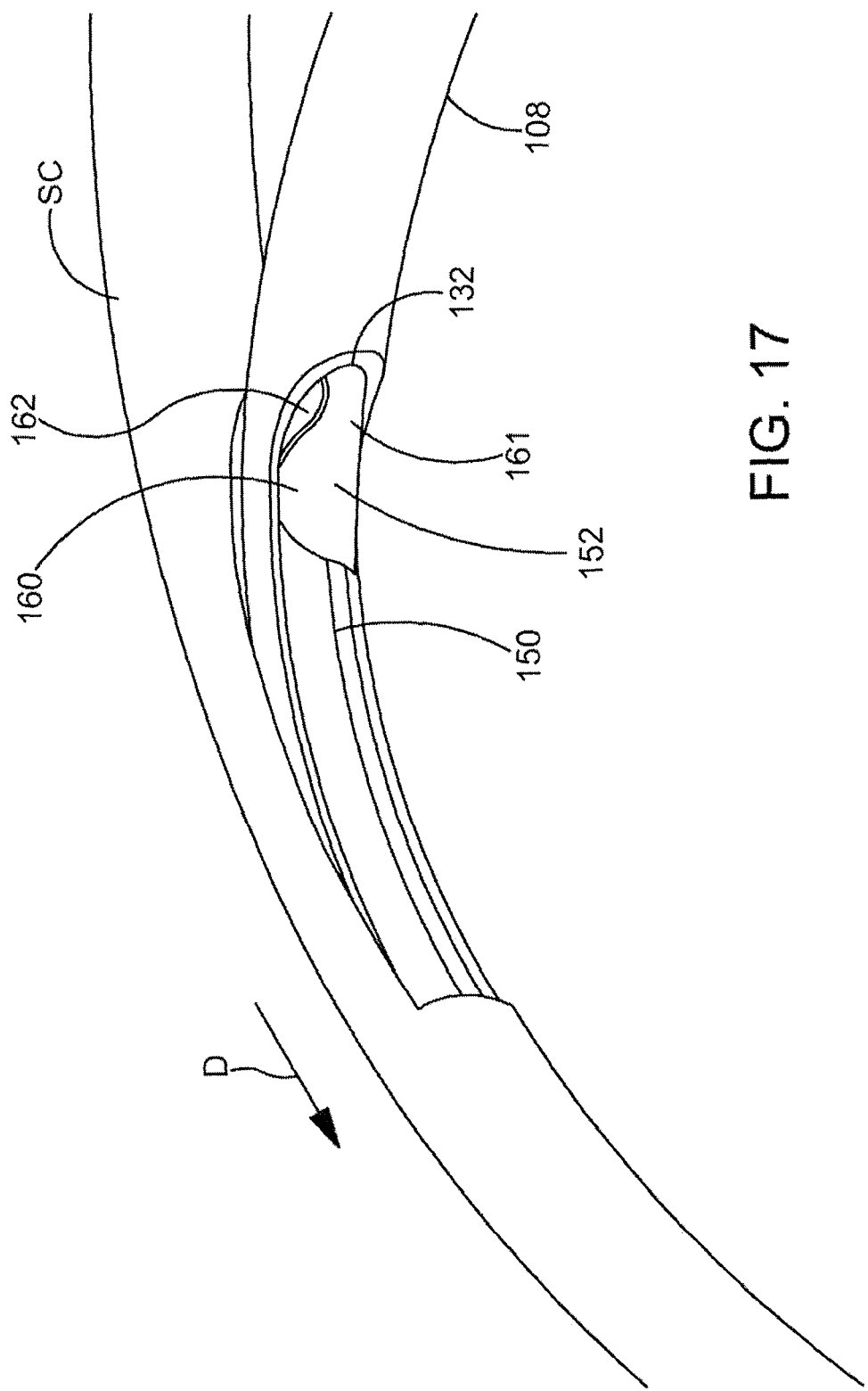
FIG. 17 is an additional perspective view showing the ocular implant and the cannula shown in FIG. 16.

FIG. 17 is an additional stylized perspective view showing ocular implant 150 and cannula 108. In the embodiment of FIG. 17, the interlocking portions 160 and 162 of the delivery tool 152 and ocular implant 150, respectively, can be seen entering the distal opening 132 defined by cannula 108. As shown, ocular implant 150 has been advanced in a distal direction D (relative to the embodiment shown in the previous figure) so that more of ocular implant 150 is disposed inside Schlemm's canal SC. Surface 161 opposite interlocking portion 160 of delivery tool 152 still rests against the inner wall of cannula 108 to keep the delivery tool interlocked with ocular implant 150.

Figure 18:
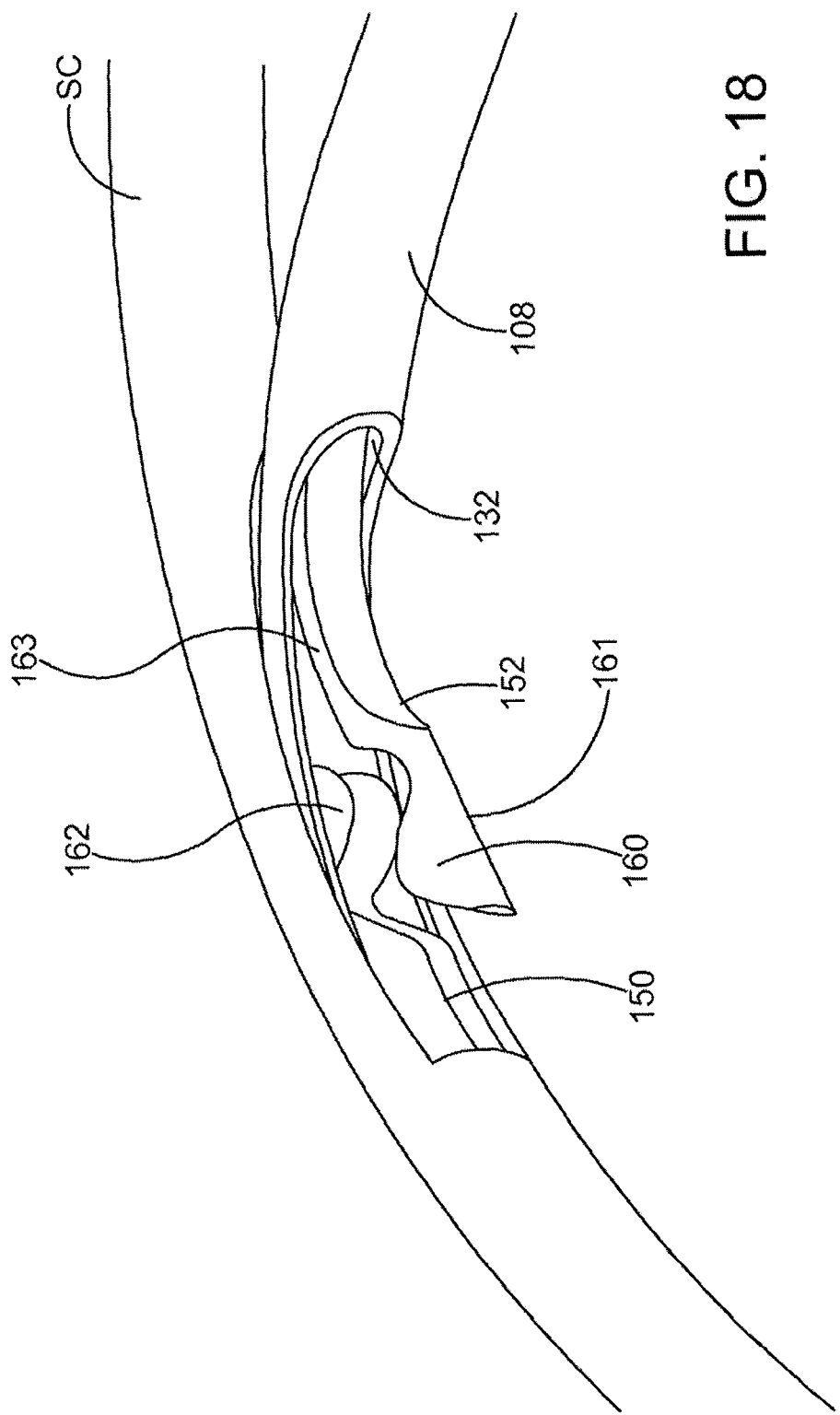
FIG. 18 is an additional perspective view showing the ocular implant and the cannula shown in FIGS. 16 and 17.

FIG. 18 is an additional stylized perspective view showing ocular implant 150 and cannula 108. As shown in FIG. 18, the ocular implant 150 and delivery tool 152 have advanced further distally so that delivery tool surface 161 and part of the reduced diameter portion 163 have now passed into opening 132, thereby permitting the delivery tool curved portion 153 to move toward its curved at-rest shape so that the delivery tool engagement surface 160 disengages and moves away from its complementary engagement surface 162 on the ocular implant 150.

In some useful embodiments, the delivery tool may be colored to provide visual differentiation from the implant. After the disengaging from the ocular implant, cannula 108 and delivery tool 152 can be withdrawn from Schlemm's canal SC leaving the ocular implant 150 in the fully deployed position shown in FIG. 18. After delivery of ocular implant 150 is complete, the delivery tool and the cannula may be removed from the eye, leaving at least a distal portion of the ocular implant in Schlemm's canal.

FIG. 19 is a perspective view of Schlemm's canal SC after the cannula (seen in the previous figure) has been withdrawn leaving an inlet portion of ocular implant 150 in the anterior chamber of the eye and the remainder of ocular implant 150 in Schlemm's canal. The presence of ocular implant 150 in Schlemm's canal may facilitate the flow of aqueous humor out of the anterior chamber. This flow may include axial flow along Schlemm's canal, flow from the anterior chamber into Schlemm's canal, and flow leaving Schlemm's canal via outlets communicating with Schlemm's canal. When in place within the eye, ocular implant 150 will support the trabecular meshwork and Schlemm's canal tissue and will provide for improved communication between the anterior chamber and Schlemm's canal (via the trabecular meshwork) and between pockets or compartments along Schlemm's canal.

Figure 20A:
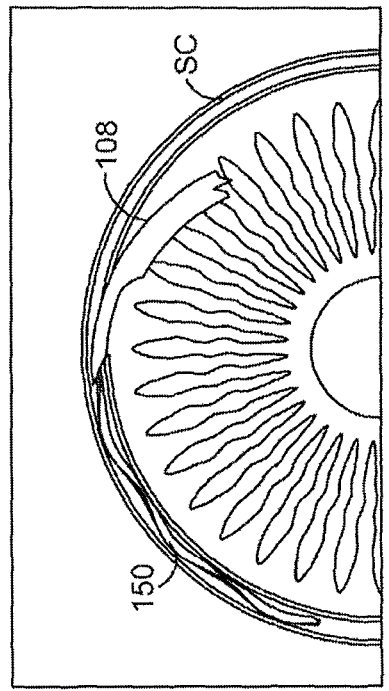

FIG. 20A-FIG. 20H are a series of stylized plan views illustrating example methods in accordance with this detailed description and associated apparatus used while performing those methods. In FIG. 20A, a distal portion of cannula 108 is shown extending through the wall of Schlemm's canal SC. In the embodiment of FIG. 20A, cannula 108 includes a sharp portion at its distal end 134 configured for cutting and/or piercing the trabecular meshwork and the wall of Schlemm's canal SC. In the embodiment of FIG. 20A, the distal end of cannula 108 has been advanced through the trabecular meshwork and the wall of Schlemm's canal SC and a passageway defined by cannula 108 has been placed in fluid communication with the lumen defined by Schlemm's canal SC.

Figure 20B:
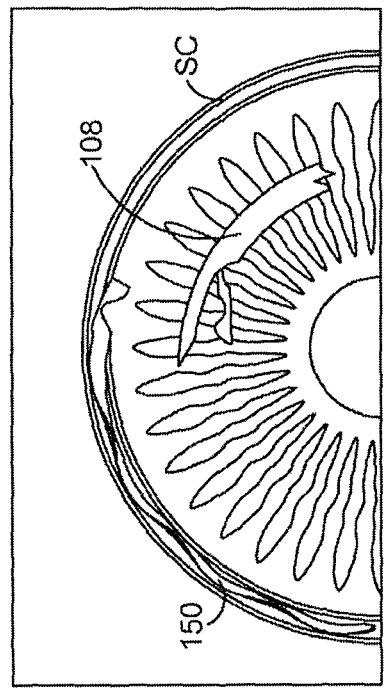

FIG. 20B is an additional stylized plan view showing cannula 108 shown in the previous figure. In the embodiment of FIG. 20B, an ocular implant 150 has been advanced out of a distal opening of cannula 108 and into Schlemm's canal SC. In FIG. 20B, a distal portion of ocular implant 150 is shown residing in a lumen defined by Schlemm's canal.

Figure 20C:
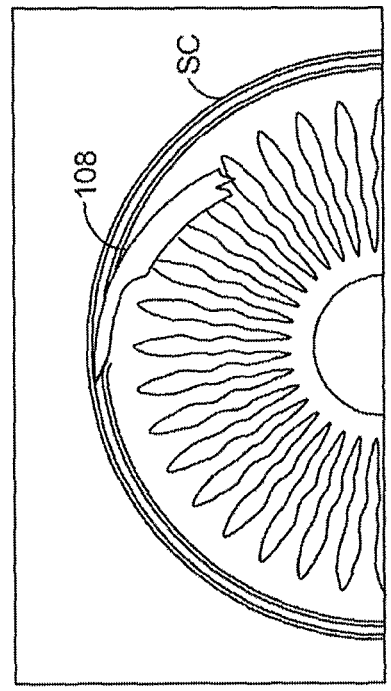

FIG. 20C is an additional stylized plan view showing ocular implant 150 and cannula 108. In the embodiment of FIG. 20C, an interlocking portion 160 of delivery tool 152 and complementary interlocking portion 162 of ocular implant 150 are both disposed near a trough portion of cannula 108. Ocular implant 150 has been advanced in a distal direction D (relative to the embodiment shown in the previous figure) so that more of ocular implant 150 is disposed inside Schlemm's canal SC. In FIG. 20C, ocular implant is shown residing in a fully deployed position. As shown in FIG. 20C, interlocking portion 160 of delivery tool 152 has disengaged from complementary interlocking portion 162 of ocular implant 150.

In the embodiment of FIG. 20C, distal opening 132 defined by cannula 108 is shaped and dimensioned so as to allow interlocking portion 160 of delivery tool 152 to extend therethrough when ocular implant 150 reaches the fully deployed position shown in FIG. 20C. When surface 161 has entered opening 132, a distal portion of delivery tool 152 is free to flex radially inward toward a curved, at-rest shape extending through distal opening 132 when ocular implant 150 reaches the fully deployed position shown in FIG. 20C to disengage from the ocular implant.

Figure 20D:
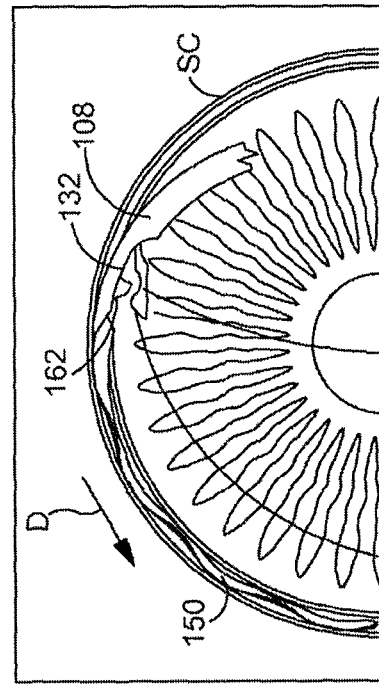

FIG. 20D is a plan view of Schlemm's canal SC after cannula 108 has been moved away from ocular implant 150. After moving cannula 108 away from ocular implant 150, a physician may visually inspect the present location of the ocular implant to determine whether that location is acceptable. If the physician determines that the present location is unacceptable, the physician may use the systems and methods described herein to recapture and reposition the ocular implant. The figures described below illustrate exemplary methods and apparatus for recapturing and repositioning the ocular implant.

In the embodiment of FIG. 20E, cannula 108 has been positioned so that the complementary interlocking portion 162 of ocular implant 150 is disposed between cannula 108 and the interlocking portion 160 of delivery tool 152. Further distal movement of cannula 108 will cause delivery tool surface 161 to re-engage with the inner wall of cannula 108, thereby moving the interlocking portion 160 of the delivery tool into re-engagement with the ocular implant. The delivery tool and ocular implant can thereafter be moved proximally, possibly together with the cannula, to reposition the implant for subsequent redeployment.

FIG. 20F is an additional stylized plan view showing ocular implant 150 and cannula 108 shown in the previous figure. By comparing FIG. 20F with the previous figure, it will be appreciated that delivery tool 152 and ocular implant 150 have been moved in a proximal direction P so that a portion of ocular implant 150 has been withdrawn from Schlemm's canal SC. In the embodiment of FIG. 20F, the complementary interlocking portion of ocular implant 150 and the interlocking portion of delivery tool 152 have both been drawn into the passageway defined by cannula 108. Also in the embodiment of FIG. 20F, the side wall of cannula 108 is holding the distal portion of delivery tool 152 in a deformed shape with the interlocking portion of delivery tool 152 engaging the complementary interlocking portion of ocular implant 150.

FIG. 20G is an additional stylized plan view showing ocular implant 150 and cannula 108 shown in the previous figure. In the embodiment of FIG. 20G, ocular implant 150 has been advanced out of a distal opening of cannula 108 and into Schlemm's canal SC. In FIG. 20G, a distal part of ocular implant 150 is shown residing in a lumen defined by Schlemm's canal. In the embodiment of FIG. 20G, interlocking portion 160 of delivery tool 152 and complementary interlocking portion 162 of ocular implant 150 are both once again located near a trough portion of cannula 108. In FIG. 20G, ocular implant is shown residing in a second fully deployed position. In the embodiment of FIG. 20G, the delivery tool 152 has once again disengaged from ocular implant 150 by permitting interlocking portion 160 of delivery tool 152 to move away from complementary interlocking portion 162 of ocular implant 150

FIG. 20H is a stylized plan view showing ocular implant 150 and Schlemm's canal SC after the cannula (seen in the previous figure) has been withdrawn leaving an inlet portion of ocular implant 150 in the anterior chamber of the eye and the remainder of ocular implant 150 in Schlemm's canal. When in place within the eye, ocular implant 150 will support the trabecular meshwork and Schlemm's canal tissue and will provide for improved communication between the anterior chamber and Schlemm's canal (via the trabecular meshwork) and between pockets or compartments along Schlemm's canal. Accordingly, the presence of ocular implant 150 in Schlemm's canal will facilitate the flow of aqueous humor out of the anterior chamber.

With reference to the figures described above, it will be appreciated that methods in accordance with the present detailed description may be used to position at least a distal portion of an implant in Schlemm's canal of an eye. In some cases, a proximal inlet portion of the ocular implant may be left in the anterior chamber. An exemplary method in accordance with the present detailed description may include the step of advancing a distal end of a cannula through a cornea of the eye so that a distal portion of the cannula is disposed in the anterior chamber of the eye. The cannula may be used to access Schlemm's canal, for example, by cutting and/or piercing the wall of Schlemm's canal with a distal portion of the cannula. A distal opening of the cannula may be placed in fluid communication with Schlemm's canal. The distal end of the ocular implant may be advanced through the distal opening of the cannula and into Schlemm's canal.

After delivering an ocular implant into Schlemm's canal, a physician may visually inspect the present location of the ocular implant to determine whether that location is acceptable. If the physician determines that the present location is unacceptable, the physician may use the systems and methods described herein to recapture and redeliver the ocular implant. Recapturing and redelivering the ocular implant may include the steps of forming a second connection between the delivery tool and the ocular implant and moving the delivery tool and the ocular implant in a proximal direction so that at least a portion of the ocular implant is withdrawn from Schlemm's canal. A distal part of the ocular implant may be advanced into Schlemm's canal while the ocular implant is coupled to the delivery tool at the second connection. The second connection may be selectively broken to release the ocular implant from the delivery system while the distal part of the ocular implant is disposed in Schlemm's canal.

FIG. 21 is a perspective view showing a delivery tool subassembly 370 that may be part of a delivery system (e.g., delivery system 100 shown in FIG. 8). Delivery tool subassembly 370 of FIG. 21 comprises a rotating rack gear 320 that is fixed to a delivery tool 352. Delivery tool 352 includes an interlocking portion 360 and a curved distal portion 353. Curved distal portion 353 of delivery tool 352 is biased to assume the curved at-rest shape shown in FIG. 21 when no external forces are acting on it. Curved distal portion 353 of delivery tool 352 may be urged to assume a straightened shape, for example, when it is disposed in a straight portion of a passageway defined by a cannula. Optional cut-outs 351 may be formed in the wall of delivery tool 352 to reduce friction during tool advancement by reducing the bending force. The cannula wall may also hold interlocking portion 360 of delivery tool 352 into engagement with a complementary interlocking portion of an ocular implant to form a mechanically interlocking connection.

FIG. 22A is a stylized plan view showing delivery tool 352 shown in the previous figure. In the embodiment of FIG. 22A, delivery tool 352 is extending into a passageway 338 defined by a cannula 308. A distal portion of cannula 308 defines a trough 354 that communicates with the passageway 338 defined by the wall of cannula 308. Trough 354 opens out the distal end of cannula 308. Trough 354 also opens into an elongate opening 332 defined by the edge 342 of the cannula wall.

In FIG. 22A, cannula 308 is illustrated in partial cross section. Interlocking portion 360 of delivery tool 352 and a complementary interlocking portion 362 of an ocular implant 350 are visible in FIG. 22A. In the embodiment of FIG. 22A, interlocking portion 360 of delivery tool 352 and complementary interlocking portion 362 of ocular implant 350 are engaging each other to form a mechanically interlocking connection such that the implant's interlocking portion 362 is proximal to the delivery tool's interlocking portion 360. The delivery tool 352 and ocular implant 350 may be selectively disengaged when interlocking portion 360 of delivery tool 352 is allowed to move away from and disengage complementary interlocking portion 362 of ocular implant 350. In the embodiment of FIG. 22, the wall of cannula 308 is preventing interlocking portion 360 of delivery tool 352 from moving away from and disengaging complementary interlocking portion 362 of ocular implant 350. A surface 363 of delivery tool 352 can be seen contacting the wall of cannula 308 at a point S in FIG. 22.

In FIG. 22A, interlocking portion 360 of delivery tool 352 is shown disposed within cannula passageway 338 at a location proximal of trough 354 and distal opening 332. In some useful embodiments, opening 332 is dimensioned and positioned such that, when the ocular implant reaches a predefined location along the passageway, the distal portion of delivery tool 352 will be free to move toward a curved at-rest shape. When the delivery tool assumes a curved shape, the interlocking portion of the delivery tool moves away from and disengages the complementary interlocking portion of the ocular implant. In this way, delivery tool 352 and ocular implant 350 may be selectively disengaged as delivery tool 352 is moved distally along the passageway defined by the cannula from a starting location proximal of opening 332.

FIG. 22B is an additional stylized plan view illustrating cannula 308, ocular implant 350, and delivery tool 352 shown in the previous figure. By comparing FIG. 22B with FIG. 22A, it will be appreciated that delivery tool 352 has been advanced in a distal direction D so that delivery tool 352 is extending through opening 332 and ocular implant 350 is outside of cannula passageway 338. In the embodiment of FIG. 22B, interlocking portion 360 has moved away from complementary interlocking portion 362 and ocular implant 350 and delivery tool 352 have disengaged.

In some instances, it may be desirable to deliver an ocular implant to Schlemm's canal in conjunction with another corrective surgery, such as, but not limited to, cataract surgery. When the ocular implant is placed during another surgical procedure, it may be desirable to insert the ocular implant through the same incision used for the other procedure. FIG. 23A is a perspective view showing another illustrative delivery system 400 that may be used to advance ocular implant 450 into a target location in the eye of a patient through an incision location created for another procedure, such as, but not limited to cataract surgery. The delivery system 400 may include an ocular implant 450 and a cannula 408 defining a passageway that is dimensioned to slidingly receive ocular implant 450. It is contemplated that aspects of delivery system 400 may be similar in form and function to delivery system 100. Examples of target locations that may be suitable in some applications include areas in and around Schlemm's canal, the trabecular meshwork, the suprachoroidal space, and the anterior chamber of the eye. FIG. 23B is an enlarged detail view further illustrating ocular implant 450 and cannula 408 of delivery system 400.

Delivery system 400 of FIG. 23A is capable of controlling the advancement and retraction of ocular implant 450 within cannula 408. Ocular implant 450 may be placed in a target location (e.g., Schlemm's canal) by advancing the ocular implant 450 through a distal opening 432 of cannula 408 while the distal opening is in fluid communication with Schlemm's canal. In the embodiment of FIG. 23A, ocular implant 450 has been advanced through distal opening 432 of cannula 408 for purposes of illustration.

Delivery system 400 of FIG. 23A includes a housing 402, a sleeve 404, and an end cap 410. A tracking wheel 406 extends through a wall of housing 402 in FIG. 23A. Tracking wheel 406 is part of a mechanism that is capable of advancing and retracting a delivery tool 452 of delivery system 400. The delivery tool 452 is slidably disposed within cannula 408 and configured to extend through a distal opening of cannula 408. Rotating the tracking wheel will cause delivery tool 452 to move in an axial direction along a passageway defined by cannula 408. The axial direction may be in a distal direction D or a proximal direction P. Delivery tool 452 may be similar in form and function to delivery tool 152.

In the embodiment of FIG. 23A, housing 402 is configured to be gripped with one hand while providing control over the axial advancement and retraction of ocular implant via tracking wheel 406. The features of housing 402 result in an advantageous ergonomic relationship of the fingers relative to the hand. This design provides a configuration that will allow a user, such as a physician, to stabilize the device using part of the hand, while leaving the middle or index finger free move independently from the remainder of the hand. The middle or index finger is free to move independently to rotate the wheel for advancing and/or retract the ocular implant.

FIG. 23B is an enlarged detail view further illustrating ocular implant 450 and a cannula 408 of delivery system 400. Cannula 408 comprises a generally tubular member 498 having proximal portion 440, an intermediate portion 445, a distal portion 444, and a distal end 434. The intermediate portion 445 may extend distally from a first point 443 distal to the proximal end 441 to a second point 447 proximal to the distal end 434. The distal portion 444 may extend between distally from the second point 447 to distal end 434 of cannula 408 (shown in FIG. 27). In the embodiment of FIG. 23, both distal portion 444 and intermediate portion 445 may be curved. In some instances, distal portion 444 may have a smaller radius of curvature, and thus a higher curvature, than the intermediate portion 445, although this is not required. In some useful embodiments, distal portion 444 and intermediate portion 445 may be dimensioned and configured to be received in the anterior chamber of the eye.

In some instances, it may be desirable to place the ocular implant 450 during another ocular procedure, such as, but not limited to cataract surgery. It is contemplated that the optimal position for an incision for cataract surgery may not be the same as the optimal position of an incision for solely placing an ocular implant, such as implant 450, into Schlemm's canal. With previous ocular implant delivery system designs, in order to allow for substantially tangential entry of the cannula into Schlemm's canal two separate incisions may be required when the implant is placed in combination with another ocular procedure. The curved configuration of both the distal portion 444 may be configured to allow for substantially tangential entry of the cannula 408 into Schlemm's canal. It is further contemplated that the curved configuration of the intermediate portion 445 may allow the cannula 408 to be advanced through typical incisions associated with and/or optimized for cataract surgery, such as, but not limited to, a sclerocorneal tunnel incision, while still allowing for substantially tangential entry of the cannula 408 into Schlemm's canal. This may allow for two or more ocular procedures to be performed using a single incision. It is further contemplated that performing multiple procedures through a single incision may reduce patient discomfort and recovery time.

FIG. 23B shows delivery tool 452 of delivery system 400 extending through distal opening 432 of cannula 408. Delivery tool 452 includes an interlocking portion 460 that is configured to form a connection with a complementary interlocking portion 462 of ocular implant 450, as explained in more detail below. In the embodiment of FIG. 23, rotating the tracking wheel will cause delivery tool 452 and ocular implant 450 to move along a path defined by cannula 408. Cannula 408 is sized and configured so that the distal end of cannula 408 can be advanced through the trabecular meshwork of the eye and into Schlemm's canal. Positioning cannula 408 in this way places distal opening 432 in fluid communication with Schlemm's canal. Ocular implant 450 may be placed in Schlemm's canal by advancing the ocular implant through distal opening 432 of cannula 408 while the distal opening is in fluid communication with Schlemm's canal. The distal portion of the cannula 408 may include a cutting portion configured to cut through the trabecular meshwork and the wall of Schlemm's canal, such as by providing distal end 434 with a sharp edge adapted to cut through such tissue.

Figure 24:
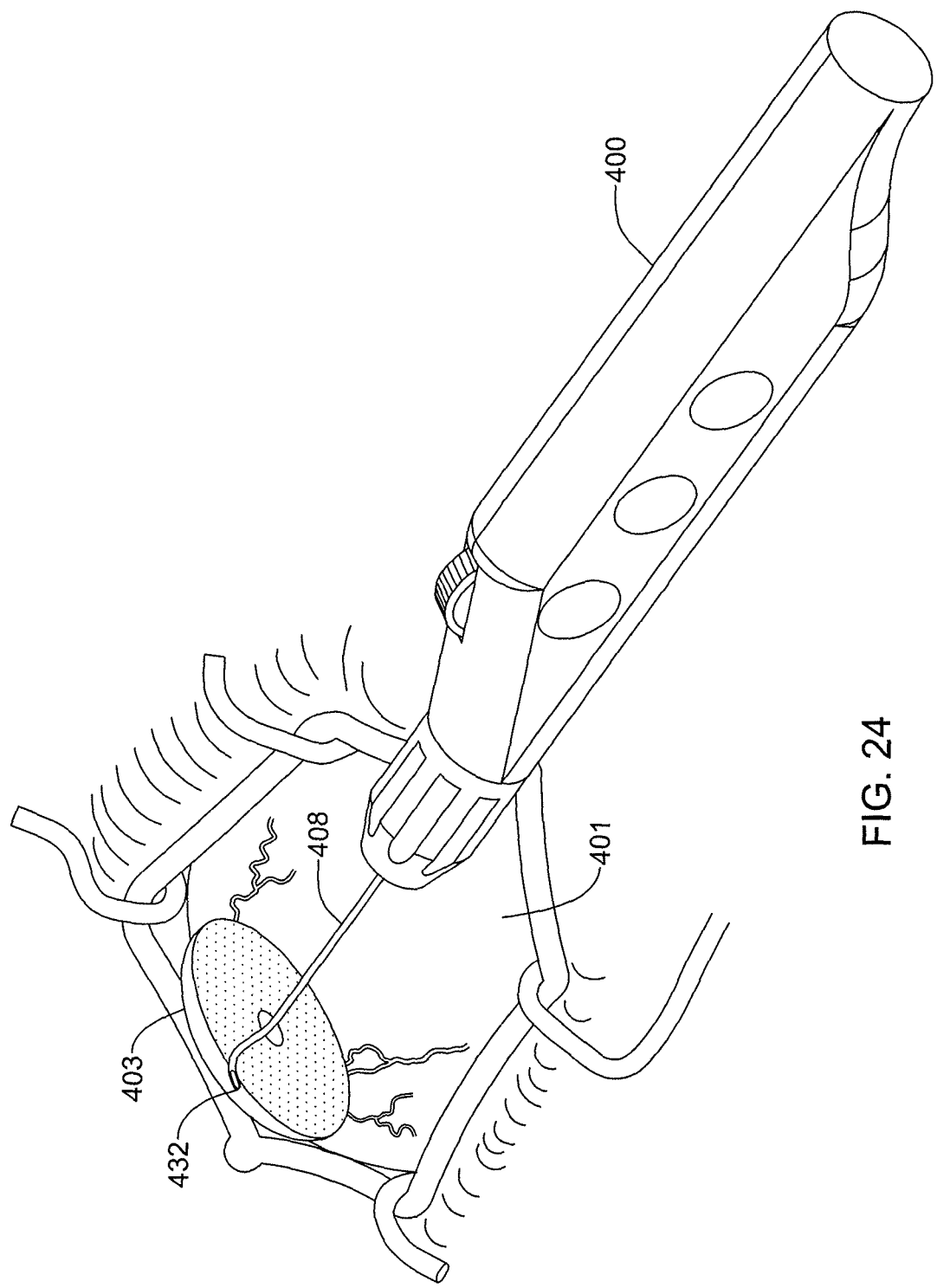
FIG. 24 is an enlarged perspective view further illustrating the delivery system shown in FIG. 23 and an eye.

FIG. 24 is an enlarged perspective view further illustrating delivery system 400 shown in the previous figure and an eye 401. In FIG. 24, cannula 408 of delivery system 400 is shown extending through a cornea 403 of eye 401. A distal portion of cannula 408 is disposed inside the anterior chamber defined by cornea 403 of eye 401. In the embodiment of FIG. 24, cannula 408 is configured so that a distal opening 432 of cannula 408 can be placed in fluid communication with Schlemm's canal. For example, distal portion 444 and intermediate portion 445 of cannula 408 may be dimensioned and configured such that cannula 408 may be advanced through an incision 407 created for another optical surgical procedure.

In the embodiment of FIG. 24, an ocular implant is disposed in a passageway defined by cannula 408. Delivery system 400 includes a mechanism that is capable of advancing and retracting the ocular implant along the length of cannula 408. The ocular implant may be placed in Schlemm's canal of eye 401 by advancing the ocular implant through the distal opening of cannula 408 while the distal opening is in fluid communication with Schlemm's canal.

Figure 25:
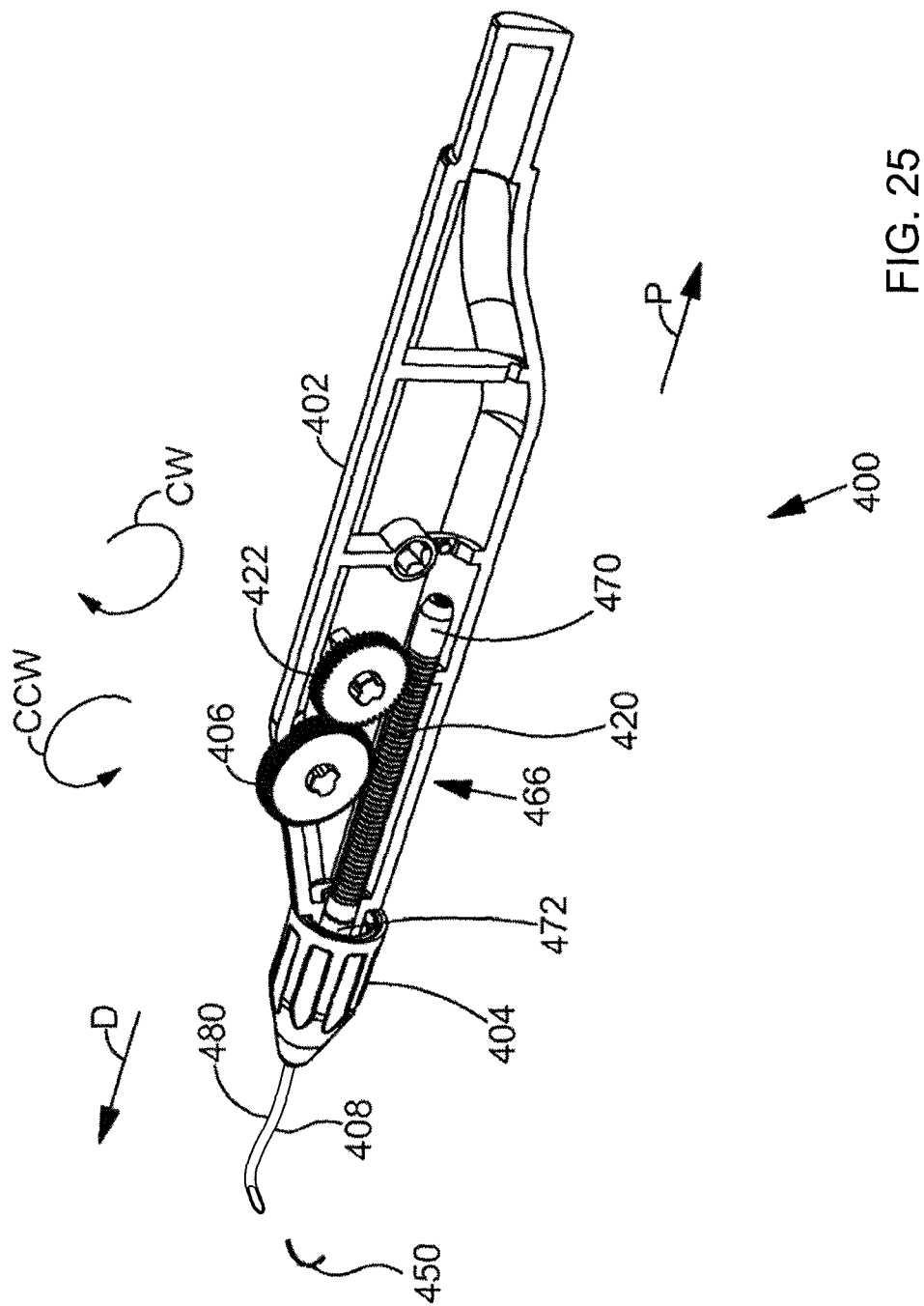
FIG. 25 is a perspective view further illustrating delivery system shown in FIG. 23.

FIG. 25 is a perspective view further illustrating delivery system 400 shown in the previous figure. In FIG. 25, a portion of housing 402 has been removed for purposes of illustration. Delivery system 400 includes a delivery tool subassembly 470 and a cannula subassembly 480. Delivery tool subassembly 470 includes rotating rack gear 420 and a delivery tool (not shown). In the embodiment of FIG. 25, the delivery tool extends into a passageway defined by a cannula 408. Cannula 408 can be seen extending beyond sleeve 404 in FIG. 25. Cannula subassembly 480 includes cannula 408, a hub 472, and an extension tube (not shown). In the embodiment of FIG. 25, the extension tube of cannula subassembly 480 is disposed inside a lumen defined by rotating rack gear 420.

Delivery system 400 includes a mechanism 466 that controls the movement of delivery tool subassembly 470. Mechanism 466 includes a number of components that are located inside housing 402, including tracking wheel 406, an idler gear 422, and the rotating rack gear 420. In the embodiment of FIG. 25, tracking wheel 406 and idler gear 422 are both rotatably supported by housing 402. Gear teeth on tracking wheel 406 engage gear teeth on idler gear 422, which in turn engage gear teeth on the rotating rack gear 420. Rotating tracking wheel 406 in a counter clockwise direction CCW causes idler gear 422 to rotate in a clockwise direction CW, which in turn causes the rotating rack gear 420 to move in a distal direction D. Rotating tracking wheel 406 in a clockwise direction CW causes idler gear 422 to rotate in a counter clockwise direction CCW, which in turn causes the rotating rack gear 420 to move in a proximal direction P. In other embodiments, the idler gear 422 may be eliminated from the device, which would cause counterclockwise movement of the tracking wheel to move the rack gear proximally.

In the embodiment of FIG. 25, a sleeve 404 is fixed to cannula subassembly 480. Sleeve 404 may be rotated by the user to change the orientation of cannula 408 with respect to housing 402. The sleeve 404 may include gripping features, such as grooves (as shown), a rubber coating, or other frictional surfaces to facilitate this use. In some applications, correct alignment between the cannula and iris is advantageous to ensure that the core tube and/or ocular implant is advanced at the correct trajectory relative to Schlemm's canal or other anatomy in the eye into which the ocular implant is to be implanted. The device is configured in a manner that keeps the ocular implant aligned within the device during rotation. Selected groups of components are keyed together to ensure that they rotate as a single body while simultaneously allowing axial movement of the ocular implant. In the embodiment of FIG. 25, cannula subassembly 480 and delivery tool subassembly 470 may rotate in unison with sleeve 404 relative to housing 402.

In the embodiment of FIG. 25, rotating rack gear 420 is configured to rotate with sleeve 404 while maintaining the ability to move axially in the distal and proximal directions before, during, and after rotation. As the rotating rack gear 420 moves distally and/or proximally, it causes corresponding movement of the delivery tool relative to cannula 408. This movement is transferred to ocular implant 450 when delivery tool 452 is coupled to ocular implant 450. Delivery tool subassembly 470 and cannula subassembly 480 engage one another in a keyed arrangement, as described in more detail below. This keyed arrangement causes delivery tool subassembly 470 and cannula subassembly 480 to maintain a constant rotational orientation relative to each other while, at the same time, allowing delivery tool subassembly 470 to translate in a distal direction D and a proximal direction P relative to cannula subassembly 480.

Figure 26:
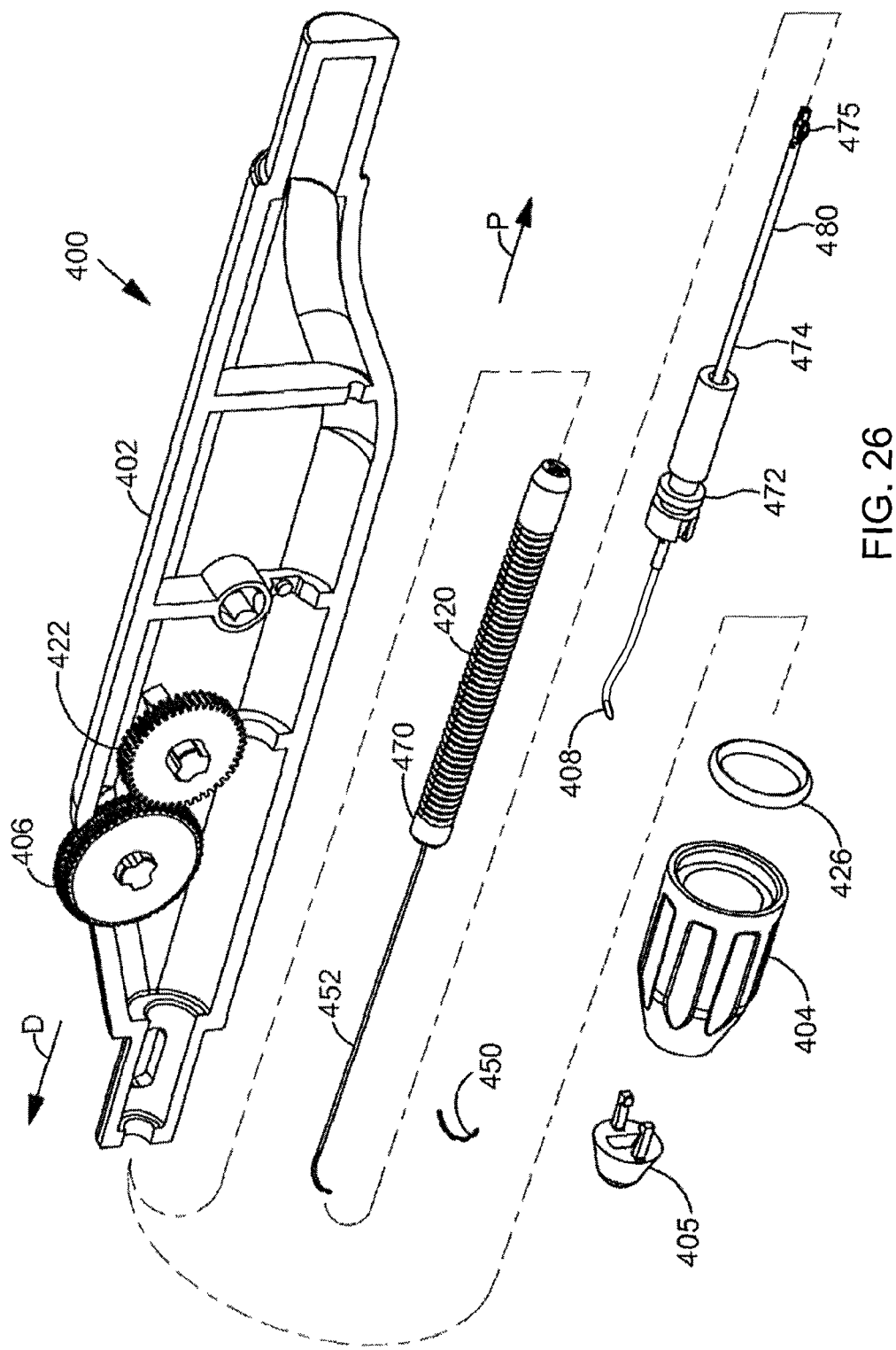
FIG. 26 is an exploded view illustrating various elements of another illustrative delivery system in accordance with the detailed description.

FIG. 26 is an exploded view illustrating various elements of delivery system 400. Cannula subassembly 480 includes a hub 472 and an extension tube 474 that are both fixed to cannula 408. Extension tube 474 includes a shaped portion 475 that is dimensioned and shaped to fit within a shaped through hole 477 (shown in FIG. 26A) by rotating rack gear 420. FIG. 26A shows an end view of rotating rack gear 420 and through hole 477. This keyed arrangement causes delivery tool subassembly 470 and cannula subassembly 480 to maintain a constant rotational orientation relative to each other while, at the same time, allowing delivery tool subassembly 470 to translate in a distal direction D and a proximal direction P relative to cannula subassembly 480.

In some embodiments, delivery tool 452 is formed from shape memory material (such as, e.g., nitinol), and at least a portion of delivery tool 452 assumes a curved at-rest shape when no external forces are acting on it. Delivery tool 452 can be urged to assume a straightened shape, for example, by inserting delivery tool 452 through a straight portion of the passageway defined by cannula 408. When the delivery tool 452 is confined, such as within cannula 408, the interlocking portion can engage the complementary interlocking portion to join the delivery tool and ocular implant together, and allow the delivery tool and ocular implant to move together through the cannula 408, as described in more detail below.

Delivery system 400 also includes an O-ring 426 disposed between sleeve 404 and housing 402. O-ring 426 can provide friction and/or resistance between sleeve 404 and housing 402. This friction and/or resistance may be useful, for example, to hold the sleeve 404 in a desired orientation. A noseplug 405 snaps into the distal end of the delivery system.

Figure 27:
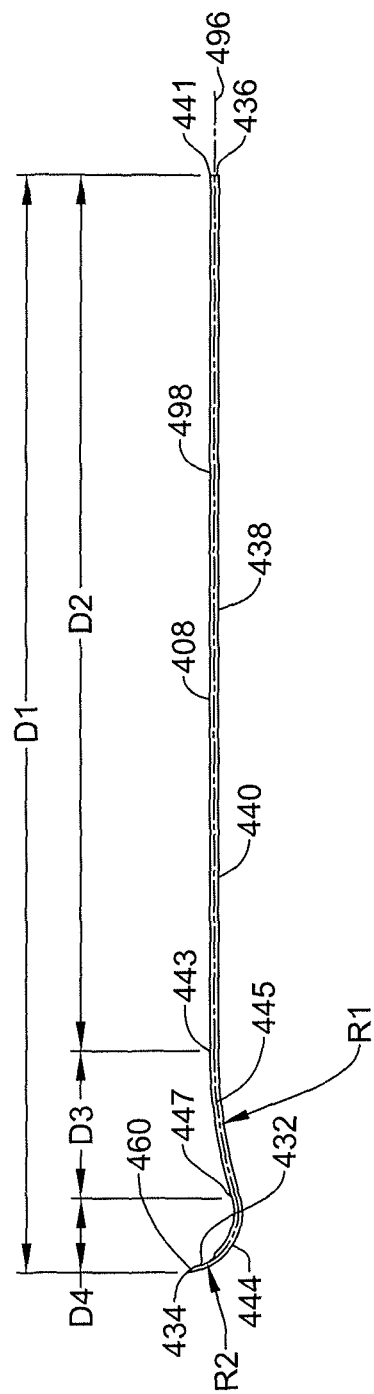
FIG. 27 is a side view further illustrating the cannula shown in FIG. 23.
Figure 28:
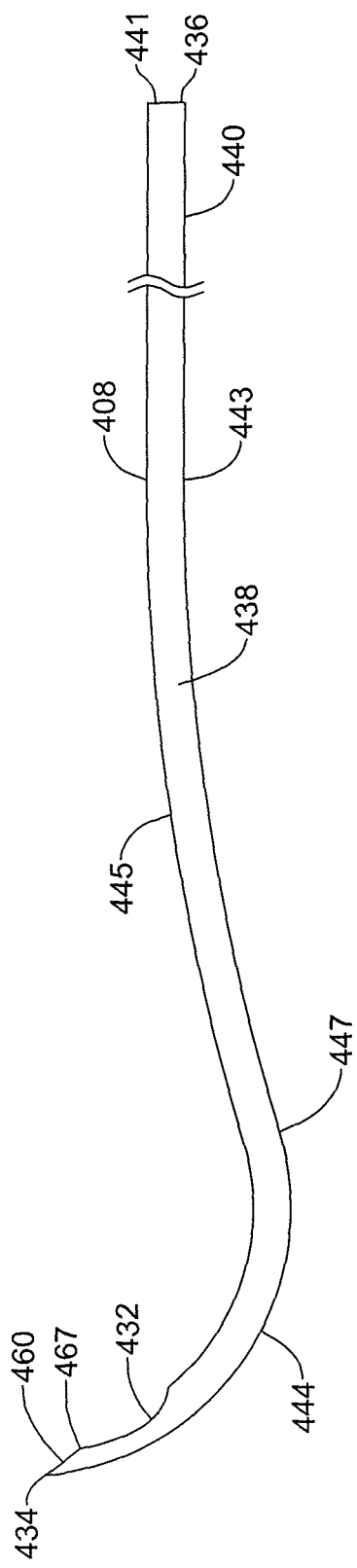
FIG. 28 is an enlarged detail view further illustrating the cannula shown in FIG. 23.
Figure 29:
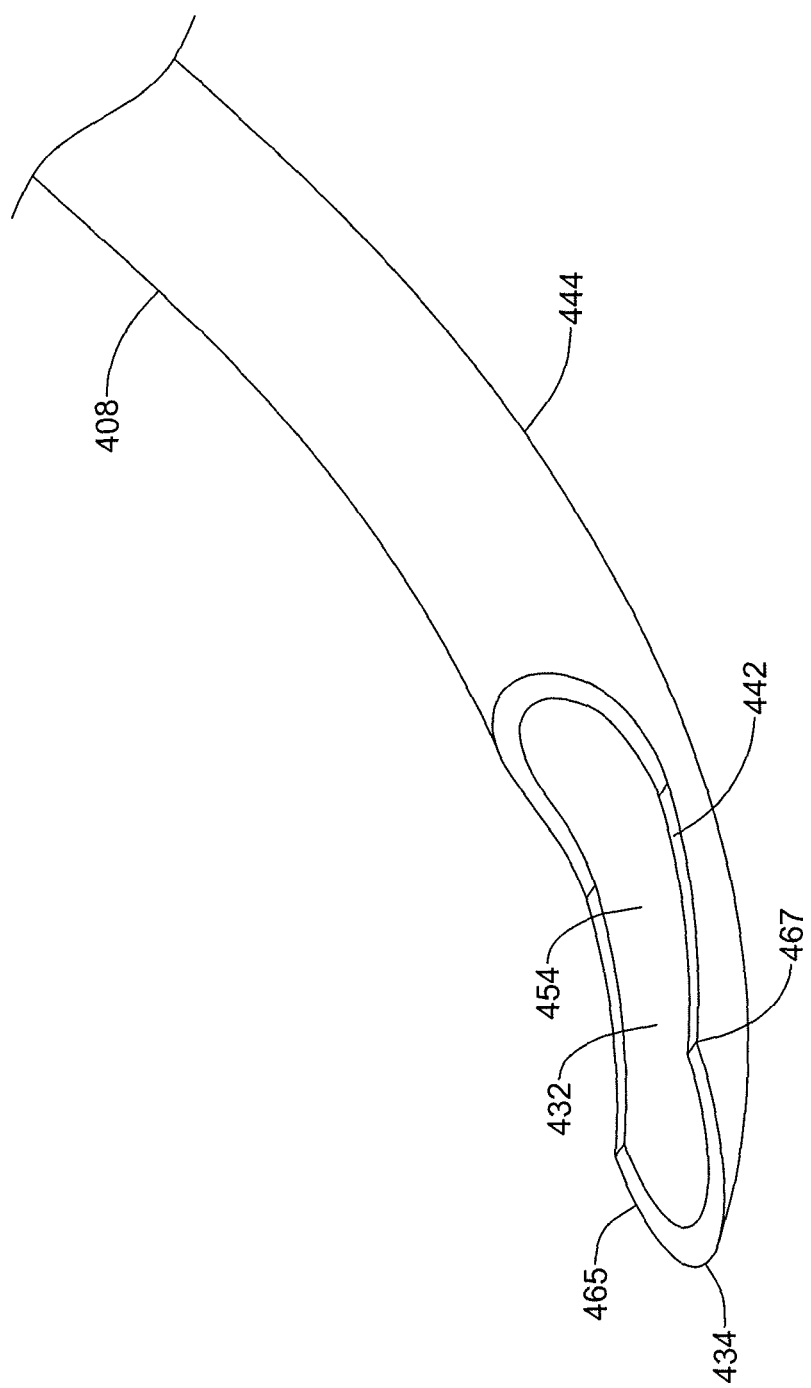
FIG. 29 is an enlarged perspective view further illustrating the distal portion of the cannula shown in FIG. 23.

FIGS. 27, 28, and 29 illustrate more detailed views of cannula 408. FIG. 27 is a side view of a cannula 408 in accordance with the present detailed description, FIG. 28 is an enlarged detail view of cannula 408, and FIG. 29 is an enlarged perspective view further illustrating a portion of distal portion 444 of cannula 408. Cannula 408 comprises a generally tubular member 498 having a central axis 496. Generally, tubular member 498 comprises a proximal end 441, a proximal portion 440, an intermediate portion 445, a distal portion 444, and a distal end 434. Cannula 408 may extend a distance D1 between proximal end 441 and distal end 434. Tubular member 498 may have a length along central axis 496 that is longer than distance D1 between proximal end 441 and distal end 434. For purposes of example, It is contemplated that distance D1 may be in the range of 1.50 to 3.50 inches (3.81 to 8.89 centimeters), 2.0 to 3.0 inches (5.08 to 7.62 centimeters) or around 2.50 inches (6.35 centimeters). It is contemplated cannula 408 may span any distance D1 desired. Proximal portion 440 may extend over a distance D2 from proximal end 441 to a point 443 distal to proximal end 441. Proximal portion 440 may be generally straight such that distance D2 is approximately equal to or equal to a length of proximal portion 440 measured along central axis 496. Distance D2 may be in the range of 1.50 to 2.50 inches (3.81 to 6.35 centimeters), 1.75 to 2.25 inches (4.45 to 5.72 centimeters), or around 2.0 inches (5.08 centimeters). Intermediate portion 445 may extend between first point 443 and a second point 447 located proximal to distal end 434 of cannula 408. Intermediate portion 445 may span a distance D3 extending from point 443 and point 447. Distance D3 may be in the range of 0.15 to 0.50 inches (0.38 to 1.27 centimeters), 0.25 to 0.40 inches (0.64 to 1.02 centimeters), or around 0.33 inches (0.84 centimeters). Intermediate portion 445 may have a length along central axis 496 of tubular member 498 that is longer than distance D3. The difference in the length of intermediate portion 445 and the distance D3 may be determined by the degree of curvature of intermediate portion 445, as will be discussed in more detail below. Distal portion 444 may extend between second point 447 and distal end 434. Distal portion 444 may span a distance D4 extending from point 447 and distal end point 434. Distance D4 may be in the range of 0.05 to 0.30 inches (0.13 to 0.76 centimeters), 0.13 to 0.23 inches (0.33 to 0.58 centimeters), or around 0.17 inches (0.43 centimeters). Distal portion 444 may have a length along central axis 496 of tubular member 498 that is longer than distance D4. The difference in the length of distal portion 444 and the distance D4 may be determined by the degree of curvature of distal portion 444, as will be discussed in more detail below.

A distal opening surface 442 surrounds a distal opening 432 extending through the distal end 434 and through a side wall of cannula 408. A beveled edge 465 is disposed at the distal end of distal opening surface 442, extending from the distal end 434 to a proximal extent 467 of beveled edge 465. Tubular member 498 defines distal opening 432, a proximal opening 436, and a passageway 438 extending between proximal opening 436 and distal opening 432.

Proximal portion 440 of cannula 408 is substantially straight while intermediate portion 445 and distal portion 444 of cannula 408 may be curved. In the embodiment of FIG. 27, distal portion 444 is curved along its entire length and intermediate portion 445 is curved along its entire length. Intermediate portion 445 may define a curve having a first radius R1 measured from central axis 496 and defining a first radius of curvature. The length of intermediate portion 445 along central axis 496 may be determined by the measure of the arc (in degrees) and the radius of the curve using Equation 1 below:

$$L_{arc} = \theta\left(\frac{\pi}{180}\right)r \qquad \text{Equation 1}$$

where $L_{arc}$ is the length of the arc, $\theta$ is the angle measure of the arc (in degrees), and r is the radius of the circle. In some instances, the angle measure of intermediate portion 445 may be in the range of 10° to 25°, although other angles are possible. Distal portion 444 may define a curve having a second radius R2 and defining a second radius of curvature. The length of distal portion 444 along central axis 496 may be determined by the measure of the arc (in degrees) and the radius of the curve using Equation 1 above. In some instances, the angle measure of distal portion 444 may be in the range of 90° to 110°, although other angles are possible. It is contemplated that the first radius R1 may be larger than the second radius R2 such that the distal portion 444 has a higher curvature than the intermediate portion 445. This configuration may advance the ocular implant at the correct trajectory relative to Schlemm's canal or other anatomy in the eye into which the ocular implant is to be implanted. For example, the configuration may allow the cannula 408 to be advanced through an incision generally along a major axis of the visible eye and allowing for substantially tangential entry of cannula 408 into Schlemm's canal. It is contemplated that first radius R1 and second radius R2 may be selected to facilitate delivery of implant 450 to other anatomical locations.

Figure 27A:
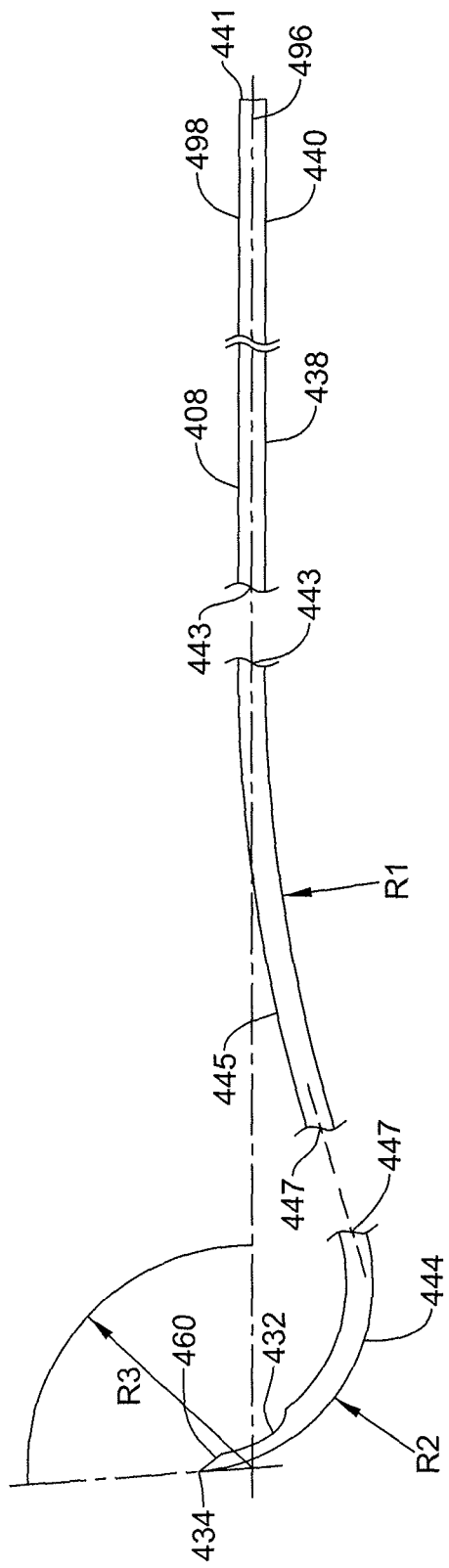
FIG. 27A is an additional side view illustrating the cannula shown in FIG. 23.

FIG. 27A is an additional side view and illustrates a sectioned view of the cannula shown in FIG. 23. For purposes of example, cannula 408 comprises a generally tubular member 498 having a central axis 496. Generally tubular member 498 comprises a proximal end 441, a proximal portion 440, an intermediate portion 445, a distal portion 444, and a distal end 434. Additionally, for example, the central axis 496 of proximal portion 440 is tangential to the tangential line at first point 443 of intermediate portion 445. Further, the tangential line at second point 447 of intermediate portion 445 is tangential to the tangential line of the second point 447 of distal portion 444. The tangential line at distal end 434 of distal portion 444 and the central axis 496 of proximal portion may have third radius R3, for example, having an angle approximately in the range of 90° to 165°.

A method in accordance with this detailed description may include the step of advancing the distal end 434 of cannula 408 through the cornea of a human eye so that distal end 434 is disposed in the anterior chamber of the eye. Cannula 408 may then be used to access Schlemm's canal of the eye, for example, by piercing the wall of Schlemm's canal with the distal end 434 of cannula 408. The beveled edge 465 may be inserted into Schlemm's canal to place at least part of distal opening 432 of cannula 408 in communication with Schlemm's canal. For example, cannula 408 may be advanced until the distal tip 434 and beveled edge 465 of cannula 408 have been inserted into Schlemm's canal up to the proximal extent 467 of beveled edge 465. With the passageway of the cannula 408 placed in fluid communication with the lumen of Schlemm's canal, the ocular implant may be advanced out of a distal port of the cannula 408 and into Schlemm's canal.

In the embodiment of FIG. 28 and further illustrated in FIG. 29, distal portion 444 of cannula 408 defines a trough 454. In some embodiments, trough 454 is configured to receive the entire external cross section of an ocular implant as the ocular implant is being advanced into Schlemm's canal. When this is the case, trough 454 may have a depth dimension that is deeper than a width of the ocular implant. This cannula configuration advantageously prevents the ocular implant from intersecting the layers of the trabecular meshwork as the ocular implant is advanced into Schlemm's canal. Trough 454 may also be configured to allow the proximal portion of the ocular implant to be released from the delivery tool in a manner similar to trough 154 described above.

Referring briefly to FIG. 23B, while not explicitly shown, during advancement of ocular implant 450 interlocking portion 460 of delivery tool 452 and complementary interlocking portion 462 of ocular implant 450 may be engaged with each other so that a proximal end of ocular implant 450 is proximal to the distal end of delivery tool 452. Surface 461 of delivery tool 452 rests against the wall of cannula 408 to prevent interlocking portion 460 of delivery tool 452 and complementary interlocking portion 462 of ocular implant 450 from disengaging one another. When they are connected in this fashion, delivery tool 452 and ocular implant 450 move together as the delivery tool is advanced and retracted relative to cannula 408 by the delivery system mechanism. In some embodiments, the ocular implant 450 has a radius of curvature that is larger than the radius of curvature of the distal portion 444 of cannula 408. This arrangement ensures that the ocular implant will track along trough 454 as the ocular implant is urged in a distal direction by delivery system 400.

Once cannula 408 has been positioned in the desired location, ocular implant 450 may be advanced distally while cannula 408 is held stationary. Elongate opening 432 may provide direct visualization of ocular implant 450 as it is advanced into Schlemm's canal. A configuration allowing direct visualization of the ocular implant has a number of clinical advantages. During a medical procedure, it is often difficult to monitor the progress of the implant by viewing the implant through the trabecular meshwork. For example, blood reflux may push blood into Schlemm's canal obstructing a physician's view the portion of the implant that has entered Schlemm's canal. Ocular implant 450 tracks along trough 454 as it is advanced distally along cannula 408. The trough opening allows the physician to monitor the progress of the implant by viewing the implant structures as they advance through the trough prior to entering Schlemm's canal. The trough opening also allows the physician to identify the position of the proximal end of the ocular implant with respect to the incision made by the cannula to access Schlemm's canal.

Delivery tool 452 may advance ocular implant 450 distally until delivery tool surface 461 and part of the reduced diameter portion 463 have now passed into opening 432, thereby permitting the delivery tool curved portion to move toward its curved at-rest shape so that the delivery tool engagement surface 460 disengages and moves away from its complementary engagement surface 462 on the ocular implant 450. After the disengaging from the ocular implant, cannula 408 and delivery tool 452 can be withdrawn from Schlemm's canal leaving the ocular implant 450 in the fully deployed position. After delivery of ocular implant 450 is complete, the delivery tool 452 and the cannula 408 may be removed from the eye, leaving at least a distal portion of the ocular implant 450 in Schlemm's canal. An inlet portion of ocular implant 450 may be positioned in the anterior chamber of the eye and the remainder of ocular implant 450 in Schlemm's canal. The presence of ocular implant 450 in Schlemm's canal may facilitate the flow of aqueous humor out of the anterior chamber. This flow may include axial flow along Schlemm's canal, flow from the anterior chamber into Schlemm's canal, and flow leaving Schlemm's canal via outlets communicating with Schlemm's canal. When in place within the eye, ocular implant 450 will support the trabecular meshwork and Schlemm's canal tissue and will provide for improved communication between the anterior chamber and Schlemm's canal (via the trabecular meshwork) and between pockets or compartments along Schlemm's canal.

Components of ocular device may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, utylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also can be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, which are incorporated herein by reference. Other suitable materials may include ULTANIUM™ (available from Neo-Metrics) and GUM METAL™ (available from Toyota). In some other embodiments, a superelastic alloy, for example a superelastic nitinol can be used to achieve desired properties.

It is to be understood that even though numerous characteristics of various embodiments have been set forth in the foregoing description, together with details of the structure and function of various embodiments, this detailed description is illustrative only, and changes may be made in detail, especially in matters of structure and arrangements of parts illustrated by the various embodiments to the full extent indicated by the broad general meaning of the terms in which the appended claims are expressed.

What is claimed is:

1. A system for delivering an ocular implant into Schlemm's canal through an incision associated with cataract surgery, the system comprising:
a cannula defining a central axis and a passageway extending from a proximal end to a distal end along the central axis, the cannula having a distal opening extending through a side wall and the distal end of the cannula to form a trough, a curved distal portion, a curved intermediate portion, and a proximal portion;
an ocular implant disposed within the passageway of the cannula; and
a delivery tool having a distal interlocking portion engaging a complementary interlocking portion of the ocular implant; and
wherein the intermediate portion of the cannula has a first radius of curvature along the central axis and the distal portion has a second radius of curvature along the central axis, the first radius of curvature being greater than the second radius of curvature to allow for substantially tangential entry of the cannula into Schlemm's canal through the incision.

2. The system of claim 1, wherein the intermediate portion of the cannula extends distally from a first point distal to the proximal end to a second point proximal to the distal end and the distal portion extends distally from the second point to the distal end.

3. The system of claim 1, wherein the distal interlocking portion of the delivery tool and the complementary interlocking portion of the ocular implant form a mechanically interlocking connection when the interlocking portion of the delivery tool is proximal to the trough portion of the cannula.

4. The system of claim 1, wherein the distal interlocking portion of the delivery tool has an at-rest shape different from the shape of the cannula, the cannula side wall preventing the delivery tool from assuming its at-rest shape when the interlocking portion of the delivery tool is proximal to the trough of the cannula.

5. The system of claim 4, wherein the delivery tool at-rest shape is a curve having a smaller radius of curvature than the second radius of curvature of the cannula.

6. The system of claim 1, wherein an angle between a line tangential to the distal end of the cannula and the central axis of the proximal portion of the cannula is in the range of 90° to 165°.

7. A cannula for delivering an ocular implant into Schlemm's canal of an eye through an incision associated with cataract surgery, the cannula comprising:
   a tubular member having a central axis and a side wall and extending from a proximal end to a distal end, the tubular member comprising:
      a passageway extending from the proximal end to the distal end of the tubular member along the central axis;
      a generally straight proximal portion extending distally from the proximal end to a first point;
      a curved intermediate portion extending distally from the first point to a second point proximal to the distal end;
      a curved distal portion extending distally from the second point to the distal end; and
      a distal opening extending through the side wall and the distal end of the cannula to form a trough; and
      wherein the intermediate portion of the cannula has a first radius of curvature along the central axis and the distal portion has a second radius of curvature along the central axis and the first radius of curvature is greater than the second radius of curvature to allow for substantially tangential entry of the cannula into Schlemm's canal through the incision.

8. The cannula of claim 7, wherein the passageway is configured to receive the ocular implant.

9. A method of deploying an ocular implant into Schlemm's canal of an eye, comprising:
   inserting a distal end of a cannula through an incision optimized for cataract surgery in a cornea of the eye and into an anterior chamber of the eye, the cannula comprising a central axis and a passageway extending from a proximal end to a distal end along the central axis, the cannula further comprising a distal opening extending through a side wall and the distal end of the cannula to form a trough, a curved distal portion, a curved intermediate portion, and a proximal portion, wherein the curved intermediate portion of the cannula has a first radius of curvature along the central axis and the distal curved portion has a second radius of curvature along the central axis different than the first radius of curvature;
   placing the distal opening of the cannula into fluid communication with Schlemm's canal;
   advancing an ocular implant distally through the cannula with a delivery tool engaged with the ocular implant, a proximal portion of the ocular implant engaging the delivery tool proximal to a distal portion of the delivery tool; and
   disengaging the ocular implant and the delivery tool when the proximal portion of the ocular implant reaches distal opening of the cannula.

10. The method of claim 9, wherein the intermediate portion of the cannula extends distally from a first point distal to the proximal end to a second point proximal to the distal end and the distal portion extends distally from the second point to the distal end.

11. The method of claim 9, wherein the first radius of curvature is greater than the second radius of curvature.

12. The method of claim 9, wherein the disengaging step comprises separating the distal portion of the delivery tool and the ocular implant from each other when the distal portion of the delivery tool passes through the distal opening of the cannula.

13. The method of claim 12, wherein the separating step is performed before the distal portion of the delivery tool reaches the distal end of the cannula.

14. The method of claim 12, wherein the separating step comprises maintaining contact between the ocular implant and the cannula and moving the distal portion of the delivery tool away from the cannula.

15. The method of claim 14, wherein the distal portion of the delivery tool has an at-rest shape, the separating step further comprising permitting the distal portion of the delivery tool to assume its at-rest shape.

16. The method of claim 15, wherein the at-rest shape is a curve having a smaller radius of curvature than the second radius of curvature of the cannula.

17. A method of deploying an ocular implant into Schlemm's canal of an eye, comprising:
   inserting a distal end of a cannula through an incision in the eye and into an anterior chamber of the eye, wherein a location of the incision is optimized for a cataract surgery, the cannula comprising a central axis and a passageway extending from a proximal end to a distal end along the central axis, the cannula further comprising a distal opening extending through a side wall and the distal end of the cannula to form a trough, a curved distal portion, a curved intermediate portion, and a proximal portion, wherein the curved intermediate portion of the cannula has a first radius of curvature along the central axis and the curved distal portion has a second radius of curvature along the central axis different than the first radius of curvature;
   placing the distal opening of the cannula into fluid communication with Schlemm's canal such that the cannula enters Schlemm's canal in a substantially tangential orientation;
   advancing an ocular implant distally through the cannula with a delivery tool engaged with the ocular implant, a proximal portion of the ocular implant engaging the delivery tool proximal to a distal portion of the delivery tool; and
   disengaging the ocular implant and the delivery tool when the proximal portion of the ocular implant reaches distal opening of the cannula.

18. The method of claim 17, wherein the intermediate portion of the cannula extends distally from a first point distal to the proximal end to a second point proximal to the distal end and the distal portion extends distally from the second point to the distal end.

19. The method of claim 17, wherein the first radius of curvature is greater than the second radius of curvature.

20. The method of claim 17, wherein the disengaging step comprises separating the distal portion of the delivery tool and the ocular implant from each other when the distal portion of the delivery tool passes through the distal opening of the cannula.

21. The method of claim 20, wherein the separating step is performed before the distal portion of the delivery tool reaches the distal end of the cannula.

22. The method of claim 20, wherein the separating step comprises maintaining contact between the ocular implant and the cannula and moving the distal portion of the delivery tool away from the cannula.

23. The method of claim 22, wherein the distal portion of the delivery tool has an at-rest shape, the separating step further comprising permitting the distal portion of the delivery tool to assume its at-rest shape.

24. The method of claim 23, wherein the at-rest shape is a curve having a smaller radius of curvature than the second radius of curvature of the cannula.

\* \* \* \* \*